(12) United States Patent
Brownlie et al.

(10) Patent No.: US 7,776,340 B2
(45) Date of Patent: Aug. 17, 2010

(54) CANINE RESPIRATORY CORONAVIRUS (CRCV) SPIKE PROTEIN, POLYMERASE AND HEMAGGLUTININ/ESTERASE

(75) Inventors: John Brownlie, Hatfield (GB); Victoria Jane Chalker, Hatfield (GB); Kerstin Erles, Hatfield (GB)

(73) Assignee: The Royal Veterinary College, London (GB)

( * ) Notice: Subject to any disclaimer, the term of this patent is extended or adjusted under 35 U.S.C. 154(b) by 674 days.

(21) Appl. No.: 10/522,513

(22) PCT Filed: Jul. 1, 2003

(86) PCT No.: PCT/GB03/02832

§ 371 (c)(1), (2), (4) Date: Jun. 22, 2006

(87) PCT Pub. No.: WO2004/011651

PCT Pub. Date: Feb. 5, 2004

(65) Prior Publication Data

US 2007/0248616 A1  Oct. 25, 2007

(30) Foreign Application Priority Data

Jul. 27, 2002  (GB) .................................. 0217434.0

(51) Int. Cl.
| | |
|---|---|
| A61K 49/00 | (2006.01) |
| A61K 39/38 | (2006.01) |
| A61K 39/00 | (2006.01) |
| A61K 39/12 | (2006.01) |
| A61K 39/295 | (2006.01) |
| A61K 39/155 | (2006.01) |
| A61K 39/23 | (2006.01) |
| A61K 39/10 | (2006.01) |
| A61K 39/275 | (2006.01) |

(52) U.S. Cl. ............... 424/221.1; 424/184.1; 424/185.1; 424/186.1; 424/204.1; 424/9.2; 424/211.1; 424/233.1; 424/253.1; 424/201.1

(58) Field of Classification Search .................. None
See application file for complete search history.

(56) References Cited

U.S. PATENT DOCUMENTS

| | | | |
|---|---|---|---|
| 4,567,043 A * | 1/1986 | Acree et al. ............... 424/202.1 |
| 5,672,350 A | 9/1997 | Parker et al. |
| 5,750,112 A | 5/1998 | Gill |
| 5,916,570 A | 6/1999 | Kapil |
| 6,057,436 A | 5/2000 | Miller et al. |
| 6,280,974 B1 | 8/2001 | Miller et al. |
| 6,372,224 B1 | 4/2002 | Miller et al. |
| 6,974,577 B2 * | 12/2005 | Knape et al. ............. 424/201.1 |

FOREIGN PATENT DOCUMENTS

| | | |
|---|---|---|
| EP | 0 510 773 | 10/1992 |
| WO | WO 93/23423 | 11/1992 |
| WO | WO 98/16643 | 4/1998 |
| WO | WO 99/25838 | 5/1999 |

OTHER PUBLICATIONS

Genbank Accession # AF058944, Published Jan. 17, 2000.*
Erles and Brownlie, Canine Respiratory Coronavirus: An emerging Pathogen, 2008, Veterinary Clinics of North America. Small animal practice, vol. 38, No. 4, pp. 815-825.*
Decaro and Buonavoglia, An update on canine coronaviruses: Viral evolution and pathobiology, 2008, Veterinary Microbiology, vol. 132, pp. 221-234.*
American Veterinary Medical Association online publication, "Frequently Asked Questions about Canine Respiratory Coronavirus", Apr. 2008, accessed from <http://www.avma.org/animal_health/canine_coronavirus_faq.asp>, on Dec. 1, 2008.*
Hajer and Storz, Structural Polypeptides of the Enteropathogenic Bovine Coronavirus Strain LY-138, 1979, Archives of Virology, vol. 59, pp. 47-57.*
Examination Report dated Jul. 17, 2007 corresponding to Patent Application No. NZ 556442.
GenBank Accession No. AAF25519, Jan. 17, 2000.
GenBank Accession No. AF058944, Jan. 17, 2000.
GenBank Accession No. P25191, Nov. 4, 2008.
GenBank Accession No. P25194, Nov. 4, 2008.
GenBank Accession No. S44240, Sep. 20, 1999.
Appel and Binn (1987), in "Virus infections of carnivores", Appel, Ed., 1st Edition, pp. 201-211, Elsevier Science Publishers, Amsterdam.
Balaguer et al (1991) Anal Biochem 195:105-110.
Becker and Guarente (1991) Methods Enzymol 194:182-187.
Beggs (1978) Nature 275:104-109.
Bemis et al (1977) Cornell Vet 67:282-293.
Better et al (1988) Science 240:1041-1047.
Binn et al (1967) Proc Soc Exp Biol Med 126:140-145.

(Continued)

*Primary Examiner*—Patrick J Nolan
*Assistant Examiner*—Benjamin P Blumel
(74) *Attorney, Agent, or Firm*—Knobbe Martens Olson & Bear LLP

(57) ABSTRACT

A canine respiratory coronavirus (CRCV) that is present in the respiratory tract of dogs with canine infectious respiratory disease and which has a low level of homology to the enteric canine coronavirus, but which has a high level of homology to all bovine coronavirus strains (eg Quebec and LY138) and human coronavirus strain OC43. The CRCV spike, polymerase and hemagglutinin/esterase cDNA and protein partial sequences are listed in FIGS. (1) to (4), (13) and (14).

```
ctcagatgaa tttgaaatat gctattagtg ctaagaatag
                                agcccgcact gttgctggtg   60
tttccatact tagtactatg actggcagaa tgtttcatca
                                aaaatgtttg aaaagtatag  120
cagctacacg tggtgttcct gttgttatag gcaccactaa
                                attttatggc ggctgggatg  180
atatgttacg tcgccttatt aaagatgttg acaatcctgt
                                acttatgggt tgggattatc  240
ctaagtgtga                                              250
```

10 Claims, 40 Drawing Sheets

OTHER PUBLICATIONS

Binn et al (1979) Lab Anim Sci 29:48-52.
Bird et al (1988) Science 242:423-426.
Cavanagh et al, pp. 407-411, in "Virus Taxonomy, 6th Report of the International Committee on Taxonomy of Viruses", Murphy et al, Eds., Springer-Verlag Wein, New York.
Chilvers et al (2001) Eur Respir J 18:965-970.
Cohen et al (1972) Proc Natl Acad Sci USA 69:2110-2114.
Compton (1991) Nature 350:91-92.
Coyne and May (1995) "Considerations in using a canine coronavirus vaccine", published as a Pfizer Technical Bulletin at http://www.pfizer.com/ah/vet/tref/trbull/ccv.html).
DiCesare et al (1993) BioTechniques 15:152-157.
Ditchfield et at (1962) Can Vet Jour 3:238-247.
Erles et al (2003) Virology 310:216-223.
Felsenstein (1989) PHYLIP-Phylogeny Inference Package (Version 3.2c), Cladistics 5:164-166.
GCG Version 10.3: Section of the Program Manual for the GCG Package, Version 10.3, relating to the GAP alignment (1982-2002), Genetics Computer Group, 575 Science Drive, Madison, Wisconsin US 53711.
GenBank Accession No. AF058942 (2000).
GenBank Accession No. AAM 77000 (2005).
GenBank Accession No. AF124985 (1999).
GenBank Accession No. AF124986 (1999).
GenBank Accession No. AF124989 (1999).
GenBank Accession No. AF220295 (2003).
GenBank Accession No. AF481863 (2002).
GenBank Accession No. L07747 (2001).
GenBank Accession No. L14643 (2002).
GenBank Accession No. M76373 (2002).
GenBank Accession No. M84486 (1993).
GenBank Accession No. Z32768 (2002).
Grand Laboratories Inc. Technical Information on Scour Bos TM 4. http://www.grandlab.com/bioproducts (2000).
Hawoksuz et al (1999) Archives of Virology 144:2441-2447.
Huston et al (1988) Proc Natl Acad Sci USA 85:5879-5883.
Iacobelli et al (1988) Breast Cancer Research and Treatment 11:19-30.
Ignjatovic and Sapats (2000) Rev Sci Tech 19:493-508.
Jacobs et al (1988) Nucl Acids Res 16:4637-4650.
Jalkanen et al (1985) J Cell Biol 101:976-984.
Jalkanen et al (1987) J Cell Biol 105:3087-3096.
Karpas et al (1968) Proc Soc Exp Biol Med 127:45-52.
Keil and Fenwick (1998) J Am Vet Med Assoc 212:200-207.
Lai and Cavanagh (1997) Adv Vir Res 48:4-22.
Lou and Wenner (1963) Am J Hyg 77:293-304.
Lu et al (1981) J Org Chem 46:3433-3436.
Luchansky et al (1988) Mol Microbiol 2:637-646.
Makela et al (1998) J Clin Microbiol 36:539-542.
Morrison et al (1984) Proc Natl Acad Sci USA 81:6851-6855.
National Office of Animal Health Ltd (NOAH), Middlesex UK(2001), "Compendium of Data Sheets for Veterinary Products 2002-2003".pp. 216-217, 228-231, 322, 355-363, 448-449, 602-604, 700-702, 703-705, 759-761.
Neuberger et al (1988) 8th International Biotechnology Symposium Part 2, pp. 792-799.
Page (1996) Computer Applications in the Biosciences 12:357-358.
Pearson and Lipman (1988) Proc Natl Acad Sci USA 85:2444-2448.
Pensaert et al (1986) Vet Q 8:257-261.
Pfizer Animal Health Technical Services. Label Info for Scour Guard 3K. http://www.americanlivestock.com/showLabelInfo.jsp-?productFamilyId=1075, 2002.
Randolph et al (1993) Am J Vet Res 54:387-391.
Saiki et al (1986) Nature 324:163-166.
Schering-Plough Animal Health News Archives (1999), "Schering-Plough Animal Health Secures First EU Approval for One Shot Calf Scours Vacine" Rotavec TM Corona. http://www.spah.com/usa/news/pr/pr41.cfm.
Skerra and Pluckthun (1988) Science 240:1038-1041.
Southern (1975) J Mol Biol 98:503-517.
Spaan et al (1988) J Gen Virol 69:2939-2952.
Stephensen et al (1999) Virus Res 60:181-189.
Storz et al (2000) J Clin Microbiology 38:3291-3298.
Tennant et al (1993) Vet Rec 132:7-11.
Thompson et al (1997) Nucl Acids Res 25:4876-4882.
Walker et al (1992) Nucl Acids Res 20:1691-1696.
Ward et al (1989) Nature 341:544-546.
Winter and Milstein (1991) Nature 349:293-299.

* cited by examiner

FIGURE 1

```
ctcagatgaa tttgaaatat gctattagtg ctaagaatag agcccgcact gttgctggtg    60
tttccatact tagtactatg actggcagaa tgtttcatca aaaatgtttg aaaagtatag   120
cagctacacg tggtgttcct gttgttatag gcaccactaa attttatggc ggctgggatg   180
atatgttacg tcgccttatt aaagatgttg acaatcctgt acttatgggt tgggattatc   240
ctaagtgtga                                                          250
```

FIGURE 2

```
QMNLKYAISA KNRARTVAGV SILSTMTGRM FHQKCLKSIA ATRGVPVVIG TTKFYGGWDD    60
MLRRLIKDVE NPVLMGWDYP KCE                                           84
```

FIGURE 3 (Page 1 of 2)

```
atgtttttga tacttttaat ttccttacca atggcttttg ctgttatagg agatttaaag      60
tgtactacgg tttccatcaa tgatgttgac accggtgctc cttctattag cactgatgtt     120
gtcgatgtta ctaatggttt aggtacttat tatgttttag atcgtgtgta tttaaatact     180
acattgttgc ttaatggtta ttatcctact tcaggttcta catatcgtaa tatggcactg     240
aagggaactt tactattgag cacactatgg tttaaaccac catttctttc tgattttatt     300
gatggtgttt ttgctaaggt aaaaaatacc aaggttatta agatggtgt agtgtatagt      360
gagtttcctg ctataactat aggtagtact tttgtaaata catcctatag tgtggtagta     420
caaccacata ctactaattt agataataaa ttacaaggtc tcttagagat ctctgtttgc     480
cagtatacta tgtgcgatta cccacatacg atgtgtcatc ctaatctggg taataaacgc     540
atagaactat ggcattggga tacaggtgtt gttccctgtt tatataagcg taatttcaca     600
tatgatgtga atgctgatta tttgtattcc catttttatc aagaaggtgg tacttttttat    660
gcatattta cagacactgg tgttgttact aagtttctgt ttcatgttta tttaggcacg      720
gtgctttcac attattatgt catgcccttg acttgtaata gtgctatgac tttagaatac     780
tgggttacac ctctcacttt taaacaatat ttactcgctt tcaatcaaga tggtgttatt     840
tttaatgctg ttgattgtaa gagtgatttt atgagtgaga ttaagtgtaa aacactatct    900
atagcaccat ctactggtgt ttatgaatta aacggttaca ctgttcagcc aattgcagat     960
gtttaccgac gtatacctaa tcttcccgat tgtaatatag aggcttggct taatgataag    1020
tcggtgcctt ctccattaaa ttgggaacgt aagaccttt caaattgtaa ttttaatatg     1080
agcagcctga tgtcttttat ccaggctgac tcgtttactt gtaataatat tgatgctgct    1140
aagatatacg gtatgtgttt tttcagcata actatagata gtttgctat acccaatggt     1200
aggaaggttg acctacaaat gggcaatttg ggctatttgc agtctttta ctatagaatt     1260
gatactactg ctacaagttg tcagttgtat tataattac ctgctagtaa tgtttctatt     1320
agcaggttta atccttctat ttggaatagg agatttggtt ttacagaaca atctgttttt    1380
aagcctcaac ctgtaggtgt ttttactgat catgatgttg tttatgcaca acattgtttt    1440
aaagctccca caaatttctg tccgtgtaaa ttgaatgggt ctttgtgtgt aggtagtggt    1500
tttggtatag atgctggtta taaaaatagt ggtataggca cttgtcctgc aggtactaat    1560
tatttaactt gttataatgc taaccaatgt gattgtttgt gcactccaga ccctatttta    1620
tctaaatcta cagggcctta taagtgcccc caaactaaat acttagttgg cataggtgag    1680
cactgttctg gtcttgctat taaaagtgat tattgtggag caatccttg tacttgccaa    1740
ccaaaagcat ttttgggttg gtctgtggac tcttgtttac aaggggatag gtgtaatatt    1800
tttgctaatt ttatttgca tggtgttaat agtggtacta cttgttctac tgatttacaa    1860
aaatcaaaca cagacataat tcttggtgtt tgtgttaatt atgatcttta tggtattaca    1920
ggccaaggta ttttgttga ggttaatgcg acttattata atagttggca gaacctttta    1980
tatgattcta atggtaatct ctatggtttt agggactact aacaaacag aacttttatg    2040
attcgtagtt gctatagcgg tcgtgtttca gcgggctttc actctaactc ttccgaacca    2100
gcattgctat tcggaatat aaatgcaat tacgttttta ataatactct ttcacgacag     2160
ctgcaaccta ttaactattt tgatagttat cttggttgtg ttgtcaatgc tgataatagt    2220
```

FIGURE 3 (Page 2 of 2)

```
acttctagtt ctgttcaaac atgtgatctc acagtaggta gtggttactg gggggattac  2280
tctacacaaa gacgaagtcg tagaacgatt accactggtt atcggtttac taattttgag  2340
ccatttactg ttaatccagt aaatgatagt ttacaccctg taggtggttt gtatgaaatt  2400
caaatacctt cagagtttac tataggtaat atggaggagt ttattcaaac aagatctcct  2460
aaagttacta ttgattgtcc tgtttttgtc tgtggtgatt atgcagcatg taaatcacag  2520
ttggttgaat atggtagttt ttgtgacaat attaatgcta tactcacaga agtaaatgaa  2580
ctacttgaca ctacacagtt gcaagtagct aatagtttaa tgaatggtgt cactcttagc  2640
actaagctta aagatggctt taatttcaat gtagatgaca tcaattttc ccctgtatta  2700
ggttgtttag gaagcgaatg taataaagtt ccagtagat ctgctataga ggatttactt  2760
ttttctaaag taaagttatc tgatgttggt tttgttgatg cttataataa ttgtactgga  2820
ggtgccgaaa ttagggacct catttgtgtg caaagttata atggtatcaa agtgttgcct  2880
ccactgctct cagaaaatca gatcagtgga tacactttgg ctgccacctt tgctagtctg  2940
tttcctcctt ggtcagcagc agcaggcgta ccatttatt taaatgttca gtatcgtatt  3000
aatggtattg gtgttaccat ggatgtgcta actcaaaatc aaaagcttat ttctaatgca  3060
tttaacaatg cccttgatgc tattcaggaa gggtttgatg ctaccaattc tgctttagtt  3120
aaaattcaag ctgttgttaa tgcaaatgct gaagctctta ataacttatt gcaacaactc  3180
tctaataaat ttggtgctat aagtgcttct ttacaagaaa ttctatctag acttgatgct  3240
cttgaagcgc aagctcagat agacagactt atcaatgggc gtcttaccgc tcttaatgct  3300
tatgtttctc aacagcttag tgattctaca ctagtaaaat ttagtgcagc acaagctatg  3360
gagaaggtta atgaatgtgt caaaagccaa tcatctagga taaattttg tggtaatggt  3420
aatcatatta tatcattagt gcagaatgct ccatatggtt tgtattttat ccactttagc  3480
tatgtcccta ctaagtatgt cactgcgaag gttagtcccg gtctgtgcat ygcaggtgat  3540
agaggtatag ctcctaagag tggttatttt gttaatgtaa ataacacttg gatgttcact  3600
ggtagtggtt attactaccc tgaacctata actggaaata atgtggttgt tatgagtacc  3660
tgtgctgtta actatactaa agcaccggat gtaatgctga catttcaac acccaacctc  3720
cctgattta aggaagagtt ggatcaatgg tttaaaaacc aaacattaat ggcaccagat  3780
ttgtcacttg attatataaa tgttacattc ttggacctac aagatgaaat gaataggtta  3840
caggaggcaa taaagttt aaatcatagc tacatcaatc tcaaggacat tggtacatat  3900
gaatattatg taaaatggcc ttggtatgta tggcttttaa ttggccttgc tggcgtagct  3960
atgcttgttt tactattctt catatgctgt tgtacaggat gtgggactag ttgtttaag  4020
aaatgcggtg gttgttgtga tgattatact ggacatcagg agttagtaat caaaacgtca  4080
catgacgact aa                                                     4092
```

FIGURE 4

```
MFLILLISLP MAFAVIGDLK CTTVSINDVD TGAPSISTDV VDVTNGLGTY YVLDRVYLNT      60
TLLLNGYYPT SGSTYRNMAL KGTLLLSTLW FKPPFLSDFI DGVFAKVKNT KVIKDGVVYS    120
EFPAITIGST FVNTSYSVVV QPHTTNLDNK LQGLLEISVC QYTMCDYPHT MCHPNLGNKR    180
IELWHWDTGV VPCLYKRNFT YDVNADYLYS HFYQEGGTFY AYFTDTGVVT KFLFHVYLGT    240
VLSHYYVMPL TCNSAMTLEY WVTPLTFKQY LLAFNQDGVI FNAVDCKSDF MSEIKCKTLS    300
IAPSTGVYEL NGYTVQPIAD VYRRIPNLPD CNIEAWLNDK SVPSPLNWER KTFSNCNFNM    360
SSLMSFIQAD SFTCNNIDAA KIYGMCFFSI TIDKFAIPNG RKVDLQMGNL GYLQSFNYRI    420
DTTATSCQLY YNLPASNVSI SRFNPSIWNR RFGFTEQSVF KPQPVGVFTD HDVVYAQHCF    480
KAPTNFCPCK LNGSLCVGSG FGIDAGYKNS GIGTCPAGTN YLTCYNANQC DCLCTPDPIL    540
SKSTGPYKCP QTKYLVGIGE HCSGLAIKSD YCGGNPCTCQ PKAFLGWSVD SCLQGDRCNI    600
FANFILHGVN SGTTCSTDLQ KSNTDIILGV CVNYDLYGIT GQGIFVEVNA TYYNSWQNLL    660
YDSNGNLYGF RDYLTNRTFM IRSCYSGRVS AGFHSNSSEP ALLFRNIKCN YVFNNTLSRQ    720
LQPINYFDSY LGCVVNADNS TSSSVQTCDL TVGSGYWGDY STQRRSRRTI TTGYRFTNFE    780
PFTVNPVNDS LHPVGGLYEI QIPSEFTIGN MEEFIQTRSP KVTIDCPVFV CGDYAACKSQ    840
LVEYGSFCDN INAILTEVNE LLDTTQLQVA NSLMNGVTLS TKLKDGFNFN VDDINFSPVL    900
GCLGSECNKV SSRSAIEDLL FSKVKLSDVG FVDAYNNCTG GAEIRDLICV QSYNGIKVLP    960
PLLSENQISG YTLAATFASL FPPWSAAAGV PFYLNVQYRI NGIGVTMDVL TQNQKLISNA   1020
FNNALDAIQE GFDATNSALV KIQAVVNANA EALNNLLQQL SNKFGAISAS LQEILSRLDA   1080
LEAQAQIDRL INGRLTALNA YVSQQLSDST LVKFSAAQAM EKVNECVKSQ SSRINFCGNG   1140
NHIISLVQNA PYGLYFIHFS YVPTKYVTAK VSPGLCIAGD RGIAPKSGYF VNVNNTWMFT   1200
GSGYYYPEPI TGNNVVVMST CAVNYTKAPD VMLNISTPNL PDFKEELDQW FKNQTLMAPD   1260
LSLDYINVTF LDLQDEMNRL QEAIKVLNHS YINLKDIGTY EYYVKWPWYV WLLIGLAGVA   1320
MLVLLFFICC CTGCGTSCFK KCGGCCDDYT GHQELVIKTS HDD                    1363
```

FIGURE 6

```
T101  CTCAGATGAATTTGAAATATGCTATTAGTGCTAAGAATAGAGCCCGCACTGTTGCTGGTG
BCV   CTCAAATGAATTTGAAATATGCTATTAGTGCTAAGAATAGAGCCCGCACTGTTGCTGGTG
OC43  CTCAAATGAATTTGAAATATGCTATTAGTGCTAAGAATAGAGCCCGCACTGTTGCTGGTG
HEV   CTCAAATGAATTTGAAATATGCTATTAGTGCCAAGAATAGAGCCCGCACTGTTGCTGGTG
CCV   CTCAGATGAATTTGAAATATGCTATTTCTGGAAAGGCTAGAGCTCGTACAGTAGGAGGAG
      **** ********************  * ***  ****** ** ** ** *  ** *

T101  TTTCCATACTTAGTACTATGACTGGCAGAATGTTTCATCAAAAATGTTTGAAAAGTATAG
BCV   TTTCCATACTCAGTACTATGACTGGCAGAATGTTTCATCAAAAATGTTTGAAAAGTATAG
OC43  TTTCCATACTTAGTACTATGACTGGCAGAATGTTTCATCAAAAATGTTTGAAAAGTATAG
HEV   TTTCCATACTTAGTACTATGACTGGCAGAATGTTTCATCAAAAATGCTTGAAAAGTATAG
CCV   TTTCACTTCTTTCTACCATGACTACGAGACAATACCACCAGAAGCATTTGAAGTCAATTG
      ****  * **   *** ******    ***    *  ** ** **    *****   ** *

T101  CAGCTACACGTGGTGTTCCTGTTGTTATAGGCACCACTAAATTTTATGGCGGCTGGGATG
BCV   CAGCTACACGTGGTGTTCCTGTTGTTATAGGCACCACTAAGTTTTATGGCGGCTGGGATG
OC43  CAGCTACACGTGGTGTTCCTGTAGTTATAGGCACCACTAAATTTTATGGTGGCTGGGATG
HEV   CAGCTACACGTGGCGTTCCTGTGGTTATAGGCACCACTAAATTTTATGGCGGCTGGGATG
CCV   CTGCAACACGCAATGCCACTGTGGTTATTGGCTCAACCAAGTTTTATGGTGGTTGGGATA
      * ** *****        * *** **** ***  * ** ** ********  ** ******

T101  ATATGTTACGTCGCCTTATTAAAGATGTTGACAATCCTGTACTTATGGGTTGGGATTATC
BCV   ATATGTTACGTCGCCTTATTAAAGATGTTGATAATCCTGTACTTATGGGTTGGGATTATC
OC43  ATATGTTACGCCGCCTTATTAAAGATGTTGACAATCCTGTACTTATGGGTTGGGATTATC
HEV   ATATGTTACGCCGCCTTATTAAAGATGTTGATAATCCTGTACTTATGGGTTGGGATTATC
CCV   ACATGCTTAAAAATTTAATGCGTGATGTTGATAATGGTTGTTTGATGGGATGGGACTATC
      * ***  *       * **       * ******* ***   * ***** ***** ****

T101  CTAAGTGTGA
BCV   CTAAGTGTGA
OC43  CTAAGTGTGA
HEV   CAAAGTGTGA
CCV   CTAAGTGTGA
      * ********
```

FIGURE 7

```
protHCVpoly    ---MNLKYAISAKNRARTVAGVSILSTMTGRMFHQKCLKSIAATR
protHEVpoly    ---MNLKYAISAKNRARTVAGVSILSTMTGRMFHQKCLKSIAATR
protBCVpoly    ---MNLKYAISAKNRARTVAGVSILSTMTGRMFHQKCLKSIAATR
protCRCVpol    --QMNLKYAISAKNRARTVAGVSILSTMTGRMFHQKCLKSIAATR
protCECVpol    MTQMNLKYAISGKARARTVGGVSLLSTMTTRQYHQKHLKSIAATR
                  ********.* ***.*:***** * :* ****** protHCVpoly    GVPVVIGTTKFYGGWDDMLRRLIKDVDNPVLMGWDYPKC
protHEVpoly    GVPVVIGTTKFYGGWDDMLRRLIKDVDNPVLMGWDYPKC
protBCVpoly    GVPVVIGTTKFYGGWDDMLRRLIKDVDNPVLMGWDYPKC
protCRCVpol    GVPVVIGTTKFYGGWDDMLRRLIKDVENPVLMGWDYPKC--
protCECVpol    NATVVIGSTKFYGGWDNMLKNLMRDVDNGCLMGWDYPKC---
               ...****:********:**:.*::**:*  ********
```

FIGURE 8 (Page 1 of 9)

```
CRCVspike    --------------------ATGTTTTTGATACTTTTA------ATTTCCTTACCAATG
CECVspike    ATGATTGTGCTCGTAACTTGCATTTTATTGTTATGTTCATACCACACTGCTTCGAGTACG
                             ** ** *** ** ** *      * * * *       * *

CRCVspike    GCTTTTGCTG-TTATAGGAGATTTAAAGTGTACTACGGTTTC-CATCAATGATGTTGACA
CECVspike    TCAAATAATGATTGTAGACAAGTTAA--CGTAACACAATTAGATGGCAATGAAAACCTCA
              *   *  ** ** *** * ****   *** ** **        ******         **

CRCVspike    CCGGTG-CTCCTTCTATTAGCACTGATGTTGTCGATGTTACTAATGGTTTAGGTACTTAT
CECVspike    TTAGAGACTTTTTGTTTCAAAACTT-TAAAGAAGAAGGAACTGTAGTTGTTGGTGGTTAC
              * ** ** * * **  *    *  *  ** *  ***    * * ***  ***

CRCVspike    TATGTTTTAGA----TCGTGTG--TATTTAAATACTACA----TTGTTGCTTAATGGTTA
CECVspike    TACCCTACAGAGGTTTGGTATAACTGTTCTAGAACAGCAACAACTACTGCCTA-TGAGTA
             **   *  ***    *  **  *  * **  *  ** **    *  *** ** **  **

CRCVspike    TTATCCTACTTCAGGTTCTACATATCGTAATATGGCA-CTGAAGGGAACTTTACTATTGA
CECVspike    TTTCAGTAATATACACGCATTCTATTTTGATATGGAAGCCATGGAGAATAGTACTGGTAA
              **   ** * *   *    *** * ****** *  *  ***   **** * *

CRCVspike    -GCACACTATGG-TTTAAACCACCATTTCTTTCTGATTTTATTGATGGTGTTTTTGCTAA
CECVspike    TGCACGTGGTAAACCTTTATTATTTCATGTTCATGGTGAGCCTGTTAGTGTCATCATATA
              ****    *       *  *   *     ** **   ** * ****   *         *

CRCVspike    GGTAAAAAATACCAAGGTTATTAAAGATGGTGTAGTGTATAG---TGAGTTTCCTGCTAT
CECVspike    CATATCTTATAGAGATGATGTGCAACATAGGCCACTTTTAAAACACGGATTAGTGTGCAT
              **    ***  *   *   ** ** *    * * *     *     * **        **

CRCVspike    AACTATAGGTAGTACTTTTG--TA-AATACATCCTATAGTGTGGTAGTACAACCACATAC
CECVspike    AACTGAAAGTCGCAACATTGACTATAACAGTTTCACCAGTA-GCCAGTGGAATTCCATAT
             ****  *  **  *  ***  *** ** ** **  *  ***  *  *** ** ** ****

CRCVspike    -TACTAATTTAGATAATAAATTACAAGGTCTCTTAGAGATCTCTGTTTGCCAGTATACTA
CECVspike    GTACGGGTAATGACAGAAAAATTCCTT-TCTCTGTCATACCCACGGACAATGGAACAAAA
              ***   *  ** ** *** **    *****   *     *    *        *  * *
```

FIGURE 8 (Page 2 of 9)

```
CRCVspike   -TGTGCGATTACCCACATA-CGATGTGTC-ATCCTAATCTGGGT-AATAAACG--CATAG
CECVspike   ATTTATGGTCTTGAGTGGAATGATGAATTTGTTACAGCGTACATTAGTGGTCGTTCTTAT
             *  *  * *         * ****  *   *    *    * *  * **   *  **

CRCVspike   AACTATGGCATTGGGATACAGGTGTTGTTCCCTGTT-TATATAAGCGTAATTTCACATAT
CECVspike   AATTGGAACATCAATAATAATTGGTTTAACAATGTCACGCTTCTGTATAGTCGCTCAAGC
            ** *   ***    *   *   ***   *  ***    *   *   ** *   * **

CRCVspike   GATGTGA-ATGCTGATTATTTGTATTCCCATTTTTATCAAGAAGGTGGTACTTT---TTA
CECVspike   ACTGCCACATGGCAACACAGTGC-TGCATACGTTTACCAAGGTGTTTCTAACTTCACTTA
             *  *  * *** *        *  **  * *   *  ****  **    * * **   ***

CRCVspike   TGCATATTTTACAGACACTGGTGTTGTTACTAAGTTTCTGTTTCATGTTTAT-TTAGGCA
CECVspike   TTACAAGTTAAATAACACCAATGGTCTAA--AAACCTATGAATTATGTGAAGATTATGAA
             *   * **  *  ****   **  *  *  **    *   * ****    *   *** * *

CRCVspike   CGGTGCTTT---CACATTATTA-TGTCATGCCCTTGACTTGTAATAGTGCTATGACTTTA
CECVspike   TATTGCACTGGCTACGCCACTAACATCTTTGCCCCAACTGTGGGAGGTTACATACCTGAT
               ***   *    **   *  **    *  ** ***   **    **   **  **  **

CRCVspike   GAATACTGGGTTA-----CACCTCTCACTTTTAAACAATATTTACTCGCTTTCAATCAAG
CECVspike   GGATTAGTTTTAACAATTGGTTTTTGCTTACAAACAGCTCCACTTTTGTTAGTGGCAGA
            *  **    *    ***         *    *   * ***  *****      *   **       **

CRCVspike   ATGGTGTTATTTTTAATGCTGTTGATTGTAAGAGTGATTTTATGAGTGAGATTAAGTGT-
CECVspike   TTTGTAACAAATCAACCATTATTAGTTAATTGCTTGTGGCCAGTTCCTAGTTTTGGTGTT
              *  **   *    *  *    * **  **    *      *    *       **  **   ****

CRCVspike   --AAAACACTATCTATAGCACCATCTACTGGTGTTTATGAATTAAACGGTTACACTGTTC
CECVspike   GCAGCACAAGAATTTTGTTTTGAAGGTGCACAGTTTAGCCAATGTAATGGTGTGTTTTA
              *   *** *  * *   *        *****  *  *  *  * *           * **

CRCVspike   AGCCA-ATTGCAGATGTTTACCGACGTATACCTAATCTTCCCG--ATTGTAATATAGAGG
CECVspike   AATAACACAGTAGATGTCATTAGATTCAACCTTAATTTTACTGCAGATGTACAATCTGGC
             *   *   *  ******   **     *    ** ** *  *     ****  **      *
```

FIGURE 8 (Page 3 of 9)

```
CRCVspike    CTTGGCTTAATGATAAGT-CGGTGCCTTCTCCATTAAATTGGGAACGTAAGACCTTTTCA
CECVspike    ATGGGTGCTACAGTATTTTCACTGAATACAACAGGTGGTTGCATTCTTGAGATTTCTT--
              * **     *  **  * *  **   * *  **      ***    *  *  ***   *  **

CRCVspike    AATTGTAATTTTAATATGAGCAGCCTGATGTCTTTTATCCAGGCTGACTCGTTTACTTGT
CECVspike    -GTTATAATGATATAGTGAGCGAGTCAAGTTTCTACAGTTATGGTGA---AATTCCCTTC
              ** ****  **   ***** *     *  *  *  *  * * ***      ** *  *

CRCVspike    AATAATATTGATGCTGCTAAGATATACGGTATGTGTTTTTTCA--GCATAACTATAGATA
CECVspike    GGCGTAACTGATGG-ACCGCGTTAT-TGTTATGTCCTCTATAATGGCACAGCTCTTAAGT
              *  *****  *   *   *  ***  * ***** *  * * *   *** *  **  *  *

CRCVspike    AGTTTGCTA---TACCCAATGGTAGGAAGGTTGACCTACAAATGGGCAATTTGGGCTATT
CECVspike    ATTTCGGCACATTACCCCCTAGTGTCAAGG--AAATTGCTATTAG-TAAGTGGGGCCAAT
              * **  *  *   *****  * **  ****    *   *  * * *   **  **** *  *

CRCVspike    TGCAGTCTTTTAACTATAGAATTGATACTACTGCTACAAGTTGTCAGTTGTATTATAATT
CECVspike    TTTATATTAATGGTTACAATTTCTTTAGCACTTTTCCTATTGATTGTATATCTTTTAACT
              *  *  *  *   **  *  *  ** ***  * *   *     *  * ** ***   *

CRCVspike    TACCTGCTAGTAATGTTTCTATTAGCAGGTTTAATCCTTCTATTTGGAATA--GGAGATT
CECVspike    TAACCACTGGTGATAGTGGAGCATTTTGGACAATTGCTTACACATCGTACACTGAAGCAT
              ** *  **  ** **   *         **  *   *  ***   *  *  *  * **   *

CRCVspike    TGGTTTTA-CAGAACAATCTGTTTTTAAGCCT-CAACCTGTAGGTGTTTTTACTGATCAT
CECVspike    TAGTACAAGTTGAAAACACAGCCATTAAAAAGGTGACGTATTGTAACAGTCAC-ATTAAT
              * **   *   ***  *   *   *  ****      **  * **      *  ** *  **

CRCVspike    GATGTTGTTTATGCACAACATTGTTTTAAAGCTCCCACAAATTTCTGTCCG-----TGTA
CECVspike    AACATCAAATGTTCTCAACTTACTGCTAATTTGCAAAATGGCTTTTATCCTGTTGCTTCA
              *  *     *  *   ****  *    *      ***       *  *  ***          *  *

CRCVspike    AATTGAATGGGTCTTTGTGTGTAGGTAGTGGTTTTGGTA--TAGATGCTGGTTATAAA--
CECVspike    AGTGAAGTTGGTCTTGTCAATAAGAGTGTTGTTACTACCTAGTTTCTATTCACATACC
               *  *    * * *****       **   **  **  **  ***  *  *   *  ****
```

FIGURE 8 (Page 4 of 9)

```
CRCVspike       AATAGTGGTATAGGCACTTGTCCTGCAGGTACTAATTATTTAACTTGTTATAATGCTAAC
CECVspike       AGTGTTAATATAACTATTGATCTTG---GTATGAAGCGTAGTGGTTATGGTCAACCCA--
                *  *  *  ****    *  *  ** **    *** **    *     ** *  *  * *  *

CRCVspike       CAATGTGATTGTTTGTGCACTCCAGAC--CCTATTTTATCTAAATCTACAGGGCCTTA-T
CECVspike       TAGCCTCAACACTAAGTAACATCACACTACCAATGCAGGATAATAACACCGATGTGTACT
                 *   *  *     *       **   ** **   **   ***      ** *     ** *

CRCVspike       AAGTGCCCCCAAACTAAATACTTAGTTGGCATAGGTGAGCACTGTTCTGGTCTTGCTATT
CECVspike       GTATTCGTTCTAACCAATT-CTCAGTTTATGTTCACTCCACTTGCAAAAGTTCTTTATGG
                 *  *      *  ***  ** *  ** ****     *           **       ** *

CRCVspike       AAAAGTGATTATTGTGGAGGCAATCCTTGTACTTGCCAACCAAAAGCATTTTTGGG--TT
CECVspike       GACAACAATTTTAATCAAGATTGCACAGATGTTTTATATGCCACAGCTGTTATAAAAACT
                 *  *    *** **  *  **    *    *    **   *  * *  ***  ** *         *

CRCVspike       GGTCTGTGGAC--TCTTGTTTACAAGG--GGATAGGTGTAATATTTTTGCTAA-TTTTAT
CECVspike       GGTACTTGCCCCTTCTCATTTGATAAATTGAATAATTACTTAACTTTTAACAAGCTTTGT
                ***     **    *  ***   ***       *   * ***   *     * ****    **  *** *

CRCVspike       TTTGCATGGTGT--TAATAGTG------GTACTACTTGTTCTACTGATT-TACAAAAATC
CECVspike       TTGTCGTTGAATCCTACTGGTGCCAACTGTAAGTTTGATGTTGCTGCCCGTACAAGAACC
                **   *    *  *     **  *  ***           ***      *    *  *  ***       ***** ** *

CRCVspike       AAACACAGACATAATTCTTGGTGTTTGTGTTAATTATGATCTTTATGGTATTACAGGCCA
CECVspike       AA-TGAGCAGGTTGTTAGAAGTTTATATGTAATATATGAAGAAGGAGACAACATAGTGGG
                **         *  *   **      ** *  *  ***  *  *****          *   *  *   **

CRCVspike       AGGTATTTTTGTTGA----GGTTAATGCGACTTATTATAATAGTTGGCAGAACCTTTTAT
CECVspike       TGTACCGTCTGATAATAGTGGTCTTCACGATTTGTCAGTGTTACACTTAGACTCCTGTAC
                  *     * ** *  *     ***    ***  ** * *     *         *** *   **

CRCVspike       ATGATTCTAATG---GTAATCTCTATGGTTTTAGGGACTACTTAACAAACAGA-ACTTTT
CECVspike       A-GATTACAATATATATGGTAGAACTGGTGTT-GGTATTATTAGACAAACTAACAGCACA
                * ****  ***       *  *    **** ** **  * ** *   ****** *  *
```

FIGURE 8 (Page 5 of 9)

```
CRCVspike    ATGATTCGTAGTTGCTATAGCG-GTCGTGTTTCAGCGGGCTTTCA---CTCTAACTCTTC
CECVspike    ATACTTAGTGGCTTACATTATACATCACTATCAGGTGATTTATTAGGTTTTAAAAATGTT
             ** **.** * *   **      **      *    * *   * * *   * **    *

CRCVspike    CGAACCAGCATTG-CTATTTCGGAATATTAAATGCAATTACGTTTTTAATAATACTCTTT
CECVspike    AGTGATGGTGTTGTCTATTCTGTGACACCATGTGATGTAAGCGCACAAGCGGCTGTTATT
              *     *  *** *****'* * *   *  **  * *        *      *  **

CRCVspike    CACG-----ACAGCTGCAACCTATTAACTATTTTGATAGTTATCTTGGTTGTGTTGTCAA
CECVspike    GATGGGGCCATAGTTGGAGC-TATGACTTCCATTAATAGTGAACT-GTTAGGTCTAACAC
             * *      *  ** ** * *** * *  ** ****  * ** *  *   *    * **

CRCVspike    TGCTGATAATAGTAC-----TTCTAGTTCTGTTCAAACATGTGATCTCACAGTAGGTAGT
CECVspike    ATTGGACAACAACACCAAATTTTTATTACTACTCTA-TATATAAT---ACAACAAATGAG
                ** ** * **     ** ** *  **  ** *   ** * **   *** *  *

CRCVspike    GGTTACTGGGGGGATTACTCTACACAAAGACGAAGT----CGTAGAACGATTACCACTGG
CECVspike    AGA-ACTCGTGGCACTGCAATCGACAGTAACGATGTAGATTGTGAACCTATCATAACCTA
              *  ***  *  **  *  * * *    *  *** *    *   * *  *** *   **

CRCVspike    TT-----ATCGGTTT----ACTAATTTTGAGCCATTTACTGTTAATCCAGTAAATGATAG
CECVspike    TTCTAACATAGGTGTTTGTAAAAATGGTGCGTTGGTTTTTATTAACGTCACACATTCTGA
             **      ** *** *    * ***  **  **  * **** * **     *  **   *

CRCVspike    TTTACACCCTGTAGGTGGTTTGTAT--GAAAT-TCA-AATACCTTCAGAGTTTACTATAG
CECVspike    TGGAGATGTT-CAACCAATTAGCACTGGCAATGTCACGATACCCACAAACTTTACCATAT
             *  *  *   *    *     **  *    * *** *** ** **  ** **** *** ***

CRCVspike    GTAATATGGAGGAGTTTATTCAAACAAGATCTCCTAAAGTTACTATTGATTGTCCTGTTT
CECVspike    CTGTGCAAGTTGAATACATCCAGGTTTACACTACACCGGTGTCAATAGATTGTTCTAGAT
              *     *  ** *   * **  **       *    *  ** **  ** ****** *   *

CRCVspike    TTGTCTGTGGTGATTATGCAGCATGTAAATCACAGTTGGTTGAATATGGTAGTTTTTGTG
CECVspike    ACGTTTGTAATGGTAACCCTAGATGTAATAAATTGTTAACACAATATGTTTCTGCATGTC
              *** ***  * * *    *  ****** *    ***       ******* *   ***
```

FIGURE 8 (Page 6 of 9)

```
CRCVspike    ACAATATTAATGCTATACTCACAG-AAGT----------AAATGAACTACTTGACACTA
CECVspike    AAACTATTGAGCAAGCGCTTGCAATGAGTGCCAGCCTTGAAAACATGGAAGTTGATTCCA
             *  * ****  *       **  **   ***           ***   * ****   * *

CRCVspike    CACAGTTGCAAGTAGCTAATAGTTTAATGAATGGTGTCACTCTTAGCACTAAGCTTAAAG
CECVspike    TGTTGTTTGTTTCAGAAAATGCCCTTA-AATTGGCATCTGTTGAGGCGTTCAATAGTACA
                ***      **  ***     * *  * ***  **  *   **  * *       *

CRCVspike    ATGGCTTTAATTTCAATGTAGATGACAT----CAATTT---TTCCCCTGTATTAGGTTGT
CECVspike    GAACATTTAGATCCTATTTACAAAGAATGGCCTAACATAGGTGGTTCTTGGCTAGGAGGT
                 ****  *  * **  **  *       **     *    **    **** **

CRCVspike    TTAGGAAGCGAAT----------GTAATAA-AGTTTCCAGTA--GATCTGCTATAGAGGAT
CECVspike    CTAAAAGACATACTTCCGTCCCATAATAGCAAACGTAAGTATCGTTCTGCTATAGAAGAC
              **  *  *   *           *****  *      ****   *  *********** **

CRCVspike    TTACTTTTTTCTAAAGTAAAGTTATCTGATGTTGGTTTTGTTGATGC---TTATAATAAT
CECVspike    TTGCTTTTTGATAAAGTTGTAACTTCTGGTCTAGGTACAGTTGATGAAGATTATAAACGT
             ** ******  ******      **** * *  ***   ******      ******  *

CRCVspike    TGTACTGGAGGTGCCGAAATTAGGGACCTCATTTGTGTGCAAAGTTATAATGGTATCAAA
CECVspike    TGTACAGGTGGTTATGACATAGCTGACTTAGTTTGTGCACAATATTACAATGGCATCATG
             ***** **  ***   ** **  ** ** * ****** **   * *** ***** ****

CRCVspike    GTGTTGCCTC-CACTGCTCTCAGAAAATCAGATCAGTGGATACACTTTGGCTGCCACCTT
CECVspike    GTTCTACCTGGTGTTGCTAAT-GATGACAAGATGACTATGTACACAGCCTCTCTTGCAGG
             **  * ***      ****  **  *   **** * ***  *****   **    *

CRCVspike    TGCTAGTCTGTTTCCTCC-TTGGTCAGCAGCA--GCAGGCGTACCATTTTATTTAAATGT
CECVspike    TGGTATAGCATTAGGTGCACTAGGTGGTGGCGCCGTGGCTATACCTTTTGCAGTAGCAGT
             ** **   *   ** *   * *  * ** **   * *  * ****  *   ** **

CRCVspike    TCAGTATCGTATTAATGGTATTGGTGTTACCATGGATGTGCTAACTCAAAATCAAAAGCT
CECVspike    TCAGGCTAGACTTAATTATGTTGCTCTACAAACTGATGTATTGAACAAAAACCAGCAGAT
             ****   *  * ***     * *  *     * ***** *    *  ** ** **  * *
```

FIGURE 8 (Page 7 of 9)

```
CRCVspike    TATTTCTAATGCATTTAACAATGCCCTTGATGCTATT---------CAGGAAGGGTT--
CECVspike    CCTGGCTAATGCTTTCAACCAAGCTATTGGTAACATTACACAGGCATTTGGTAAGGTTAA
              *  ******* ** *** * **  *** *   ***           ** * ****

CRCVspike    TGATGCTA----------------------CCAATTCTGCT------TTAGTTAAAAT
CECVspike    TGATGCTATACATCAAACATCACAAGGTCTTGCCACTGTTGCTAAAGCATTGGCAAAAGT
             ********                      *** * ****      ** * *** *

CRCVspike    TCAAGCTGTTGTTAATGCAAATGCTGAAGCTCTTAATAACTTATTGCAACAACTCTCTAA
CECVspike    GCAAGATGTTGTTAACACACAAGGGCAAGCTTTAAGCCACCTAACAGTACAACTGCAAAA
              **** *********  ** *  *    ***** *     ** **      *****  **

CRCVspike    TAAATTTGGTGCTATAAGTGCTTCTTTACAAGAAATTCTATCTAGACTTGATGCTCTTGA
CECVspike    TAGCTTCCAAGCCATTAGTAGTTCTATTAGTGACATTTATAATAGGCTTGATGAACTGAG
             **   **    ** ** ** *** ****  *  ** ***    *** ******* **

CRCVspike    AGCGCAAGCTCAGATAGACAGACTTATCAATGGGCGTCTTACCGCTCTTAATGCTTATGT
CECVspike    TGCTGATGCACAAGTTGATAGGCTGATTACAGGTAGACTTACAGCACTTAATGCATTTGT
              **   * **  ** ** ** ** ** ** **  * ***** ** ******** * ***

CRCVspike    TTCTCAACAGCTTAGTGATTCTACACTAGTAAAATTTAGTGCAGCACAAGCTATGGAGAA
CECVspike    ATCTCAGACTCTAACCAGACAAGCGGAGGTTAGGGCTAGTAGACAACTTGCCAAAGACAA
             *****    ** **  *   **  ** *  ****    ** *   **  **  **

CRCVspike    GGTTAATGAATGTGTCAAAAGCCAATCATCTAGGATAAATTTTTGTGGTAATGGTAATCA
CECVspike    GGTTAATGAATGTGTTAGGTCTCAGTCTCAGAGATTTGGATTTTGTGGTAATGGTACACA
             ***************  *  **  **    * *    ***************    **

CRCVspike    TATTATATCATTAGTGCAGAATGCTCCATATGGTTTGTATTTTATCCACTTTA-GCTATG
CECVspike    TTTGTTTTCACTTGCAAATGCAGCACCAAATGGCATGGTTTTCTTTCACACAGTGCTAT-
             * *  * *** * * **  * *    **  *** **** *** ****** *   *****

CRCVspike    TCCCTACTAAGTATGTCACTGCGAAGGTTAGTCCCGGTCTGTGCATYGCAGGTGATAGAG
CECVspike    TACCAACAGCTTATGAAACTGTAACAGCTTGGTCAGGTATTTGTGCTTCAGATGGCGATC
             * ** **  ****    **** *   * *    *  *  * *** *    *** **
```

FIGURE 8 (Page 8 of 9)

```
CRCVspike      GTA---------TAGCTCCTAAGAGTGGTTATTT-----TGTT----AATGTAAATAACA
CECVspike      GCACTTTTGGACTTGTCGTTAAAGATGTTCAGTTGACGTTGTTTCGTAATCTAGATGACA
                * *         * *    ***   ** * * **        ****    *** ** ** ***

CRCVspike      CTTGGATGTTCACTGGTAGTGGTTATTACTACCCTGAACCTATAACTGGAAATAATGTGG
CECVspike      AGTTCTATTTGACTCCCAGAACTATGTATCAGCCTAGAGCTGCAACTAGTTCTGATTTTG
                 *    ** ***  **   *   ** * *** * **  **** *  * ** * *

CRCVspike      TTGTTATGAGTACCTGTGCTGTTAACTATACTAAAGCACCGGATGTAATGCTGAACATTT
CECVspike      TTCAGATTGAGGGGTGCGACGTGTTGTTTGTCAATGCAACTGTAATTGACTTGCCTAGTA
               **    **     ** *  **    * *   ** *** * *    *     **    * *

CRCVspike      CAACACCCAACCTCCCTGATTTTAAGGAAG-------AGTTGGATCAATGGTTTAAAAAC
CECVspike      TTATACCTGACTATATCGACATTAATCAGACTGTTCAAGACATATTAGAAAACTACAGAC
                * *** **       **  ****  *        **    ** *     ** * **

CRCVspike      CAAACATTAATGGCACCAGATTTGTCACTTGATTATATAAATGTTACATTCTTGGACCTA
CECVspike      CAAAC-TGGACTGTACCTGAATTGACAATTGACATTTTTAACGCAACCTATTTAAATCTG
               ***** *  *  *  * *** ** *** **  ****    * ** * ** *  * **

CRCVspike      CAAGATGAAATGAATAGGTTACAGG--AGGCAATAAAAGTT---TTAAATCATAGC----
CECVspike      ACTGGTGAAATTGATGACTTAGAATTTAGGTCAGAAAAGCTACATAACACCACAGTAGAG
                  * ******  **  *** *    ***   * ***** *   *  * ** **

CRCVspike      ------------------------------TACAT----CAATCTCAAGGACATTGGTACA
CECVspike      CTTGCCATTCTCATTGACAATATTAACAATACATTAGTCAATCTTGAATGGCTCAATAGA
                                              *****     ******  *    * ** *

CRCVspike      TATGAATATTATGTAAAATGGCCTTGGTATGTATGGCTTTTAATTGGCCTTGCTGGCGTA
CECVspike      ATTGAAACTTATGTGAAATGGCCTTGGTATGTGTGGCTACTAATAGGC-TTAGTAGTAGT
                ****  ****** ******************* *****  **** ***** ** * *

CRCVspike      GCTATGCTTGTT-TTACTATTCTTCATATGCTGTTGTACAGGATG---TGGGACTAGTTG
CECVspike      GTTTTGCATACCGCTATTGCTATTTTGCTGTTGTAGTACAGGTTGCTGTGGATGCATAGG
                * * *** *    ** * **  * *  ** *** ****** **   ***     *
```

FIGURE 8 (Page 9 of 9)

```
CRCVspike    TTTTAAGAAATGCGGTGGTTGTTGTGATGATTATACTGGACA--TCAGGAGTTAGTAATC
CECVspike    TTGTTTGGGAAGTTGTTGTCATTCTATTTGTAGTAGAAGACAATTTGAAAATTACGAACC
             ** *  *  * *  ** **  ** *  *  * **    ****  *   * *** ** *

CRCVspike    AA----AACGTCACATGACGACTAA-----------------------------------
CECVspike    AATTGAAAAAGTGCATGTCCACTAAA----------------------------------
             **    **    **** * *****
```

FIGURE 9 (Page 1 of 12)

```
BCVspike              ATGTTTTTGATACTTTTAATTTCCTTACCAATGGCTCTTGCTGTTATAG
HCVspike   -----------ATGTTTTTGATACTTTTAATTTCCTTACCAACGGCTTTTGCTGTTATAG
CRCVspike  -----------ATGTTTTTGATACTTTTAATTTCCTTACCAATGGCTTTTGCTGTTATAG
HEVspike   -------    ATGTTTTTTATACTTTTAATCACCCTGCCTTCTGTTTTTGCAGTTATAG
                      *******  *********** **  *  **      * * ****  ******

BCVspike   GAGATTTAAAGTGTACTACGGTTTCCATTAATGATGTTGACACCGGTGTTCCTTCTGTTA
HCVspike   GAGATTTAAAGTGTACTACGGTTTCCATTAATGATATTGACACCGGTGCTCCTTCTATTA
CRCVspike  GAGATTTAAAGTGTACTACGGTTTCCATCAATGATGTTGACACCGGTGCTCCTTCTATTA
HEVspike   GGGATTTAAAGTGTAATACTTCATCAATTAATGACGTTGACACTGGTGTGCCATCTATTA
           * *************  ***    ** ** *****  ****** **** **  *** ***

BCVspike   GCACTGATACTGTCGATGTTACTAATGGTTTAGGTACTTATTATGTTTTAGATCGTGTGT
HCVspike   GCACTGATATTGTCGATGTTACTAATGGTTTAGGTACTTATTATGTTTTAGATCGTGTGT
CRCVspike  GCACTGATGTTGTCGATGTTACTAATGGTTTAGGTACTTATTATGTTTTAGATCGTGTGT
HEVspike   GCTCTGAAGTTGTTGATGTCACTAATGGTTTGGGGACTTTCTATGTTTTAGATCGTGTCT
           ** ****    *** ***** **********  ** ****  **************** *

BCVspike   ATTTAAATACTACGTTGTTGCTTAATGGTTACTACCCTACTTCAGGTTCTACATATCGTA
HCVspike   ATTTAAATACTACGTTGTTGCTTAATGGTTACTACCCTACTTCAGGTTCTACATATCGTA
CRCVspike  ATTTAAATACTACATTGTTGCTTAATGGTTATTATCCTACTTCAGGTTCTACATATCGTA
HEVspike   ATTTAAATACCACATTGTTGCTCAATGGTTATTACCCAATTTCAGGTGCTACATTTCGTA
           **********  ** ******* ******** ** **  **  ******  ****** *****

BCVspike   ATATGGCACTGAAGGGAACTTTACTATTGAGCACACTATGGTTTAAACCACCTTTTCTTT
HCVspike   ATATGGCACTGAAGGGAACTTTACTATTGAGCAGACTATGGTTTAAACCACCTTTTCTTT
CRCVspike  ATATGGCACTGAAGGGAACTTTACTATTGAGCACACTATGGTTTAAACCACCATTTCTTT
HEVspike   ATGTGGCTCTGAAAGGAACTCGATTATTGAGCACCTTGTGGTTTAAGCCGCCTTTTTTAT
           ** ****  *****  ***** *  *********    * ******** **  ** * *

BCVspike   CTGATTTTATTAATGGTATTTTTGCTAAGGTCAAAAATACCAAGGTTATTAAAAATGGTG
HCVspike   CTGATTTTATTAATGGTATTTTTGCTAAGGTCAAAAATACCAAGGTTATTAAAAAGGGTG
CRCVspike  CTGATTTTATTGATGGTGTTTTTGCTAAGGTAAAAAATACCAAGGTTATTAAAGATGGTG
HEVspike   CACCTTTTAATGATGGTATTTTTGCCAAGGTTAAAAACAGCAGATTTTCTAAACATGGTG
           *     *****  * ***** ******* ***** *****  **   **  **** ****
```

FIGURE 9 (Page 2 of 12)

```
BCVspike    TAATGTATAGTGAGTTTCCTGCTATAACTATAGGTAGTACTTTTGTAAATACATCCTATA
HCVspike    TAATGTATAGTGAGTTTCCTGCTATAACTATAGGTAGTACTTTTGTAAATACATCCTATA
CRCVspike   TAGTGTATAGTGAGTTTCCTGCTATAACTATAGGTAGTACTTTTGTAAATACATCCTATA
HEVspike    TTATTTATAGTGAGTTTCCTGCTATTACTATAGGTAGTACTTTTGTAAATACTTCCTATA
             *  ******************* ************************** ******

BCVspike    GTGTGGTAGTACAACCACATACTACCAATTTAGATAATAAATTACAAGGTCTCTTAGAGA
HCVspike    GTGTGGTAGTACAACCACATACTACCAATTTGGATAATAAATTACAAGGTCTCTTAGAGA
CRCVspike   GTGTGGTAGTACAACCACATACTACTAATTTAGATAATAAATTACAAGGTCTCTTAGAGA
HEVspike    GCATAGTAGTAAAGCCTCATACCTCATTTATTAATGGTAATTTACAAGGTTTTTTGCAAA
             *  ****** *  ** ***** *  ***  *  **  *** ********  **   * *

BCVspike    TCTCTGTTTGCCAGTATACTATGTGCGAGTACCCACATACGATTTGTCATCCTAATTTGG
HCVspike    TCTCTGTTTGCCAGTATACTATGTGCGAGTACCCACATACGATTTGTCATCCTAATCTGG
CRCVspike   TCTCTGTTTGCCAGTATACTATGTGCGATTACCCACATACGATGTGTCATCCTAATCTGG
HEVspike    TTTCTGTTTGTCAATATACTATGTGTGAATACCCACAGACTATTTGTCATCCTAATTTGG
             * ******** *  *********** **  ******* ** ** ************ ***

BCVspike    GTAATCGGCGCATAGAACTATGGCATTGGGATACAGGTGTTGTTTCCTGTTTATATAAGC
HCVspike    GTAATCGACGCGTAGAACTATGGCATTGGGATACAGGTGTTGTTTCCTGTTTATATAAGC
CRCVspike   GTAATAAACGCATAGAACTATGGCATTGGGATACAGGTGTTGTTCCCTGTTTATATAAGC
HEVspike    GTAATCAACGCATAGAATTATGGCATCATGACACAGATGTTGTTTCTTGTTTATACAGGC
            *****   ***  *** ******** *  **  ***  ****** * ******* * **

BCVspike    GTAATTTCACATATGATGTGAATGCTGATTATTTGTATTTCCATTTTTATCAAGAAGGTG
HCVspike    GTAATTTCACATATGATGTGAATGCTGATTACTTGTATTTCCATTTTTATCAAGAAGGTG
CRCVspike   GTAATTTCACATATGATGTGAATGCTGATTATTTGTATTCCCATTTTTATCAAGAAGGTG
HEVspike    GTAATTTCACATATGATGTGAATGCTGATTATTTATATTTTCACTTTTATCAGGAAGGTG
            *******************************  **  ****  ****  ******* ******

BCVspike    GTACTTTTTATGCATATTTTACAGACACTGGTGTTGTTACTAAGTTTCTGTTTAATGTTT
HCVspike    GTACTTTTTATGCATATTTTACAGACACTGGTGTTGTTACTAAGTTTCTGTTTAATGTTT
CRCVspike   GTACTTTTTATGCATATTTTACAGACACTGGTGTTGTTACTAAGTTTCTGTTTCATGTTT
HEVspike    GCACTTTTTATGCATACTTTACAGATACTGGTTTTGTGACCAAGTTTCTGTTTAAGTTGT
            * ************** ******** ****** **** ** ************  ** * *
```

FIGURE 9 (Page 3 of 12)

```
BCVspike    ATTTAGGCACGGTGCTTTCACATTATTATGTCATGCCTTTGACTTGTAATAGTGCTATGA
HCVspike    ATTTAGGCACGGTGCTTTCACATTATTATGTCCTGCCTTTGACTTGTAATAGTGCTATGA
CRCVspike   ATTTAGGCACGGTGCTTTCACATTATTATGTCATGCCCTTGACTTGTAATAGTGCTATGA
HEVspike    ATTTAGGCACTGTGCTGTCACACTATTATGTTATGCCATTGACTTGTGATAGCGCTTTAT
            ********** ****  ***** ********  ****  ******** **** *** *

BCVspike    CTTTAGAATATTGGGTTACACCTCTCACTTCTAAACAATATTTACTCGCTTTCAATCAAG
HCVspike    CTTTAGAATATTGGGTTACACCTCTCACTTCTAAACAATATTTACTAGCTTTCAATCAAG
CRCVspike   CTTTAGAATACTGGGTTACACCTCTCACTTTTAAACAATATTTACTCGCTTTCAATCAAG
HEVspike    CTTTAGAATATTGGGTTACACCTCTCACTACTAGACAATTTCTTCTAGCCTTTGACCAGG
            **********  *****************  ** ***** *  ** **   * ** *

BCVspike    ATGGTGTTATTTTTAATGCTGTTGATTGTAAGAGTGATTTTATGAGTGAGATTAAGTGTA
HCVspike    ATGGTGTTATTTTTAATGCTGTTGATTGTAAGAGTGATTTTATGAGTGAGATTAAGTGTA
CRCVspike   ATGGTGTTATTTTTAATGCTGTTGATTGTAAGAGTGATTTTATGAGTGAGATTAAGTGTA
HEVspike    ATGGTGTTTTATACCATGCTGTTGATTGTGCTAGTGATTTTATGAGTGAGATTATGTGTA
            ******** * *  ***************    ********************* ****

BCVspike    AAACACTATCTATAGCACCATCTACTGGTGTTTATGAATTAAACGGTTACACTGTTCAGC
HCVspike    AAACACTATCTATAGCACCATCTACTGGTGTTTATGAATTAAACGGTTACACTGTTCAGC
CRCVspike   AAACACTATCTATAGCACCATCTACTGGTGTTTATGAATTAAACGGTTACACTGTTCAGC
HEVspike    AAACTTCTTCAATTACACCACCTACTGGTGTTTATGAACTAAACGGTTACACAGTTCAAC
            ****  ** **   ***** ***************** ************* ***** *

BCVspike    CAATTGCAGATGTTTACCGACGTATACCTAATCTTCCCGATTGTAATATAGAGGCTTGGC
HCVspike    CAATTGCAGATGTTTACCGACGTATACCTAATCTTCCCGATTGTAATATAGAGGCTTGGC
CRCVspike   CAATTGCAGATGTTTACCGACGTATACCTAATCTTCCCGATTGTAATATAGAGGCTTGGC
HEVspike    CTGTTGCCACTGTGTATCGTAGAATACCTGACTTACCCAATTGCGATATCGAAGCTTGGC
            * ****  * *** **  * **  *****  ** *** **** * **** ** ******

BCVspike    TTAATGATAAGTCTGTGCCCTCTCCATTAAATTGGGAACGTAAGACCTTTTCAAATTGTA
HCVspike    TTAATGATAAGTCGGTGCCCTCTCCATTAAATTGGGAACGTAAGACCTTTTCAAATTGTA
CRCVspike   TTAATGATAAGTCGGTGCCTTCTCCATTAAATTGGGAACGTAAGACCTTTTCAAATTGTA
HEVspike    TTAATTCTAAGACCGTTTCTTCGCCTCTTAATTGGGAACGTAAAATTTTTTCTAATTGTA
            *****  **** *  ** * ** ** *************** *  ***** *******
```

FIGURE 9 (Page 4 of 12)

```
BCVspike    ATTTTAATATGAGCAGCCTGATGTCTTTTATTCAGGCAGACTCATTTACTTGTAATAATA
HCVspike    ATTTTAATATGAGCAGCCTGATGTCTTTTATTCAGGCAGACTCATTTACTTGTAATAATA
CRCVspike   ATTTTAATATGAGCAGCCTGATGTCTTTTATCCAGGCTGACTCGTTTACTTGTAATAATA
HEVspike    ATTTTAACATGGGCAGGCTGATGTCTTTTATTCAGGCTGACTCTTTTGGTTGTAACAATA
            ******* *** **** *************** ***** ***** *** ****** ****

BCVspike    TTGATGCAGCTAAGATATATGGTATGTGTTTTTCCAGCATAACTATAGATAAGTTTGCTA
HCVspike    TTGATGCTGCTAAGATATATGGTATGTGTTTTTCCAGCATAACTATAGATAAGTTTGCTA
CRCVspike   TTGATGCTGCTAAGATATACGGTATGTGTTTTTTCAGCATAACTATAGATAAGTTTGCTA
HEVspike    TTGATGCTTCTCGCTTATATGGTATGTGTTTTGGTAGCATTACTATTGACAAGTTTGCTA
            ******* **    **** ************    ***** ***** ** **********

BCVspike    TACCCAATGGTAGGAAGGTTGACCTACAATTGGGCAATTTGGGCTATTTGCAGTCTTTTA
HCVspike    TACCCAATGGTAGGAAGGTTGACCTACAATTGGGCAATTTGGGCTATTTGCAGTCTTTTA
CRCVspike   TACCCAATGGTAGGAAGGTTGACCTACAAATGGGCAATTTGGGCTATTTGCAGTCTTTTA
HEVspike    TACCCAATAGTAGAAAGGTTGATCTGCAAGTGGGTAAATCTGGTTATTTACAATCTTTTA
            ******** **** ******* ** *** ** *** * ** ***** ** *******

BCVspike    ACTATAGAATTGATACTACTGCTACAAGTTGTCAGTTGTATTATAATTTACCTGCTGCTA
HCVspike    ACTATAGAATTGATACTACTGCTACAAGTTGTCAGTTGTATTATAATTTACCTGCTGCTA
CRCVspike   ACTATAGAATTGATACTACTGCTACAAGTTGTCAGTTGTATTATAATTTACCTGCTAGTA
HEVspike    ATTATAAGATTGACACTGCTGTTAGCAGTTGTCAACTCTATTATAGTTTGCCTGCAGCAA
            * **** ***** *** *** **  ********  * ******* *** ***** *

BCVspike    ATGTTTCTGTTAGCAGGTTTAATCCTTCTACTTGGAATAGGAGATTTGGTTTTACAGAAC
HCVspike    ATGTTTCTGTTAGCAGGTTTAATCCTTCTACTTGGAATAGGAGATTTGGTTTTACAGAAC
CRCVspike   ATGTTTCTATTAGCAGGTTTAATCCTTCTATTTGGAATAGGAGATTTGGTTTTACAGAAC
HEVspike    ACGTATCTGTCACTCATTATAATCCTTCATCTTGGAACAGAAGGTATGGGTTTAT----T
            * ** *** * *       * ********  ******* ** ** *** *****

BCVspike    AATCTGTTTTTAAGCCTCAACCTGTAGGTGTTTTTACTGATCATGATGTTGTTTATGCAC
HCVspike    AATCTGTTTTTAAGCCTCAACCTGTAGGTGTTTTTACTCATCATGATGTTGTTTATGCAC
CRCVspike   AATCTGTTTTTAAGCCTCAACCTGTAGGTGTTTTTACTGATCATGATGTTGTTTATGCAC
HEVspike    AATCAGAGTTTTGGTTCCAG-----AGGC-CTT--------CATGATGCTGTATATTCAC
            **** * ***  *   **     ***  **         ******* *** *** ***
```

FIGURE 9 (Page 5 of 12)

```
BCVspike    AACATTGTTTTAAAGCTCCCACAAATTTCTGTCCGTGTAAATTGGATGGGTCTTTGTGTG
HCVspike    AACATTGTTTTAAAGCTCCCACAAATTTCTGTCCGTGTAAATTGGATGGGTCTTTGTGTG
CRCVspike   AACATTGTTTTAAAGCTCCCACAAATTTCTGTCCGTGTAAATTGAATGGGTCTTTGTGTG
HEVspike    AGCAATGTTTTAATACACCTAATACATATTGTCCTTGTA----GAACAAGTC--AATGCA
             * ** *******  * **  *  *  *  ***** ****      * *   ***    **

BCVspike    TAGGTAGTGGTTCTGGTATAGATGCTGGTTATAAAAATAGTGGTATAGGCACTTGTCCTG
HCVspike    TAGGTAATGGTCCTGGTATAGATGCTGGTTATAAAAATAGTGGTATAGGCACTTGTCCTG
CRCVspike   TAGGTAGTGGTTTTGGTATAGATGCTGGTTATAAAAATAGTGGTATAGGCACTTGTCCTG
HEVspike    TAGGTGGTG---CTGGCACAGGAACTTGTCCTGTAGGCACCACTGTGCGCAAGTGTTTTG
            *****  **    *** *  **   ** **  *    *    *  *  ***  ***  **

BCVspike    CAGGTACTAATTATTTAACTTGTCATAATGCTGCCCAATGTAATTGTTTGTGCACTCCAG
HCVspike    CAGGTACTAATTATTTAACTTGCCATAATGCTGCCCAATGTGATTGTTTGTGCACTCCCG
CRCVspike   CAGGTACTAATTATTTAACTTGTTATAATGCTAACCAATGTGATTGTTTGTGCACTCCAG
HEVspike    CTG---C-AGTTAC--A---------AACGCTACTAAGTGTACTTGCTGGTGTCAACCAG
             *  *    * * ***    *     ** ***   * ***  *** ***       ** *

BCVspike    ACCCCATTACATCTAAATCTACAGGGCCTTATAAGTGCCCCCAAACTAAATATTTAGTTG
HCVspike    ACCCCATTACATCTAAATCTACAGGGCCTTACAAGTGCCCCCAAACTAAATACTTAGTTG
CRCVspike   ACCCTATTTTATCTAAATCTACAGGGCCTTATAAGTGCCCCCAAACTAAATACTTAGTTG
HEVspike    ATCCTTCCACATATAAAGGTGTAAATGCCTGGACTTGTCCGCAATCTAAAGTTTCTATAC
            * **    ** ****     *  *  *  *       **  *   *  *****      *

BCVspike    GCATAGGTGAGCACTGTTCGGGTCTTGCTATTAAAAGTGATTATTGTGGAGGTAATCCTT
HCVspike    GCATAGGTGAGCACTGTTCGGGTCTTGCTATTAAAAGTGATTATTGTGGAGGTAATCCTT
CRCVspike   GCATAGGTGAGCACTGTTCTGGTCTTGCTATTAAAAGTGATTATTGTGGAGGCAATCCTT
HEVspike    AACCAGGTCAGCATTGCCCTGGCTTGGGTCTTGTGGAGGATGATTGCTCTGGTAATCCTT
               * *** *** *  *  *  **  ** *   *    ** *  ** ****   ** *******

BCVspike    GTACTTGCCAACCACAAGCATTTTTGGGTTGGTCTGTTGATTCTTGTTTACAAGGGGATA
HCVspike    GTACTTGCCAACCACAAGCATTTTTGGGTTGGTCTGTTGACTCTTGTTTACAAGGGGATA
CRCVspike   GTACTTGCCAACCAAAAGCATTTTTGGGTTGGTCTGTGGACTCTTGTTTACAAGGGGATA
HEVspike    GCACTTGTAAACCACAGGCTTTCATAGGCTGGAGTTCAGAAACTTGTTTGCAAAATGGTA
            * *****    ****  **  **  * **  **     *   ** ******* ***   **
```

FIGURE 9 (Page 6 of 12)

```
BCVspike    GGTGTAATATCTTTGCTAATTTTATTTTGCATGATGTTAATAGTGGTACTACTTGTTCTA
HCVspike    GGTGTAATATTTTTGCTAATTTTATTTTGCATGATGTTAATAGTGGTACTACTTGTTCTA
CRCVspike   GGTGTAATATTTTTGCTAATTTTATTTTGCATGGTGTTAATAGTGGTACTACTTGTTCTA
HEVspike    GGTGTAATATTTTTGCTAATTTTATTTTGAATGATGTTAATAGCGGTACTACCTGTTCTA
            ********* **************** *** ******** ******* *******

BCVspike    CTGATTTACAAAAATCAAACACAGACATAATTCTTGGTGTTTGTGTTAATTATGATCTTT
HCVspike    CTGATTTACAAAAATCAAACACAGACATAATTCTTGGTGTTTGTGTTAATTATGATCTTT
CRCVspike   CTGATTTACAAAAATCAAACACAGACATAATTCTTGGTGTTTGTGTTAATTATGATCTTT
HEVspike    CTGATTTACAACAGGGTAATACTAATATTACTACTGATGTTTGTGTTAATTATGACCTAT
            ********** *    ** **   * ** * *   ** ****************** * *

BCVspike    ATGGTATTACAGGCCAAGGTATTTTTGTTGAGGTTAATGCGACTTATTATAATAGTTGGC
HCVspike    ATGGTATTACAGGCCAAGGTATTTTTGTTGAGGTTAATGCGCCTTATTATAATAGTTGGC
CRCVspike   ATGGTATTACAGGCCAAGGTATTTTTGTTGAGGTTAATGCGACTTATTATAATAGTTGGC
HEVspike    ATGGCATTACAGGCCAGGGCATACTTATAGAAGTTAATGCCACGTATTATAATAGTTGGC
            **** *********** **  **   ** * ** ********  * ***************

BCVspike    AGAACCTTTTATATGATTCTAATGGTAATCTCTATGGTTTTAGAGACTACTTAACAAACA
HCVspike    AGAACCTTTTATATGATTCTAATGGTAATCTCTATGGTTTTAGAGACTACTTAACAAACA
CRCVspike   AGAACCTTTTATATGATTCTAATGGTAATCTCTATGGTTTTAGGGACTACTTAACAAACA
HEVspike    AGAATCTTCTTTATGATTCTAGTGGTAATCTCTATGGCTTTAGAGATTATTTATCAAATA
            **** *** * ********** *************** ***** **  ** **  *** *

BCVspike    GAACTTTTATGATTCGTAGTTGCTATAGCGGTCGTGTTTCAGCGGCCTTTCATGCTAATT
HCVspike    GAACTTTTATGATTCGTAGTTGCTATAGCGGTCGTGTTTCAGCGGCCTTTCATGCTAACT
CRCVspike   GAACTTTTATGATTCGTAGTTGCTATAGCGGTCGTGTTTCAGCGGGCTTTCACTCTAACT
HEVspike    GAACCTTTCTTATTCGTAGCTGCTATAGTGGAAGAGTTTCAGCAGTCTTTCATGCTAACT
            ****  ** * ******* ******** **  * ******** *   ****** *****  *

BCVspike    CTTCCGAACCAGCATTGCTATTTCGGAATATTAAATGCAATTACGTTTTAATAATACTC
HCVspike    CTTCCGAACCAGCATTGCTATTTCGGAATATTAAATGCAGTTACGTTTTAATAATACTC
CRCVspike   CTTCCGAACCAGCATTGCTATTTCGGAATATTAAATGCAATTACGTTTTTAATAATACTC
HEVspike    CTTCTGAACCAGCTTTGATGTTTCGTAATCTTAAATGCAGCCACGTTTTTAATTATACCA
            **** ******** *** *  ***** *** ********    *********  *** *
```

FIGURE 9 (Page 7 of 12)

```
BCVspike    TTTCACGACAGCTGCAACCTATTAACTATTTTGATAGTTATCTTGGTTGTGTTGTCAATG
HCVspike    TTTCACGACAGCTGCAACCTATTAACTATTTTGATAGTTATCTTGGTTGTGTTGTCAATG
CRCVspike   TTTCACGACAGCTGCAACCTATTAACTATTTTGATAGTTATCTTGGTTGTGTTGTCAATG
HEVspike    TTTTAAGACAAATACAGCTTGTTAATTATTTTGATAGTTACCTTGGTTGTGTTGTTAATG
            ***  * ****   * **  * * **** *************** ************ ****

BCVspike    CTGATAATAGTACTTCTAGTGCTGTTCAAACATGTGATCTCACAGTAGGTAGTGGTTACT
HCVspike    CTGATAATAGTACTTCTAGTGTTGTTCAAACATGTGATCTCACAGTAGGTAGTGGTTACT
CRCVspike   CTGATAATAGTACTTCTAGTTCTGTTCAAACATGTGATCTCACAGTAGGTAGTGGTTACT
HEVspike    CTTATAATAATACAGCTAGTGCTGTAAGTACTTGTGATTTAACCGTTGGTAGCGGCTATT
            ** ****** ***  *****    ***     **  ****** * ** ** ***** ** ** *

BCVspike    GTGTGGATTACTCTACAAAAAGACGAAGTCGTAGAGCGATTACCACTGGTTATCGGTTTA
HCVspike    GTGTGGATTACTCTACAAAAAGACGAAGTCGTAGAGCGATTACCACTGGTTATCGGTTTA
CRCVspike   GGGGGGATTACTCTACACAAAGACGAAGTCGTAGAACGATTACCACTGGTTATCGGTTTA
HEVspike    GTGTTGATTATGTTACAGCACTTAGATCACGTAGATCTTTTACTACAGGTTATCGCTTTA
            *  *  ****      ****    *     **     ***** **  ** ******** ****

BCVspike    CTAATTTTGAGCCATTTACTGTTAATTCAGTAAATGATAGTTTAGAACCTGTAGGTGGTT
HCVspike    CTAATTTTGAGCCATTTACTGTTAATTCAGTAAATGATAGTTTAGAACCTGTAGGTGGTT
CRCVspike   CTAATTTTGAGCCATTTACTGTTAATCCAGTAAATGATAGTTTACACCCTGTAGGTGGTT
HEVspike    CTAATTTTGAACCATTTGCCGCTAATTTGGTAAATGATAGTATAGAACCTGTTGGTGGTT
            ********** ****** *  * ****      ************ ** * ***** *******

BCVspike    TGTATGAAATTCAAATACCTTCAGAGTTTACTATAGGTAATATGGAGGAGTTTATTCAAA
HCVspike    TGTATGAAATTCAAATACCTTCAGAGTTTACTATAGGTAATATGGAGGAGTTTATTCAAA
CRCVspike   TGTATGAAATTCAAATACCTTCAGAGTTTACTATAGGTAATATGGAGGAGTTTATTCAAA
HEVspike    TGTATGAAATACAGATACCTTCAGAGTTTACCATTGGTAATTTAGAAGAATTCATTCAAA
            ********** ** ***************** ** ****** * ** ** ** ** *******

BCVspike    TAAGCTCTCCTAAAGTTACTATTGATTGTTCTGCTTTTGTCTGTGGTGATTATGCAGCAT
HCVspike    CAAGCTCTCCTAAAGTTACTATTGATTGTTCTGCTTTTGTCTGTGGTGATTATGCAGCAT
CRCVspike   CAAGATCTCCTAAAGTTACTATTGATTGTCCTGTTTTTGTCTGTGGTGATTATGCAGCAT
HEVspike    CGAGTTCCCCTAAGGTTACTATAGATTGTGCTACATTTGTTTGTGGTGACTATGCTGCAT
            * **  ** ***** ******** ****** **    ****** ******** ***** ****
```

FIGURE 9 (Page 8 of 12)

```
BCVspike    GTAAATCACAGTTGGTTGAATATGGTAGTTTCTGTGACAATATTAATGCTATACTCACAG
HCVspike    GTAAATCACAGTTGGTTGAATATGGTAGCTTCTGTGACAATATTAATGCTATACTCACAG
CRCVspike   GTAAATCACAGTTGGTTGAATATGGTAGTTTTTGTGACAATATTAATGCTATACTCACAG
HEVspike    GTAGACAACAGTTAGCTGAGTATGGTAGTTTTTGTGAGAACATTAATGCTATACTCATAG
            *** * ****** * *** ******** ** ***** ** **************** **

BCVspike    AAGTAAATGAACTACTTGACACTACACAGTTGCAAGTAGCTAATAGTTTAATGAATGGTG
HCVspike    AAGTAAATGAACTACTTGACACTACACAGTTGCAAGTAGCTAATAGTTTAATGAATGGTG
CRCVspike   AAGTAAATGAACTACTTGACACTACACAGTTGCAAGTAGCTAATAGTTTAATGAATGGTG
HEVspike    AAGTAAATGAACTACTTGACACTACACAGTTGCAAGTAGCTAATAGTTTAATGAATGGAG
            *********************************************************** *

BCVspike    TCACTCTTAGCACTAAGCTTAAAGATGGCGTTAATTTCAATGTAGACGACATCAATTTTT
HCVspike    TCACTCTTAGCACTAAGCTTAAAGATGGCGTTAATTTCAATGTAGACGACATCAATTTTT
CRCVspike   TCACTCTTAGCACTAAGCTTAAAGATGGCTTTAATTTCAATGTAGATGACATCAATTTTT
HEVspike    TCACCCTTAGTACTAAGATTAAGGATGGGATTAATTTCAATGTTGACGATATCAACTTCT
            **** ***** ****** **** ***** ************* ** ** ***** ** *

BCVspike    CCCCTGTATTAGGTTGTTTAGGAAGCGATTGTAATAAAGTTTCCAGTAGATCTGCTATAG
HCVspike    CCCCTGTATTAGGTTGTTTAGGAAGCGCTTGTAATAAAGTTTCCAGCAGATCTGCTATAG
CRCVspike   CCCCTGTATTAGGTTGTTTAGGAAGCGAATGTAATAAAGTTTCCAGTAGATCTGCTATAG
HEVspike    CCTCTGTATTAGGTTGTTTAGGAAGCGAATGTAACAGAGCTTCCACTAGATCTGCTATAG
            ** ********************* ***** * ** ***** *************

BCVspike    AGGATTTACTTTTTTCTAAAGTAAAGTTATCTGATGTCGGTTTTGTTGAGGCTTATAATA
HCVspike    AGGATTTACTTTTTTCTAAAGTAAAGTTATCTGATGTCGGTTTCGTTGAGGCTTATAATA
CRCVspike   AGGATTTACTTTTTTCTAAAGTAAAGTTATCTGATGTTGGTTTTGTTGATGCTTATAATA
HEVspike    AGGATTTACTTTTTGATAAAGTAAAATTGTCTGATGTCGGTTTTGTACAGGCCTATAATA
            ************** ******** ** ******* ****** ** ** * ** *******

BCVspike    ATTGTACTGGAGGTGCCGAAATTAGGGACCTCATTTGTGTGCAAAGTTATAATGGTATCA
HCVspike    ATTGTACTGGAGGTGCCGAAATTAGGGACCTCATTTGTGTGCAAAGTTATAATGGTATCA
CRCVspike   ATTGTACTGGAGGTGCCGAAATTAGGGACCTCATTTGTGTGCAAAGTTATAATGGTATCA
HEVspike    ACTGCACTGGAGGAGCCGAAATTAGGGATCTCATTTGTGTGCAAAGTTATAATGGTATCA
            * ** ******** ************* ********************************
```

FIGURE 9 (Page 9 of 12)

```
BCVspike     AAGTGTTGCCTCCACTACTCTCAGAAAATCAGATCAGTGGATACACTTTGGCTGCTACCT
HCVspike     AAGTGTTGCCTCCACTGCTCTCAGTAAATCAGATCAGTGGATACACTTTGGCTGCCACCT
CRCVspike    AAGTGTTGCCTCCACTGCTCTCAGAAAATCAGATCAGTGGATACACTTTGGCTGCCACCT
HEVspike     AAGTGTTGCCTCCATTGTTATCTGAAAATCAGATTAGTGGTTACACTTCGGCAGCCACCG
             ************** *   *  ** *  ********  ***** ******* ***  ** ***

BCVspike     CTGCTAGTCTGTTTCCTCCTTGGTCAGCAGCAGCAGGCGTACCATTTTATTTAAATGTTC
HCVspike     CTGCTAGTCTGTTTCCTCCTTGGTCAGCAGCAGCAGGTGTACCATTTTATTTAAATGTTC
CRCVspike    TTGCTAGTCTGTTTCCTCCTTGGTCAGCAGCAGCAGGCGTACCATTTTATTTAAATGTTC
HEVspike     CTGCTAGCCTATTTCCTCCCTGGACAGCTGCAGCAGGTGTACCATTTTATTTAAATGTTC
             ****** ** ******** *** **** ******* ********************

BCVspike     AGTATCGTATTAATGGGATTGGTGTTACCATGGATGTTCTAAGTCAAAATCAAAAGCTTA
HCVspike     AGTATCGTATTAATGGGATTGGTGTTACCATGGATGTGTTAAGTCAAAATCAAAAGCTTA
CRCVspike    AGTATCGTATTAATGGTATTGGTGTTACCATGGATGTGCTAACTCAAAATCAAAAGCTTA
HEVspike     AGTATCGTATAAATGGGCTTGGCGTCACCATGGATGTGCTAAGCCAAAACCAAAAGCTTA
             ********** ****    **** ** ***********    ***  *****  *********

BCVspike     TTGCTAATGCATTTAACAATGCCCTTGATGCTATTCAGGAAGGGTTTGATGCTACCAATT
HCVspike     TTGCTAATGCATTTAGCAATGCTCTTGATGCTATTCAGGAAGGGTTTGATGCTACCAATT
CRCVspike    TTTCTAATGCATTTAACAATGCCCTTGATGCTATTCAGGAAGGGTTTGATGCTACCAATT
HEVspike     TTGCTAGTGCATTTAACAACGCTCTTGATTCTATCCAGGAAGGGTTCGACGCAACCAATT
             ** *** ********  ***  **  ***** ****  ******** ** ** *******

BCVspike     CTGCTTTAGTTAAAATTCAAGCTGTTGTTAATGCAAATGCTGAAGCTCTTAATAACTTAT
HCVspike     CTGCTTTAGTTAAAATTCAAGCTGTTGTTAATGCAAATGCTGAAGCTCTTAATAACTTAT
CRCVspike    CTGCTTTAGTTAAAATTCAAGCTGTTGTTAATGCAAATGCTGAAGCTCTTAATAACTTAT
HEVspike     CTGCTTTAGTTAAAATTCAGGCTGTTGTTAATGCAAATGCTGAAGCACTTAATAACTTAT
             *******************  **************************** ************

BCVspike     TGCAACAACTCTCTAATAGATTTGGTGCTATAAGTTCTTCTTTACAAGAAATTCTATCTA
HCVspike     TGCAACAACTCTCTAATAGATTTGGTGCTATAGGTTCTTCTTTACAAGAAATTCTATCTA
CRCVspike    TGCRACAACTCTCTAATAAATTTGGTGCTATAAGTGCTTCTTTACAAGAAATTCTATCTA
HEVspike     TGCAGCAACTCTCTAACAGATTTGGTGCCATAAGTGCCTCTTTACAAGAAATTTTATCCA
             ***  ********** *  ********  *** **  *  ************* **** *
```

FIGURE 9 (Page 10 of 12)

```
BCVspike    GACTTGATGCTCTTGAAGCGCAAGCTCAGATAGACAGACTTATTAATGGGCGTCTTACCG
HCVspike    GACTGGATGCTCTTGAAGCGCAAGCTCAGATAGACAGACTTATTAATGGGCGTCTTACCG
CRCVspike   GACTTGATGCTCTTGAAGCGCAAGCTCAGATAGACAGACTTATCAATGGGCGTCTTACCG
HEVspike    GGCTCGATGCTCTTGAAGCTAAAGCTCAGATAGACAGACTTATTAATGGGCGTCTCACCG
            *  ** ************  ********************* **********  ****

BCVspike    CTCTTAATGCTTATGTTTCTCAACAGCTTAGTGATTCTACACTAGTAAAATTTAGTGCAG
HCVspike    CTCTTAATGCTTATGTTTCTCAACAGCTTAGTGATTCTACACTAGTAAAATTTAGTGCAG
CRCVspike   CTCTTAATGCTTATGTTTCTCAACAGCTTAGTGATTCTACACTAGTAAAATTTAGTGCAG
HEVspike    CTCTTAATGCTTATGTTTCTCAGCAGCTTAGTGATTCTACACTAGTAAAATTTAGTGCAG
            ********************** *************************************

BCVspike    CACAAGCTATGGAGAAGGTTAATGAATGTGTCAAAAGCCAATCATCTAGGATAAATTTTT
HCVspike    CACAAGCTATGGAGAAGGTTAATGAATGTGTCAAAAGCCAATCATCTAGGATAAATTTTT
CRCVspike   CACAAGCTATGGAGAAGGTTAATGAATGTGTCAAAAGCCAATCATCTAGGATAAATTTTT
HEVspike    CACAAGCTATTGAGAAGGTTAATGAATGTGTTAAAAGCCAATCATCTAGGATAAATTTCT
            ********** ***** ************** ***************************  *

BCVspike    GTGGTAATGGTAATCATATTATATCATTAGTGCAGAATGCTCCATATGGTTTGTATTTTA
HCVspike    GTGGTAATGGTAATCATATTATATCATTAGTGCAGAATGCTCCATATGGTTTGTATTTTA
CRCVspike   GTGGTAATGGTAATCATATTATATCATTAGTGCAGAATGCTCCATATGGTTTGTATTTTA
HEVspike    GTGGTAATGGTAATCATATTATATCATTAGTACAGAATGCTCCATATGGTTTGTATTTTA
            ******************************* ****************************

BCVspike    TCCACTTTAGCTATGTCCCTACTAAGTATGTCACTGCGAAGGTTAGTCCCGGTCTGTGCA
HCVspike    TCCACTTTAGCTATGTCCCTACTAAGTATGTCACTGCGAAGGTTAGTCCCGGTCTGTGCA
CRCVspike   TCCACTTTAGCTATGTCCCTACTAAGTATGTCACTGCGAAGGTTAGTCCCGGTCTGTGCA
HEVspike    TCCATTTTAGCTATGTCCCCACCAAGTATGTTACAGCAAAGGTTAGTCCTGGTTTGTGCA
            **** **************  ** ******* ** ** ********** *** ******

BCVspike    TTGCTGGTGATAGAGGTATAGCCCCTAAGAGTGGTTATTTTGTTAATGTAAATAACACTT
HCVspike    TTGCTGGTGATAGAGGTATAGCCCCTAAGAGTGGTTATTTTGTTAATGTAAATAATACTT
CRCVspike   TYGCAGGTGATAGAGGTATAGCTCCTAAGAGTGGTTATTTTGTTAATGTAAATAACACTT
HEVspike    TTGCTGGCGATATAGGAATATCGCCTAAGAGTGGTTATTTTATTAATGTAAATAACTCTT
            * ** ** **** ***  ***  * ****************  ************  ***
```

FIGURE 9 (Page 11 of 12)

```
BCVspike    GGATGTTCACTGGTAGTGGTTATTACTACCCTGAACCTATAACTGGAAATAATGTTGTTG
HCVspike    GGATGTTCACTGGTAGTGGTTATTACTACCCTGAACCCATAACTGGAAATAATGTTGTTG
CRCVspike   GGATGTTCACTGGTAGTGGTTATTACTACCCTGAACCTATAACTGGAAATAATGTGGTTG
HEVspike    GGATGTTCACTGGTAGTGGCTATTACTACCCTGAACCTATAACCCAAAATAATGTTGTTG
            ******************* ***************** ****    ******** ****

BCVspike    TTATGAGTACCTGTGCTGTTAATTACACTAAAGCACCGGATGTAATGCTGAACATTTCAA
HCVspike    TTATGAGTACCTGTGCTGTTAACTATACTAAAGCGCCGGATGTAATGCTGAACATTTCAA
CRCVspike   TTATGAGTACCTGTGCTGTTAACTATACTAAAGCACCGGATGTAATGCTGAACATTTCAA
HEVspike    TGATGAGTACGTGTGCTGTTAATTATACTAAAGCACCGGATCTAATGCTGAACACATCGA
            * ******* *********** ** ********* ****** ************  ** *

BCVspike    CACCCAACCTCCCTGATTTTAAGGAAGAGTTGGATCAATGGTTTAAAAACCAAACATCAG
HCVspike    CACCCAACCTCCATGATTTTAAGGAAGAGTTGGATCAATGGTTTAAAAACCAAACATCAG
CRCVspike   CACCCAACCTCCCTGATTTTAAGGAAGAGTTGGATCAATGGTTTAAAAACCAAACATTAA
HEVspike    CACCCAACCTTCCTGATTTCAAGGAAGAATTGTATCAATGGTTTAAAAACCAATCTTCAT
            **********  * ****** ******* *** ****************   *   * *

BCVspike    TGGCACCAGATTTGTCACTTGATTATATAAATGTTACATTCTTGGACCTACAAGATGAAA
HCVspike    TGGCACCAGATTTGTCACTTGATTATATAAATGTTACATTCTTGGACCTACAAGATGAAA
CRCVspike   TGGCACCAGATTTGTCACTTGATTATATAAATGTTACATTCTTGGACCTACAAGATGAAA
HEVspike    TGGCACCAGATTTGTCATTTGATTATATTAATGTTACGTTCTTGGACCTACAAGATGAAA
            ***************** ********** ******** **********************

BCVspike    TGAATAGGTTACAGGAGGCAATAAAAGTTTTAAATCAGAGCTACATCAATCTCAAGGACA
HCVspike    TGAATAGGTTACAGGAGGCAATAAAAGTTTTAAATCAGAGCTACATCAATCTCAAGGACA
CRCVspike   TGAATAGGTTACAGGAGGCAATAAAAGTTTTAAATCATAGCTACATCAATCTCAAGGACA
HEVspike    TGAATAGGTTACAAGAAGCTATAAAAGTTCTAAATCATAGCTACATCAATCTCAAGGACA
            ************* ** ** ********* ****** ***********************

BCVspike    TTGGTACATATGAGTATTATGTAAAATGGCCTTGGTATGTATGGCTTTTAATTGGCCTTG
HCVspike    TTGGTACATATGAGTATTATGTAAAATGGCCTTGGTATGTATGGCTTTTAATTGGCTTTG
CRCVspike   TTGGTACATATGAATATTATGTAAAATGGCCTTGGTATGTATGGCTTTTAATTGGCCTTG
HEVspike    TTGGTACATATGAGTATTATGTGAAATGGCCTTGGTATGTATGGCTTTTAATTTGCCTTG
            ************* ********  ****************************** ****
```

FIGURE 9 (Page 12 of 12)

```
BCVspike     CTGGTGTAGCTATGCTTGTTTTACTATTCTTCATATGCTGTTGTACAGGATGTGGGACTA
HCVspike     CTGGTGTAGCTATGCTTGTTTTACTATTCTTCATATGCTGTTGTACAGGATGTGGGACTA
CRCVspike    CTGGCGTAGCTATGCTTGTTTTACTATTCTTCATATGCTGTTGTACAGGATGTGGGACTA
HEVspike     CTGGTGTAGTTATGCTTGTTTTACTATTCTTCATATGCTGCTGTACAGGATGTGGGACTA
             **** **** ************************** ******************

BCVspike     GTTGTTTTAAGAAATGTGGTGGTTGTTGTGATGATTATAC--------------------
HCVspike     GTTGTTTTAAGATATGTGGTGGTTGTTGTGATGATTATACTGGACACCAGG---------
CRCVspike    GTTGTTTTAAGAAATGCGGTGGTTGTTGTGATGATTATACTGGACATCAGG---------
HEVspike     GTTGTTTTAAGAAATGTGGCGGTTGTTTTGATGATTATACTGGACACCAGGAGTTTGTAA
             ************ *** ** ****** ************

BCVspike     ----------------------------
HCVspike     ----------------------------
CRCVspike    ----------------------------
HEVspike     TCAAAACTTCACATGACGATTAATTTCGT
```

FIGURE 10 (Page 1 of 5)

```
BCVspikepro    ----MFLILLISLPMALAVIGDLKCTTVSINDVDTGVPSVSTDTVDVTNGLGTYYVLDRV
HCVspikepro    ----MFLILLISLPTAFAVIGDLKCTTVSINDIDTGAPSISTDIVDVTNGLGTYYVLDRV
CRCVspikepr    ----MFLILLISLPMAFAVIGDLKCTTVSINDVDTGAPSISTDVVDVTNGLGTYYVLDRV
HEVspikepro    ----MFFILLITLPSVFAVIGDLKCNTSSINDVDTGVPSISSEVVDVTNGLGTFYVLDRV
CECVspikepr    MIVLVTCILLLCSYHTASSTSNNDCRQVNVTQLDGNENLIRDFLFQNFKEEGTVVVGG--
                 :  ***:       .  :  .: .*  .:.::*.  :    .: :  ** *  .
                                                            ╱103
BCVspikepro    YLNTTLLLNGYYPTSGSTYRNMALKGTLLLSTLWFKPPFLSDFINGIFAKVKNTKVIKNG
HCVspikepro    YLNTTLLLNGYYPTSGSTYRNMALKGTLLLSRLWFKPPFLSDFINGIFAKVKNTKVIKKG
CRCVspikepr    YLNTTLLLNGYYPTSGSTYRNMALKGTLLLSTLWFKPPFLSDFIDGVFAKVKNTKVIKDG
HEVspikepro    YLNTTLLLNGYYPISGATFRNVALKGTRLLSTLWFKPPFLSPFNDGIFAKVKNSRFSKHG
CECVspikepr    YYPTEVWYNCSRTATTTAYEYFSNIHAFYFDMEAMENSTGNARGKPLLFHVHGEPVS--V
                *  *  :  *    .   :::.   .:     :   :.    ::   .  ::  :*:. .
                 ╱118                                         ╱166  ╱171
BCVspikepro    VMYSEFPAITIGSTFVNTSYSVVVQPHTTNLDNKLQGLLEISVCQYTMCEYPHTICHPNL
HCVspikepro    VMYSEFPAITIGSTFVNTSYSVVVQPHTTNLDNKLQGLLEISVCQYTMCEYPHTICHPNL
CRCVspikepr    VVYSEFPAITIGSTFVNTSYSVVVQPHTTNLDNKLQGLLEISVCQYTMCDYPHTMCHPNL
HEVspikepro    VIYSEFPAITIGSTFVNTSYSIVVKPHTSFINGNLQGFLQISVCQYTMCEYPQTICHPNL
CECVspikepr    IIYISYRDDVQHRPLLKHGLVCITESRNIDYN-SFTSSQWNSICTGNDRKIPFSVIPTDN
                ::* .:    .   .:::   :.:.:.    :  .:    *:*  . . * :: .:
                 ╱179      ╱192          ╱210
BCVspikepro    GNRRIELWHWDTGVVSCLYKRNFTYDVN------ADYLYFHFYQEGGTFYAYFTDTGVVT
HCVspikepro    GNRRVELWHWDTGVVSCLYKRNFTYDVN------ADYLYFHFYQEGGTFYAYFTDTGVVT
CRCVspikepr    GNKRIELWHWDTGVVPCLYKRNFTYDVN------ADYLYSHFYQEGGTFYAYFTDTGVVT
HEVspikepro    GNQRIELWHHDTDVVSCLYRRNFTYDVN------ADYLYFHFYQEGGTFYAYFTDTGFVT
CECVspikepr    GTKIYGLEWNDEFVTAYISGRSYNWNINNNWFNNVTLLYSRSSTATWQHSAAYVYQGVSN
               *.:   *   *  *..  :  *.:.:::*      .  ** :    . * :.  *. .
                    ╱235                      ╱267
BCVspikepro    KFLFNVYLGTVLSHYYVMP--------LTCNSAMTLEYWVTPLTSKQYLLAFNQDGVIF
HCVspikepro    KFLFNVYLGTVLSHYYVLP--------LTCNSAMTLEYWVTPLTSKQYLLAFNQDGVIF
CRCVspikepr    KFLFHVYLGTVLSHYYVMP--------LTCNSAMTLEYWVTPLTFKQYLLAFNQDGVIF
HEVspikepro    KFLFKLYLGTVLSHYYVMP--------LTCDSALSLEYWVTPLTTRQFLLAFDQDGVLY
CECVspikepr    FTYYKLNNTNGLKTYELCEDYEYCTGYATNIFAPTVGGYIPDGFSFNNWFLLTNSSTFVS
               :::   . *. * :            . :.    *    :: .:::* :.. .:
```

FIGURE 10 (Page 2 of 5)

```
BCVspikepro   NAVDCKSDFMSEIKCKTLSIAPSTGVYELNGYTVQPIADVYRR-IPNLPDCNIEAWLNDK
HCVspikepro   NAVDCKSDFMSEIKCKTLSIAPSTGVYELNGYTVQPIADVYRR-IPNLPDCNIEAWLNDK
CRCVspikepr   NAVDCKSDFMSEIKCKTLSIAPSTGVYELNGYTVQPIADVYRR-IPNLPDCNIEAWLNDK
HEVspikepro   HAVDCASDFMSEIMCKTSSITPPTGVYELNGYTVQPVATVYRR-IPDLPNCDIEAWLNSK
CECVspikepr   GRFVTNQPLLVNCLWPVPSFGVAAQEFCFEGAQFSQCNGVFLNNTVDVIRFNLNFTADVQ
                .  . :: :    .*: .:  : ::*  ..   *: .  ::   :::    : :
                                                                       388
BCVspikepro   SVPSPLNWERKTFSNCNFNMSSLMSFIQADSFTCN------NIDAAKIYGMCFSSITIDK
HCVspikepro   SVPSPLNWERKTFSNCNFNMSSLMSFIQADSFTCN------NIDAAKIYGMCFSSITIDK
CRCVspikepr   SVPSPLNWERKTFSNCNFNMSSLMSFIQADSFTCN------NIDAAKIYGMCFFSITIDK
HEVspikepro   TVSSPLNWERKIFSNCNFNMGRLMSFIQADSFGCN------NIDASRLYGMCFGSITIDK
CECVspikepr   SGMGATVFSLNTTGGCILEISCYNDIVSESSFYSYGEIPFGVTDGPRYCYVLYNGTALKY
                :  ..   :. :   ..* :::.    .::. .** .       *...:   : : .::.
                     407                                 436 440    447
BCVspikepro   FAIPNGRKVDLQLGNLGYLQSFNYRIDTTATSCQLYYNLPAAN-VSVSRFNPSTWNRRFG
HCVspikepro   FAIPNGRKVDLQLGNLGYLQSFNYRIDTTATSCQLYYNLPAAN-VSVSRFNPSTWNRRFG
CRCVspikepr   FAIPNGRKVDLQMGNLGYLQSFNYRIDTTATSCQLYYNLPASN-VSISRFNPSIWNRRFG
HEVspikepro   FAIPNSRKVDLQVGKSGYLQSFNYKIDTAVSSCQLYYSLPAAN-VSVTHYNPSSWNRRYG
CECVspikepr   FGTLPPSVKEIAISKWGQFYINGYNFFSTFPIDCISFNLTTGDSGAFWTIAYTSYTEALV
              *.            :: :.: * :   .*.: ::  .   : :.*.:.:  :.     : :...
                                                        501
BCVspikepro   FTEQSVFKPQPVGVFTDHDVVYAQHCFKAPTNFCPCKLDGSLCVGSGSGIDAGYKNSGIG
HCVspikepro   FTEQSVFKPQPVGVFTHHDVVYAQHCFKAPTNFCPCKLDGSLCVGNGPGIDAGYKNSGIG
CRCVspikepr   FTEQSVFKPQPVGVFTDHDVVYAQHCFKAPTNFCPCKLNGSLCVGSGFGIDAGYKNSGIG
HEVspikepro   FINQS------FGSRGLHDAVYSQQCFNTPNTYCPCRT--SQCIGG----------AGTG
CECVspikepr   QVENTAIKKVTYCNSHINNIKCSQLTANLQNGFYPVASSEVGLVNKSVVLLPSFYSHTSV
              :::              ::    :*   : . : *           :.
                      525  528      540
BCVspikepro   TCPAGTNYLTCH----NAAQCNCLCTPDPITSKSTGPYKCPQTKYLVGIGEHCSGLAIKS
HCVspikepro   TCPAGTNYLTCH----NAAQCDCLCTPDPITSKSTGPYKCPQTKYLVGIGEHCSGLAIKS
CRCVspikepr   TCPAGTNYLTCY----NANQCDCLCTPDPILSKSTGPYKCPQTKYLVGIGEHCSGLAIKS
HEVspikepro   TCPVGTTVRKCFAAVTNATKCTCWCQPDPSTYKGVNAWTCPQSKVSIQPGQHCPGLGLVE
CECVspikepr   NITIDLGMKRSGYG--QPIASTLSNITLPMQDNNTDVYCIRSNQFSVYVHSTCKSSLWDN
              . . .      .      :: .     . *  :...:    ..: :    . * .     .
```

FIGURE 10 (Page 3 of 5)

```
                       ╱582                      ╱608
BCVspikepro   DYCGGNPCTCQPQAFLGWSVDSCLQGDRCN--IFANFILHDVNSGTTCSTDLQKSNTDII
HCVspikepro   DYCGGNPCTCQPQAFLGWSVDSCLQGDRCN--IFANFILHDVNSGTTCSTDLQKSNTDII
CRCVspikepr   DYCGGNPCTCQPKAFLGWSVDSCLQGDRCN--IFANFILHGVNSGTTCSTDLQKSNTDII
HEVspikepro   DDCSGNPCTCKPQAFIGWSSETCLQNGRCN--IFANFILNDVNSGTTCSTDLQQGNTNIT
CECVspikepr   NFNQDCTDVLYATAVIKTGTCPFSFDKLNNYLTFNKLCLSLNPTGANCKFDVAARTRTNE
              :     . . . . *.: . .  .  *   *  :: *      :*:.*. *:   .

BCVspikepro   LGVCVNYDLYGITGQGIFVEVNATYYNSWQNLLYDSNGNLYGFRDYLTNRTFMIRSCYSG
HCVspikepro   LGVCVNYDLYGITGQGIFVEVNAPYYNSWQNLLYDSNGNLYGFRDYLTNRTFMIRSCYSG
CRCVspikepr   LGVCVNYDLYGITGQGIFVEVNATYYNSWQNLLYDSNGNLYGFRDYLTNRTFMIRSCYSG
HEVspikepro   TDVCVNYDLYGITGQGILIEVNATYYNSWQNLLYDSSGNLYGFRDYLSNRTFLIRSCYSG
CECVspikepr   QVVRSLYVIYEEGDNIVGVPSDNSGLHDLSVLHLDSCTDYN---IYGRTGVGIIRQTNST
              *   *  :* .:   :  : .  :. . *  **   :     *  . . :**. *

692  ╱695
BCVspikepro   RVSAAFHANSSEPALLFRNIKCNYVFNNTLSRQLQPINYFDSYLGCVVNADNSTSSAVQT
HCVspikepro   RVSAAFHANSSEPALLFRNIKCSYVFNNTLSRQLQPINYFDSYLGCVVNADNSTSSVVQT
CRCVspikepr   RVSAGFHSNSSEPALLFRNIKCNYVFNNTLSRQLQPINYFDSYLGCVVNADNSTSSSVQT
HEVspikepro   RVSAVFHANSSEPALMFRNLKCSHVFNYTILRQIQLVNYFDSYLGCVVNAYNNTASAVST
CECVspikepr   ILSGLHYTSLSGDLLGFKNVSDGVVYSVTPCDVSAQAAVIDGAIVGAMTSINSELLGLTH
              :*. .::. *   * *:*:.. .*:. *       :*. :  .:.: *.    :

757 758 763 769            ╱786
BCVspikepro   CDLTVGSGYCVDYSTKRRSRRAITTGYRFTNFEPFTVNS----------------VNDS
HCVspikepro   CDLTVGSGYCVDYSTKRRSRRAITTGYRFTNFEPFTVNS----------------VNDS
CRCVspikepr   CDLTVGSGYWGDYSTQRRSRRTITTGYRFTNFEPFTVNP----------------VNDS
HEVspikepro   CDLTVGSGYCVDYVTALRSRRSFTTGYRFTNFEPFAANL----------------VNDS
CECVspikepr   WTTTPNFYYYSIYNTTNERTRGTAIDSNDVDCEPIITYSNIGVCKNGALVFINVTHSDGD
              *  .    *  * * .  *  :. ...: **: .                    :..

╱792                    ╱818 827 ╱828
BCVspikepro   LEPVGGLYEIQIPSEFTIGNMEEFIQISSPKVTIDCSAFVCGDYAACKSQLVEYGSFCDN
HCVspikepro   LEPVGGLYEIQIPSEFTIGNMEEFIQTSSPKVTIDCSAFVCGDYAACKSQLVEYGSFCDN
CRCVspikepr   LHPVGGLYEIQIPSEFTIGNMEEFIQTRSPKVTIDCPVFVCGDYAACKSQLVEYGSFCDN
HEVspikepro   IEPVGGLYEIQIPSEFTIGNLEEFIQTSSPKVTIDCATFVCGDYAACRQQLAEYGSFCEN
CECVspikepr   VQPIS-TGNVTIPTNFTISVQVEYIQVYTTPVSIDCSRYVCNGNPRCNKLLTQYVSACQT
              :..*:.   ::  **::***.  *:** . *:***. :**. . *.. *.:* * *:.
```

FIGURE 10 (Page 4 of 5)

```
                                                                 887
BCVspikepro    INAILTEVNELLDTTQLQVANSLMNGVTLSTKLKDGVNFNVDDIN----------FSPVL
HCVspikepro    INAILTEVNELLDTTQLQVANSLMNGVTLSTKLKDGVNFNVDDIN----------FSPVL
CRCVspikepr    INAILTEVNELLDTTQLQVANSLMNGVTLSTKLKDGFNFNVDDIN----------FSPVL
HEVspikepro    INAILIEVNELLDTTQLQVANSLMNGVTLSTKIKDGINFNVDDIN----------FSSVL
CECVspikepr    IEQALAMSASLENMEVDSMLFVSENALKLASVEAFNSTEHLDPIYKEWPNIGGSWLGGLK
               *:  *    .* :     .:     *.:.*::    . . ::* *           :. :

933
BCVspikepro    GCLGSDCNKVSSRSAIEDLLFSKVKLSDVG-FVEAYNNCTGGAEIRDLICVQSYNGIKVL
HCVspikepro    GCLGSACNKVSSRSAIEDLLFSKVKLSDVG-FVEAYNNCTGGAEIRDLICVQSYNGIKVL
CRCVspikepr    GCLGSECNKVSSRSAIEDLLFSKVKLSDVG-FVDAYNNCTGGAEIRDLICVQSYNGIKVL
HEVspikepro    GCLGSECNRASTRSAIEDLLFDKVKLSDVG-FVQAYNNCTGGAEIRDLICVQSYNGIKVL
CECVspikepr    DILPSHNSKRKYRSAIEDLLFDKVVTSGLGTVDEDYKRCTGGYDIADLVCAQYYNGIMVL
               . * *  .: . *********.**  *.:* . : *:.**** :* **:*.* **** **

977                                1011 1018
BCVspikepro    PPLLSENQISGYTLAATSASLFPPWS-AAAGVPFYLNVQYRINGIGVTMDVLSQNQKLIA
HCVspikepro    PPLLSVNQISGYTLAATSASLFPPWS-AAAGVPFYLNVQYRINGIGVTMDVLSQNQKLIA
CRCVspikepr    PPLLSENQISGYTLAATFASLFPPWS-AAAGVPFYLNVQYRINGIGVTMDVLTQNQKLIS
HEVspikepro    PPLLSENQISGYTSAATAASLFPPWT-AAAGVPFYLNVQYRINGLGVTMDVLSQNQKLIA
CECVspikepr    PGVANDDKMTMYTASLAGGIALGALGGGAVAIPFAVAVQARLNYVALQTDVLNKNQQILA
               * : . :::: ** : : .  : .   .*..:** : ** *:* :.:  ***.:**::::

1063
BCVspikepro    NAFNNALDAIQEGFDATN--------------SALVKIQAVVNANAEALNNLLQQLSNRF
HCVspikepro    NAFSNALDAIQEGFDATN--------------SALVKIQAVVNANAEALNNLLQQLSNRF
CRCVspikepr    NAFNNALDAIQEGFDATN--------------SALVKIQAVVNANAEALNNLLQQLSNKF
HEVspikepro    SAFNNALDSIQEGFDATN--------------SALVKIQAVVNANAEALNNLLQQLSNRF
CECVspikepr    NAFNQAIGNITQAFGKVNDAIHQTSQGLATVAKALAKVQDVVNTQGQALSHLTVQLQNSF
               .**.:*:. * :.*. .*              .**.*:* ***::.:**.:*  **.* *

BCVspikepro    GAISSSLQEILSRLDALEAQAQIDRLINGRLTALNAYVSQQLSDSTLVKFSAAQAMEKVN
HCVspikepro    GAIGSSLQEILSRLDALEAQAQIDRLINGRLTALNAYVSQQLSDSTLVKFSAAQAMEKVN
CRCVspikepr    GAISASLQEILSRLDALEAQAQIDRLINGRLTALNAYVSQQLSDSTLVKFSAAQAMEKVN
HEVspikepro    GAISASLQEILSRLDALEAKAQIDRLINGRLTALNAYVSQQLSDSTLVKFSAAQAIEKVN
CECVspikepr    QAISSSISDIYNRLDELSADAQVDRLITGRLTALNAFVSQTLTRQAEVRASRQLAKDKVN
                **.:*:.:* .*** *.*.**:****.********:*** *: .: *: *    * :***
```

FIGURE 10 (Page 5 of 5)

```
BCVspikepro   ECVKSQSSRINFCGNGNHIISLVQNAPYGLYFIHFSYVPTKYVTAKVSPGLCIAGDRGIA
HCVspikepro   ECVKSQSSRINFCGNGNHIISLVQNAPYGLYFIHFSYVPTKYVTAKVSPGLCIAGDRGIA
CRCVspikepr   ECVKSQSSRINFCGNGNHIISLVQNAPYGLYFIHFSYVPTKYVTAKVSPGLCIAGDRGIA
HEVspikepro   ECVKSQSSRINFCGNGNHIISLVQNAPYGLYFIHFSYVPTKYVTAKVSPGLCIAGDIGIS
CECVspikepr   ECVRSQSQRFGFCGNGTHLFSLANAAPNGMVFFHTVLLPTAYETVTAWSGICASDGDRTF
              ***:***.*:.*****.*::**.: ** *: *:*    :** * *..  .*:* :..

BCVspikepro   ------PKSGYFVNVNNTWMFTGSGYYYPEPITGNNVVVMSTCAVNYTKAPDVMLNISTP
HCVspikepro   ------PKSGYFVNVNNTWMFTGSGYYYPEPITGNNVVVMSTCAVNYTKAPDVMLNISTP
CRCVspikepr   ------PKSGYFVNVNNTWMFTGSGYYYPEPITGNNVVVMSTCAVNYTKAPDVMLNISTP
HEVspikepro   ------PKSGYFINVNNSWMFTGSGYYYPEPITQNNVVVMSTCAVNYTKAPDLMLNTSTP
CECVspikepr   GLVVKDVQLTLFRNLDDKFYLTPRTMYQPRAATSSDFVQIEGCDVLFVNATVIDLPSIIP
                    :  *  *::::.: :*    *  *..  *  .:..*  :.  * * :.:*.  : *    *
                              1256\       /1257
BCVspikepro   NLPDFKEELDQWFKNQTS--VAPDLSLDYINVTFLDLQDEMN--------------RLQE
HCVspikepro   NLHDFKEELDQWFKNQTS--VAPDLSLDYINVTFLDLQDEMN--------------RLQE
CRCVspikepr   NLPDFKEELDQWFKNQTL--MAPDLSLDYINVTFLDLQDEMN--------------RLQE
HEVspikepro   NLPDFKEELYQWFKNQSS--LAPDLSFDYINVTFLDLQDEMN--------------RLQE
CECVspikepr   DYIDINQTVQDILENYRPNWTVPELTIDIFNATYLNLTGEIDDLEFRSEKLHNTTVELAI
              :  *:::  : : ::*      .*:*:.*  :*.*:*:* .*::                .*

BCVspikepro   AIKVLNQSYINLKDIGTYEYYVKWPWYVWLLIGLAGVAMLVLLFFICCCTGCGTSCFKKC
HCVspikepro   AIKVLNQSYINLKDIGTYEYYVKWPWYVWLLIGFAGVAMLVLLFFICCCTGCGTSCFKIC
CRCVspikepr   AIKVLNHSYINLKDIGTYEYYVKWPWYVWLLIGLAGVAMLVLLFFICCCTGCGTSCFKKC
HEVspikepro   AIKVLNHSYINLKDIGTYEYYVKWPWYVWLLICLAGVVMLVLLFFICCCTGCGTSCFKKC
CECVspikepr   LIDNINNTLVNLEWLNRIETYVKWPWYVWLLIGLVVVFCIPLLLFCCCSTGCCG-CIGCL
              *. :*:: :**: :.  * ************ :. *   : **:* **.*** *:

BCVspikepro   GGCCDDYTGHQELVIKTSHDD---------------------------------
HCVspikepro   GGCCDDYTGHQELVIKTSHDD---------------------------------
CRCVspikepr   GGCCDDYTGHQELVIKTSHDD---------------------------------
HEVspikepro   GGCFDDYTGHQEFVIKTSHDD---------------------------------
CECVspikepr   GSCCHSICSRRQFENYEPIEKVHVH-----------------------------
              *.*  ..  .:::: 	. :.
```

FIGURE 13

```
TATCGCAGCC TTACTTTTGT TAATGTACCA TATGTTTATA ATGGCTCTGC ACAATCTACA   60
GCTCTTTGTA AATCTGGTAG TTTAGTTCTT AATAACCCTG CATATATAGC TCGTGAAGCT  120
AATTTTGGGG ATTATTATTA TAAGGTTGAA GCTGATTTCT ATTTGTCAGG TTGTGACGAG  180
TATATCGTAC CACTTTGTAT TTTTAACGGC AAGTTTTGT CGAATACAAA GTATTATGAT  240
GATAGTCAAT ATTATTTAA TAAAGACACT GGTGTTATTT ATGGTTTCAA TTCTACTGAA  300
ACCATTAACA CTGGTTTTGA TTTTAATTGT CATTATTTAC TTTTACCCTC TGGTAATTAT  360
TTAGCCATTT CAAATGAGCT ATTGTTAACT GTTCCTACGA AGCAATCTG TCTTAATAAG  420
CGTAAGGATT TTACGCCTGT ACAGGTTGTT GACTCGCGGT GGAACAATGC CAGGCAGTCT  480
GATAACATGA CGGCGG                                                  497
```

FIGURE 14

```
YRSLTFVNVP YVYNGSAQST ALCKSGSLVL NNPAYIAREA NFGDYYKVE  ADFYLSGCDE   60
YIVPLCIFNG KFLSNTKYYD DSQYYFNKDT GVIYGFNSTE TINTGFDFNC HYLLLPSGNY  120
LAISNELLLT VPTKAICLNK RKDFTPVQVV DSRWNNARQS DNMTA                  165
```

FIGURE 15 (Page 1 of 2)

```
CRCV    TATCGCAGCCTTACTTTTGTTAATGTACCATATGTTTATAATGGCTCTGCACAATCTACA
BCV     TATCGCAGCCTTACTTTTGTTAATGTACCATATGTTTATAATGGCTCTGCACAATCTACA
OC43    TATCGCAGCCTTACTTTTGTTAATGTACCATATGTTTATAATGGCTCTGCACAATCTACA
HECV    TATCGCAGCCTTACTTTTGTTAATGTACCATATGTTTACAATGGCTCTGCACAATCTACA
HEV     TATCGCAGTCTTACTTTAGTTAATGTGCCATACGTTTACAATGGGTCAGCTCAACCCACC
        ******* ******* ******* ***** ***** ***** ** ** *** * **

CRCV    GCTCTTTGTAAATCTGGTAGTTTAGTTCTTAATAACCCTGCATATATAGCTCGTGAAGCT
BCV     GCTCTTTGTAAATCTGGTAGTTTAGTTCTTAATAACCCTGCATATATAGCTCGTGAAGCT
OC43    GCTCTTTGTAAATCTGGTAGTTTAGTCCTTAATAACCCTGCATATATAGCTCCTCAAGCT
HECV    GCTCTTTGTAAATCTGGTAGTTTAGTTCTTAATAACCCTGCATATATAGCTCGTGAAGCT
HEV     GCACTTTGTAAGTCTGGCAGTTTAATTCTTAACAATCCTGCATATATAGCCCGTGAGGCT
        ** ******** ***** ****** * ***** ** ************* * * * ***

CRCV    AATTTTGGGGATTATTATTATAAGGTTGAAGCTGATTTCTATTTGTCAGGTTGTGACGAG
BCV     AATTTTGGGGATTATTATTATAAGGTTGAAGCTGATTTTTATTTGTCAGGTTGTGACGAG
OC43    AACTCTGGGGATTATTATTATAAGGTTGAAGCTGATTTTTATTTGTCAGGTTGTGACGAG
HECV    AATTTTGGGGATTATTATTATAAGGTTGAAGCTGATTTTTATTTGTCAGGTTGTGACGAG
HEV     AATGTGGGTGATTATTATTATAAGTCTGAAGCAGATTTTTCTCTCTCAGGTTGTGACGAG
        **    ** ************** * ***** ***** * * * ****************

CRCV    TATATCGTACCACTTTGTATTTTTAACGGCAAGTTTTTGTCGAATACAAAGTATTATGAT
BCV     TATATCGTACCACTTTGTATTTTTAACGGCAAGTTTTTGTCGAATACAAAGTATTATGAT
OC43    TATATCGTACCACTTTGTATTTTTAACGGCAAGTTTTTGTCGAATACAAAGTATTATGAT
HECV    TATATCGTACCACTTTGTATTTTTAACGGCAAGTTTTTGTCGAATACAAAGTATTATGAT
HEV     TATATCGTACCACTTTGTATTTTTAATGGCAAGTTTTTGTCGAATACAAAGTATTATGAT
        ************************** *********************************

CRCV    GATAGTCAATATTATTTTAATAAAGACACTGGTGTTATTTATGGTTTCAATTCTACTGAA
BCV     GATAGTCAATATTATTTTAATAAAGACACTGGTGTTATTTATGGTCTCAATTCTACTGAA
OC43    GATAGTCAATATTATTTTAATAAAGACACTGGTGTTATTTATGGTCTCAATTCTACAGAA
HECV    GATAGTCAATATTATTTTAATAAAGACACTGGTGTTATTTATGGTCTCAATTCTACTGAA
HEV     GATAGTCAATATTATTTTAATAAAGACACTGGTGTTATTTATGGTCTCAATTCTACTGAA
        ********************************************* ********** ***

CRCV    ACCATTAACACTGGTTTTGATTTTAATTGTCATTATTTACTTTTACCCTCTGGTAATTAT
BCV     ACCATTACCACTGGTTTTGATTTTAATTGTCATTATTTAGTTTTACCCTCTGGTAATTAT
OC43    ACCATTACCACTGGTTTTGATCTTAATTGTTATTATTTAGTTTTACCCTCTGGTAATTAT
HECV    ACCATTACCACTGGTTTTGATTTTAATTGTCATTATTTAGTTCTACCCTCTGGCAATTAT
HEV     ACCATTACCACTGGTTTTGATTTTAATTGTCATTATTTAGTTCTACCCTCTGGTAATTAT
        ******  ************* ******** ******** ** ********* ******

CRCV    TTAGCCATTTCAAATGAGCTATTGTTAACTGTTCCTACGAAAGCAATCTGTCTTAATAAG
BCV     TTAGCCATTTCAAATGAGCTATTGTTAACTGTTCCTACGAAAGCAATCTGTCTTAATAAG
OC43    TTAGCCATTTCAAATGAGCTATTGTTAACTGTTCCTACGAAAGCAATCTGTCTTAATAAG
HECV    TTAGCCATTTCAAATGAGCTATTGTTAACTGTTCCTACTAAAGCAATCTGTCTTAATAAG
HEV     CTAGCCATTTCAAATGAGCTATTGTTAACTGTTCCTACTAAAGCAATCTGTCTTAATAAG
         ************************************ *********************
```

FIGURE 15 (Page 2 of 2)

```
CRCV    CGTAAGGATTTTACGCCTGTACAGGTTGTTGACTCGCGGTGGAACAATGCCAGGCAGTCT
BCV     CGTAAGGATTTTACGCCTGTACAGGTTGTTGACTCTCGGTGGAACAATGCCAGGCAGTCT
OC43    CGTAAGGATTTTACGCCTGTACAGGTTGTTGATTCGCGGTGGAACAATGCCAGGCAGTCT
HECV    CGTAAGGATTTTACGCCTGTACAGGTTGTTGACTCGCGGTGGAACAATGCCAGGCAGTCT
HEV     CGTAAGGTTTTTACGCCTGTACAGGTTGTTGATTCGCGGTGGAACAATGCCAGGCAATCT
        ****** ********************* ** ******************** ***

CRCV    GATAACATGACGGCGGT
BCV     GATAACATGACGGCGGT
OC43    GATAACATGACGGCGGT
HECV    GATAACATGACGGCAGT
HEV     GATAACATGACGGCAGT
        ************* **
```

FIGURE 16

```
CRCV    YRSLTFVNVPYVYNGSAQSTALCKSGSLVLNNPAYIAREANFGDYYYKVEADFYLSGCDE
BCV     YRSLTFVNVPYVYNGSAQSTALCKSGSLVLNNPAYIAREANFGDYYYKVEADFYLSGCDE
OC43    YRSLTFVNVPYVYNGSAQSTALCKSGSLVLNNPAYIAPQANSGDYYYKVEADFYLSGCDE
HECV    YRSLTFVNVPYVYNGSAQSTALCKSGSLVLNNPAYIAREANFGDYYYKVEADFYLSGCDE
HEV     YRSLTLVNVPYVYNGSAQPTALCKSGSLILNNPAYIAREANVGDYYYKSEADFSLSGCDE
        *****:************ ********:******** :** ****** **** ******

CRCV    YIVPLCIFNGKFLSNTKYYDDSQYYFNKDTGVIYGFNSTETINTGFDFNCHYLLLPSGNY
BCV     YIVPLCIFNGKFLSNTKYYDDSQYYFNKDTGVIYGLNSTETITTGFDFNCHYLVLPSGNY
OC43    YIVPLCIFNGKFLSNTKYYDDSQYYFNKDTGVIYGLNSTETITTGFDLNCYYLVLPSGNY
HECV    YIVPLCIFNGKFLSNTKYYDDSQYYFNKDTGVIYGLNSTETITTGFDFNCHYLVLPSGNY
HEV     YIVPLCIFNGKFLSNTKYYDDSQYYFNKDTGVIYGLNSTETITTGFDFNCHYLVLPSGNY
        ********************************** :****** .****:**:**:******

CRCV    LAISNELLLTVPTKAICLNKRKDFTPVQVVDSRWNNARQSDNMTA
BCV     LAISNELLLTVPTKAICLNKRKDFTPVQVVDSRWNNARQSDNMTA
OC43    LAISNELLLTVPTKAICLNKRKDFTPVQVVDSRWNNARQSDNMTA
HECV    LAISNELLLTVPTKAICLNKRKDFTPVQVVDSRWNNARQSDNMTA
HEV     LAISNELLLTVPTKAICLNKRKVFTPVQVVDSRWNNARQSDNMTA
        ********************* **********************
```

CANINE RESPIRATORY CORONAVIRUS (CRCV) SPIKE PROTEIN, POLYMERASE AND HEMAGGLUTININ/ESTERASE

This application is U.S. National Phase of International Application PCT/ GB2003/002832, filed Jul. 1, 2003 designating the U.S., and published in English as WO 2004/011651 on Feb. 5, 2004, which claims priority to United Kingdom Patent Application No. 0217434.0 filed Jul. 27, 2002.

FIELD OF THE INVENTION

The present invention relates to biological material, and in particular to a canine respiratory coronavirus that is present in dogs having canine infectious respiratory disease.

BACKGROUND OF THE INVENTION

Canine infectious respiratory disease (CIRD) is a highly contagious disease common in dogs housed in crowded conditions such as re-homing centres and boarding or training kennels. Many dogs suffer only from a mild cough and recover after a short time, however in some cases a severe bronchopneumonia can develop (Appel and Binn, 1987).

The pathogenesis of CIRD is considered to be multifactorial, involving several viruses and bacteria. The infectious agents considered to be the major causative pathogens of CIRD are canine parainfluenzavirus (CPIV) (Binn et al., 1967), canine adenovirus type 2 (CAV-2) (Ditchfield et al., 1962) and the bacterium *Bordetella bronchiseptica* (Bemis et al., 1977, Keil et al., 1998). Also, canine herpesvirus, human reovirus and mycoplasma species have been isolated from dogs with symptoms of CIRD (Karpas et al., 1968, Lou and Wenner 1963, Randolph et al., 1993) Additional factors like stress may also be important.

CIRD is rarely fatal but it delays re-homing of dogs at rescue centres and it causes disruption of schedules in training kennels as well as considerable treatment costs.

Vaccines are available against some of the infectious agents associated with this disease, namely *Bordetella bronchiseptica* as well as CPIV and CAV-2. However, despite the use of these vaccines, CIRD is still prevalent in kennels world-wide, which is possibly due to the vaccines not providing protection against all the infectious agents involved in CIRD.

We have discovered a novel coronavirus, which we have called canine respiratory coronavirus (CRCV), in a large kenneled dog population with a history of endemic respiratory disease, and we have shown that this virus is associated with CIRD.

Some members of the family coronaviridae are known to cause respiratory disease in humans, cattle, swine and poultry (Mäkelä et al., 1998, Pensaert et al., 1986, Ignjatovic and Sapats 2000). For example, bovine respiratory coronavirus is associated with shipping fever in cattle which is a multifactorial respiratory disease (Storz et al., 2000).

However, coronaviruses were not suspected to have a role in the pathogenesis of CIRD. Indeed, with only a single exception, canine coronaviruses have been reported to be enteric viruses and to cause acute diarrhoea mainly in young dogs (for example, Tennant et al., 1993). In a large study of viruses involved in canine respiratory diseases, Binn et al. (1979) reported the detection of a canine coronavirus in the lung of a single dog that was also infected with SV5 and canine adenovirus 2, two other viruses that are associated with canine respiratory disease.

There are 30-40 dog vaccines commercially available in the UK for use against a number of pathogens that can cause a range of diseases, such as neurological, enteric, hepatic and respiratory diseases. Most of these vaccines contain microbial agents such as Distemper virus, Canine Adenovirus-2, Canine parvovirus, canine parainfluenza virus and *Leptospira canicola* and *L. icterohaemorrhagiae*. None of these vaccines contain canine coronaviruses.

The dog vaccines for use against canine respiratory diseases are marketed as vaccines for "kennel-cough" (see below). All of the vaccines contain *Bordetella bronchisepticum*, which is a bacterium associated with "kennel cough".

Coyne M. J. & May S. W., (1995) in their article entitled "Considerations in using a canine coronavirus vaccine" (published as a Pfizer Technical Bulletin on the Internet at http://www.pfizer.com/ah/vet/tref/trbull/ccv.html), lists over 20 commercially available vaccines against either canine coronaviruses alone or against canine coronaviruses together with other organisms. Each of these vaccines is for canine enteric disease, and there is no suggestion that a canine coronavirus may be associated with respiratory disease.

U.S. Pat. Nos. 6,057,436 and 6,372,224, both to Miller et al and assigned to Pfizer, Inc., describe the spike gene of the enteric canine coronavirus and uses therefor, including its use as a vaccine against gastroenteritis. Neither of these two patents suggest that a canine coronavirus may be involved in CIRD.

Members of the family coronaviridae are enveloped viruses, 80-160 nm in diameter, containing a linear positive-stranded RNA genome. The structural proteins of coronaviruses are the spike glycoprotein (S), the membrane glycoprotein (M) and the nucleocapsid protein (N). The hemagglutinin/esterase glycoprotein (HE) is found only on the surface of group II coronaviruses (e.g. bovine coronavirus and murine hepatitis virus) (Spaan et al, 1988). Further details of the structure of coronoviruses may be found in the chapter by Cavanagh et al entitled "Coronviridae" p 407-411, in "Virus Taxonomy, 6*th* Report of the International Committee on Taxonomy of Viruses", pub. Springer-Verlag Wein, New York, Eds. Murphy et al, which is incorporated herein by reference.

SUMMARY OF THE INVENTION

The canine respiratory coronavirus (CRCV) of the invention may be characterised as a coronavirus present in the respiratory tracts of dogs with infectious respiratory disease. To further characterise CRCV, we have determined the sequence of 250 nucleotide residues of the CRCV polymerase (pol) cDNA (FIG. 1 and SEQ ID NO: 1) which corresponds to an 83 amino acid partial sequence of the pol protein (FIG. 2 and SEQ ID NO: 2). We have also cloned and determined the sequence of the 4092 nucleotide residues of the CRCV spike (S) cDNA (FIG. 3 and SEQ ID NO: 3), corresponding to 1363 amino acids (FIG. 4 and SEQ ID NO: 4). We have also determined the sequence of 497 nucleotide residues of the CRCV hemagglutinin/esterase (HE) gene (FIG. 13 and SEQ ID NO: 21), corresponding to 165 amino acids (FIG. 14 and SEQ ID NO: 22). We have identified that CRCV has a surprisingly low homology to the enteric canine coronavirus (CCV) while it has an unexpectedly high level of homology to bovine coronavirus (strain LY138 or Quebec) and human coronavirus (strain OC43).

A culture of "Spike D-1 CRCV", which is XL1-Blue *E. coli* (Stratagene) containing a pT7Blue2 plasmid (Novagen) whose insert contains a portion of the CRCV spike cDNA, has been deposited under the Budapest Treaty at NCIMB Ltd under Accession number NCIMB 41146 on 25 Jul. 2002. The depositor of NCIMB 41146 is the Royal Veterinary College, Royal College Street, London NW1 OTU, UK. The address of NCIMB Ltd is 23 St. Machar Drive, Aberdeen, Scotland, AB24 3RY, UK.

This assures maintenance of a viable culture of the deposit for 30 years from date of deposit. The deposit will be made available by NCIMB under the terms of the Budapest Treaty, and subject to an agreement between Applicant and NCIMB which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strain is not to be construed as a license to practice the invention in contravention of the rights granted under the authority of any government in accordance with its patent laws.

The phylogenetic relationship of CRCV to eleven known coronaviruses was determined based upon a comparison of the 250 nucleotide sequence from the CRCV pol gene and the corresponding regions of the other viruses (FIG. 5). The bovine coronavirus (BCV), human coronavirus (HCV) strain OC43 and hemagglutinating encephalomyelitis virus (HEV) were found to be most closely related to CRCV, while the enteric CCV was found to be only distantly related to CRCV.

Over the 250 sequenced residues of the pol cDNA, corresponding to 83 amino acids, CRCV has only 68.5% and 75.9% sequence identity at the nucleotide and amino acid levels, respectively, with the equivalent region of the enteric CCV (strain 1-71) pol gene (Genbank Accession No. AF124986), as shown in FIGS. 6 and 7.

Over the 4092 sequenced nucleotide residues of the CRCV S gene, corresponding to 1363 amino acids, CRCV has 45% and 21.2% sequence identity at the nucleotide (FIG. 8) and amino acid levels, respectively, with the equivalent region of the enteric CCV (strain 1-71) S gene.

Enteric CCV is not a group II coronavirus and does not possess an HE gene, hence it is not possible to determine the extent of sequence identity between this gene in CRCV and in enteric CCV.

Except as described below, the percentage identity between two nucleotide or two amino acid sequences was determined using FASTA version 34 (Pearson W R. (1990) "Rapid and sensitive sequence comparison with FASTP and FASTA". *Methods Enzymol.;* 183:63-98). FASTA settings were Gap open penalty −16 and Gap extension penalty −4.

The percentage identity between the CRCV and enteric CCV spike sequences was determined using GCG version 10 (Genetics Computer Group, (1991), Program Manual for the GCG Package, Version 7, April 1991, 575 Science Drive, Madison, Wis., USA 53711). The GCG parameters used were: Gap creation penalty 50, gap extension penalty 3 for DNA, and Gap creation penalty 8 and Gap extension penalty 2 for Protein.

Sequence alignments were performed using ClustalX (Thompson et al., 1997).

By contrast, over the 250 sequenced residues of the pol cDNA, CRCV has 98.8% sequence identity with the equivalent region of the BCV strain Quebec pol gene (Genbank Accession No. AF220295), 98.4% sequence identity with the BCV strain LY138 pol gene (Genbank Accession No. AF124985) and 98.4% sequence identity with the HCV OC43 pol gene (Genbank Accession No. AF124989).

There was only a single amino acid difference between the CRCV pol protein over the 83 sequenced amino acids and the BCV, HCV and HEV pol proteins which is that CRCV has E (Glu) as opposed to D (Asp) at the position corresponding to position 4975 in the BCV genome (Accession No. SWALL: Q91A29). Thus the CRCV pol protein is 99% identical to the BCV, HCV and HEV pol proteins over this region.

The one and three letter amino acid codes of the IUPAC-IUB Biochemical Nomenclature Commission are used herein.

Over the 497 sequenced nucleotide residues, corresponding to 165 amino acids, of the HE gene, CRCV has 98.994% and 98.2% sequence identity with the equivalent region of the BCV strain LY138 HE gene (Genbank Accession No. AF058942) at the nucleotide and amino acid levels respectively. CRCV has 98.189% (nucleotide) and 98.2% (amino acid) sequence identity with human enteric coronavirus (HECV) HE gene (Genbank Accession No. L07747); 97.4% (nucleotide) and 95.2% (amino acid) sequence identity with the HCV OC43 HE gene (Genbank Accession No. M76373); and 92.0% (nucleotide) and 93.9% (amino acid) identity with HEV (Genbank Accession Nos. AF481863), as shown in FIGS. 15 and 16.

As shown in FIG. 16 and Table 3, the three amino acids that are different between the CRCV HE protein and each of the BCV, HECV, HCV and HEV S proteins, within the 165 amino acids of the CRCV HE protein, are F (Phe) as opposed to L (Leu), N (Asn) as opposed to T (Thr), and L (Leu) as opposed to V (Val) at positions corresponding to position 235, 242 and 253, respectively, in the BCV, HECV, HCV OC43 and HEV HE genes (FIG. 16). Thus F at position 235, N at position 242 and L at position 253 could be said to be CRCV HE protein-specific amino acids.

Over the 4092 sequenced nucleotide residues, corresponding to 1363 amino acids, of the CRCV S gene, CRCV has 97.3% and 96% identity with the equivalent region of BCV strain LY138 (Genbank Accession No. AF058942) at the nucleotide and amino acid levels respectively. CRCV has 96.9% (nucleotide) and 95.2% (amino acid) identity with HCV strain OC43 (Genbank Accession No. Z32768), and 83.8% (nucleotide) and 80.4% (amino acid) identity with HEV (Genbank Accession Nos. AF481863 (cDNA) and AAM 77000 (protein)) as shown in FIGS. 9 and 10.

The amino acids that are different between the CRCV S protein and each of the BCV, HCV and HEV S proteins, within the 1363 amino acids of the CRCV S protein, are listed in Table 1 below. Thus the amino acids listed in Table 1 could be said to be CRCV S protein-specific amino acids. The amino acids are numbered from the initial M residue at the start of the CRCV protein, as shown in FIG. 4.

TABLE 1

List of 39 amino acids specific to the CRCV S protein that are not present in the BCV, HCV and HEV S proteins.

| Position | Amino Acid |
|---|---|
| 103 | V |
| 118 | V |
| 166 | D |
| 171 | M |
| 179 | K |
| 192 | P |
| 210 | S |
| 235 | H |
| 267 | F |
| 388 | F |
| 407 | M |

TABLE 1-continued

List of 39 amino acids specific to the CRCV S protein that are
not present in the BCV, HCV and HEV S proteins.

| Position | Amino Acid |
|---|---|
| 436 | S |
| 440 | I |
| 447 | I |
| 501 | F |
| 525 | Y |
| 528 | N |
| 540 | L |
| 582 | K |
| 608 | G |
| 692 | G |
| 695 | S |
| 757 | W |
| 758 | G |
| 763 | Q |
| 769 | T |
| 786 | P |
| 792 | H |
| 818 | R |
| 827 | P |
| 828 | V |
| 887 | F |
| 933 | D |
| 977 | F |
| 1011 | T |
| 1018 | S |
| 1063 | K |
| 1256 | L |
| 1257 | M |

A first aspect of the invention provides a coronavirus S protein, or fragment thereof, having at least 75% amino acid sequence identity with the CRCV S protein whose amino acid sequence is listed in FIG. 4, and having at least one of V at position 103; V at position 118; D at position 166; M at position 171; K at position 179; P at position 192; S at position 210; H at position 235; F at position 267; F at position 388; M at position 407; S at position 436; I at position 440; I at position 447; F at position 501; Y at position 525; N at position 528; L at position 540; K at position 582; G at position 608; G at position 692; S at position 695; W at position 757; G at position 758; Q at position 763; T at position 769; P at position 786; H at position 792; R at position 818; P at position 827; V at position 828; F at position 887; D at position 933; F at position 977; T at position 1011; S at position 1018; K at position 1063; L at position 1256; and M at position 1257. The amino acids are numbered from the initial M at the start of the CRCV S protein, as listed in FIG. 4 (SEQ ID NO: 4).

It is appreciated that the partial nucleotide sequence of CRCV S can be readily determined by a person or ordinary skill in the art by sequencing the insert of the plasmid contained in E. coli strain D-1 CRCV, that has been deposited under the Budapest Treaty at NCIMB Ltd. under Accession number NCIMB 41146 on 25 Jul. 2002. Furthermore, this DNA can be used as a hybridisation probe, or as the basis for the design of probes, in the isolation of CRCV nucleic acid in dogs.

For the avoidance of doubt, the invention includes a coronavirus S protein, or fragment thereof, having at least 75% amino acid sequence identity with the CRCV S protein (SEQ ID NO: 4), and comprising at least one of the amino acids specific for the CRCV S protein at the position listed in Table 1.

By "protein" we also include the meaning glycoprotein. The amino acid sequence of a glycoprotein refers to the amino acid sequence of the polypeptide backbone of the glycoprotein, irrespective of the type, number, sequence and position of the sugars attached thereto.

Typically, the invention includes an isolated or recombinant protein, and not an unmodified CRCV protein present as a CRCV component.

The invention includes a coronavirus S protein, or fragment thereof, having at least 76% amino acid sequence identity with the CRCV S protein (SEQ ID NO: 4), or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% amino acid sequence identity with the CRCV S protein, and comprising at least one of the amino acids specific for the CRCV S protein at the position listed in Table 1.

The invention also includes a coronavirus S protein, or fragment thereof, having at least 75%, or at least 80%, or at least 85% or at least 90% or at least 95% amino acid sequence identity with the CRCV S protein (SEQ ID NO: 4), and comprising at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30, or at least 31, or at least 32, or at least 33, or at least 34, or at least 35, or at least 36, or at least 37, or at least 38 of the amino acids specific for CRCV S protein at the positions listed in Table 1.

Preferably, the coronavirus S protein, or fragment thereof comprises all 39 of the amino acid residues specific for CRCV S protein at the positions listed in Table 1.

Thus the invention includes a BCV, HCV or HEV S protein or fragment thereof, that has been modified at least one position listed in Table 1 to resemble the CRCV S protein.

Preferably, the coronavirus S protein of the invention is a CRCV S protein that comprises or consists of the sequence listed in FIG. 4 (SEQ ID NO: 4), or a variant thereof with at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Thus the variant of the coronavirus S protein of the invention includes a protein that comprises or consists of the sequence listed in FIG. 4 (SEQ ID NO: 4) but has between 1 and 40 amino acid differences from the sequence listed in FIG. 4. Preferably, the variant has less than 40 amino acid differences from the sequence listed in FIG. 4. More preferably the variant has less than 35, less than 30, or less than 25, or less than 20, or less than 15, or 10 or 9 or 8 or 7 or 6 or 5 or 4 or 3 or 2 amino acid differences, or a single amino acid difference, from the sequence listed in FIG. 4.

The invention also includes a CRCV S protein fragment comprising a fragment of the sequence listed in FIG. 4 (SEQ ID NO: 4) which comprises at least one of the amino acids specific for CRCV S protein at the position listed in Table 1.

The invention includes a coronavirus S protein, or fragment thereof, having at least 75% amino acid sequence identity with BCV strain LY138 S protein (SEQ ID NO: 14, Genbank Accession No. AF058942), and comprising at least one of V at position 103; V at position 118; D at position 166; M at position 171; K at position 179; P at position 192; S at position 210; H at position 235; F at position 267; F at position 388; M at position 407; S at position 436; I at position 440; I at position 447; F at position 501; Y at position 525; N at position 528; L at position 540; K at position 582; G at position 608; G at position 692; S at position 695; W at position 757; G at position 758; Q at position 763; T at position 769; P at position 786; H at position 792; R at position 818; P at position 827; V at position 828; F at position 887; D at position 933; F at position 977; T at position 1011; S at position 1018; K at position 1063; L at position 1256 and M at position 1257.

For the avoidance of doubt, the invention includes a coronavirus S protein, or fragment thereof, having at least 75% amino acid sequence identity with BCV strain LY138 S protein (SEQ ID NO: 14), and comprising at least one of the amino acids specific for CRCV S protein at the position listed in Table 1.

The invention includes a coronavirus S protein, or fragment thereof, having at least 76% amino acid sequence identity with BCV strain LY138 S protein, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% amino acid sequence identity with BCV strain LY138 S protein, and having at least one of the amino acids specific for CRCV S protein at the position listed in Table 1.

The invention also includes a coronavirus S protein, or fragment thereof, having at least 75%, or at least 80%, or at least 85%, or at least 90%, or at least 95% amino acid sequence identity with BCV strain LY138 S protein (SEQ ID NO: 14), and comprising at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30, or at least 31, or at least 32, or at least 33, or at least 34, or at least 35, or at least 36, or at least 37, or at least 38 of the amino acids specific for CRCV S protein at the positions listed in Table 1.

Preferably, the coronavirus S protein, or fragment thereof comprises all 39 of the amino acid residues specific for CRCV S protein at the positions listed in Table 1.

A second aspect of the invention provides a coronavirus pol protein, or fragment thereof, having at least 90% amino acid sequence identity with the BCV pol protein (SEQ ID NO: 5) and comprising the amino acid E at the position corresponding to position 4975 in the BCV genome (Accession No. SWALL: Q91A29).

The invention includes a coronavirus pol protein, or fragment thereof, having at least 91% amino acid sequence identity with BCV strain LY138 pol protein, or at least 92%, or at least 93%, or at least 94%, or at least 95%, or at least 96%, or at least 97%, or at least 98%, or at least 99% amino acid sequence identity with BCV strain LY138 pol protein, and having the amino acid E at the position corresponding to position 4975 in the BCV genome (Accession No. SWALL: Q91A29).

Preferably, the coronavirus pol protein, or fragment thereof is a CRCV pol protein or fragment thereof that comprises or consists of the amino acid sequence listed in FIG. 2.

Thus the invention includes a BCV, HCV or HEV pol protein or fragment thereof, that has been modified at the amino acid corresponding to position 4975 in the BCV genome, to resemble the CRCV pol protein.

The invention also includes a CRCV pol protein fragment comprising a fragment of the sequence listed in FIG. 2 (SEQ ID NO: 2) and having the amino acid E at the position corresponding to position 4975 in the BCV genome.

A third aspect of the invention provides a coronavirus HE protein, or fragment thereof, having at least 90% amino acid sequence identity with the BCV LY138 HE protein (Genbank Accession No. AF058942), and having at least one of F at position 235; N at position 242; and L at position 253. The amino acid positions are numbered from the initial M (which is number 1) at the start of the BCV HE protein.

The invention includes a coronavirus HE protein, or fragment thereof, having at least 91% amino acid sequence identity with BCV strain LY138 HE protein, or at least 92%, or at least 93%, or at least 94%, or at least 95%, or at least 96%, or at least 97%, or at least 98%, or at least 99% amino acid sequence identity with BCV strain LY138 HE protein, and having at least one of F at position 235; N at position 242; and L at position 253. The amino acid positions are numbered from the initial M (which is number 1) at the start of the BCV HE protein.

The invention also includes a coronavirus HE protein, or fragment thereof, having at least 90%, or at least 91%, or at least 92%, or at least 93%, or at least 94%, or at least 95%, or at least 96%, or at least 97%, or at least 98%, or at least 99% amino acid sequence identity with BCV strain LY138 HE protein, and having two of F at position 235; N at position 242; and L at position 253. The amino acid positions are numbered from the initial M (which is number 1) at the start of the BCV HE protein.

The invention further includes a coronavirus HE protein, or fragment thereof, having at least 90%, or at least 91%, or at least 92%, or at least 93%, or at least 94%, or at least 95%, or at least 96%, or at least 97%, or at least 98%, or at least 99% amino acid sequence identity with BCV strain LY138 HE protein, and having all three of F at position 235; N at position 242; and L at position 253. The amino acid positions are numbered from the initial M (which is number 1) at the start of the BCV HE protein.

Preferably, the coronavirus HE protein, or fragment thereof is a CRCV HE protein or fragment thereof that comprises or consists of the amino acid sequence listed in FIG. 14 (SEQ ID NO: 22).

Thus the invention includes a BCV, HCV, HECV or HEV HE protein or fragment thereof, that has been modified at one or more of the amino acids corresponding to position 235, 242; and 253 to resemble the CRCV HE protein.

The invention also includes a CRCV HE protein fragment comprising a fragment of the sequence listed in FIG. 14 (SEQ ID NO: 22) and having one or more of the amino acid F at position 235, N at position 242, and L at position 253. The numbering of these amino acid positions corresponds to that of BCV LY138 HE protein (Genbank Accession No. AF058942) in which residue number 1 is the initial M at the start of the BCV LY138 HE protein.

The coronavirus S, pol and HE proteins as defined above in the first, second and third aspects of the invention may be termed herein "CRCV" or "CRCV-like" proteins.

A "CRCV S protein" is an S protein or fragment thereof that has the native CRCV S amino acid sequence as listed in FIG. 4 (SEQ ID NO: 4), or a fragment thereof which comprises at least one of the amino acids specific for a CRCV S protein at the positions listed in Table 1.

A "CRCV pol protein" is a pol protein or fragment thereof that has the native CRCV pol amino acid sequence as listed in FIG. 2 (SEQ ID NO: 2), or a fragment thereof which comprises the amino acid E at the position corresponding to position 4975 in the BCV genome.

A "CRCV HE protein" is an HE protein or fragment thereof that has the native CRCV HE amino acid sequence as listed in FIG. 14 (SEQ ID NO: 22), or a fragment thereof which comprises one or more of the amino acid F at position 235, N at position 242, and L at position 253. The numbering of these amino acid positions corresponds to that of BCV LY138 HE protein (Genbank Accession No. AF058942) in which residue number 1 is the initial M at the start of the BCV LY138 HE protein.

A "CRCV-like S protein" is an S protein or fragment thereof that does not have an amino acid sequence identical to the native CRCV S amino acid sequence (FIG. 4 and SEQ ID NO: 4), but has at least 75% sequence identity with the corresponding region of the CRCV or BCV strain LY138 S protein, and has at least one of the amino acids specific for a CRCV S protein at the positions listed in Table 1.

A "CRCV-like S protein" also includes an S protein that does not have an amino acid sequence identical to the native CRCV S amino acid sequence (FIG. 4 and SEQ ID NO: 4), but that comprises or consists of a variant of the sequence listed in FIG. 4 with at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

A "CRCV-like pol protein" is a pol protein or fragment thereof that does not have an amino acid sequence identical to the native CRCV pol amino acid sequence, but has at least 90% sequence identity with the corresponding BCV strain LY138 pol protein, and which has an E at the position corresponding to position 4975 in the BCV genome.

A "CRCV-like HE protein" is an HE protein or fragment thereof that does not have an amino acid sequence identical to the native CRCV HE amino acid sequence, but has at least 90% sequence identity with the corresponding BCV strain LY138 HE protein, and which has one or more of the amino acid F at position 235, N at position 242, and L at position 253. The numbering of these three amino acid positions corresponds to that of BCV LY138 HE protein (Genbank Accession No. AF058942) in which residue number 1 is the initial M at the start of the BCV LY138 HE protein.

Preferably, the CRCV or CRCV-like protein, or fragment thereof, is at least 10 amino acids in length. More preferably, the CRCV or CRCV-like protein, or fragment thereof, is at least 20, or at least 30, or at least 40, or at least 50, or at least 100, or at least 200, or at least 300, or at least 400, or at least 500, or at least 600, or at least 700, or at least 800, or at least 900, or at least 1,000, or at least 1,100, or at least 1,200 amino acids in length.

Preferably, the CRCV or CRCV-like protein, or fragment thereof, is less than about 1,300 amino acids in length. More preferably, the CRCV or CRCV-like protein, or fragment thereof, is less than about 1,200, or less than about 1,100, or less than about 1,000, or less than about 900, or less than about 800, or less than about 700, or less than about 600, or less than about 500, or less than about 400, or less than about 300, or less than about 200, or less than about 100, or less than about 50 amino acids in length.

CRCV proteins may be isolated from CRCV, or may be made using protein chemistry techniques for example using partial proteolysis of isolated proteins (either exolytically or endolytically), or by de novo synthesis. Alternatively, the CRCV proteins, as well as CRCV-like proteins, may be made by recombinant DNA technology. Suitable techniques for cloning, manipulation, modification and expression of nucleic acids, and purification of expressed proteins, are well known in the art and are described for example in Sambrook et al (2001) "*Molecular Cloning, a Laboratory Manual*", 3$^{rd}$ edition, Sambrook et al (eds), Cold Spring Harbor Laboratory Press, Cold Spring Harbor, N.Y., USA, incorporated herein by reference.

Shorter fragments of CRCV and CRCV-like proteins, i.e. peptides, may be synthesised using standard techniques. Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzene-sulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A fourth aspect of the invention provides a polynucleotide that encodes a CRCV or CRCV-like S, pol or HE protein according to the first, second and third aspects of the invention, or the complement thereof.

Preferably, the polynucleotide encodes a CRCV S protein according to the first aspect of the invention, or the complement thereof.

More preferably, the polynucleotide encoding the CRCV S protein comprises or consists of the sequence listed in FIG. 3 (SEQ ID NO: 3).

It is appreciated that the sequence listed in FIG. 3 (SEQ ID NO: 3) contains a Y at position 3531, which refers to either C or T. In both cases the corresponding amino acid is Ile. Thus the invention includes a polynucleotide encoding a CRCV S protein which comprises or consists of the sequence listed in FIG. 3, and having C at position 3531. The invention also includes a polynucleotide encoding a CRCV S protein which comprises or consists of the sequence listed in FIG. 3, and having T at position 3531.

The invention also includes a CRCV S polynucleotide comprising a fragment of the sequence listed in FIG. 3 (SEQ ID NO: 3), that encodes a protein having at least one of the amino acids specific for CRCV S protein at the position listed in Table 1, or the complement thereof.

Preferably, the polynucleotide encoding the pol protein comprises or consists of the sequence listed in FIG. 1 (SEQ ID NO: 1), or the complement thereof.

The invention also includes a CRCV pol polynucleotide comprising a fragment of the sequence listed in FIG. 1 (SEQ ID NO: 1) that encodes a protein having E at the position corresponding to position 4975 in the BCV genome, or the complement thereof.

Preferably, the polynucleotide encoding the HE protein comprises or consists of the sequence listed in FIG. 13 (SEQ ID NO: 21), or the complement thereof.

The invention also includes a CRCV HE polynucleotide comprising a fragment of the sequence listed in FIG. 13 (SEQ ID NO: 21) that encodes a protein having one or more of the amino acid F at position 235, N at position 242, and L at position 253. The numbering of these three amino acid positions corresponds to that of BCV LY138 HE protein (Genbank Accession No. AF058942) in which residue number 1 is the initial M at the start of the BCV LY138 HE protein.

The polynucleotides as defined above are referred to herein as CRCV or CRCV-like polynucleotides of the invention.

A "CRCV-like polynucleotide" is a polynucleotide that does not have a base sequence identical to all or a fragment of the native CRCV cDNA sequence as listed in FIGS. 1, 3 and 13 (SEQ ID NOS: 1, 3 and 21), but that encodes a CRCV or CRCV-like S pol or HE protein as defined above, or the complement thereof.

The CRCV is a positive strand RNA virus. The polynucleotide of the invention may be DNA or RNA. The RNA may be positive or negative strand RNA. The DNA may be single or double stranded DNA.

Suitable techniques for cloning and sequencing a cDNA from a positive strand RNA virus such as CRCV are well known in the art and are described for example in Sambrook et al 2001, incorporated herein by reference.

The CRCV or CRCV-like polynucleotides of the invention may be any suitable size. However, for certain purposes, such as probing or amplifying, it is preferred if the nucleic acid has fewer than 3,000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA oligonucleotides, suitable for use as hybridisation probes or as primers in a polymerase chain reaction, are particularly preferred.

Oligonucleotides that can specifically amplify, or hybridise to CRCV S, pol or HE polynucleotides, as opposed to BCV, HCV, HEV or enteric CCV S, pol or HE polynucleotides, are particularly preferred. Suitable oligonucleotides can be determined by a person of skill in the art by reference to the nucleotide sequence comparisons in FIGS. 6, 8, 9 and 15.

It is appreciated that the CRCV or CRCV-like oligonucleotides may, even under highly stringent conditions, hybridise to nucleic acid, whether RNA or DNA, from HCV, BCV, and HEV as well as from CRCV. However, it is preferred if the CRCV or CRCV-like oligonucleotides hybridise to nucleic acid from CRCV under more stringent conditions than to nucleic acid from HCV, BCV or HEV. This can either be determined experimentally or by a comparison of the oligonucleotide sequence with the respective CRCV, HCV, BCV and HEV sequences, as is well known to one of skill in the art (Sambrook et al 2001).

It is also appreciated that the CRCV or CRCV-like oligonucleotides may hybridise to nucleic acid, whether RNA or DNA, from the enteric CCV as well as from CRCV. However, it is preferred if the CRCV or CRCV-like oligonucleotides hybridise to nucleic acid from CRCV under more stringent conditions than to nucleic acid from enteric CCV. This can either be determined experimentally or by a comparison of the oligonucleotide sequence with the respective sequences, as is well known to one of skill in the art (Sambrook et al 2001). Preferably, the oligonucleotides do not hybridise to nucleic acid from enteric CCV at all under stringent conditions (see below).

Conveniently, the CRCV or CRCV-like polynucleotides or oligonucleotides further comprise a detectable label.

By "detectable label" is included any convenient radioactive label such as $^{32}$P, $^{33}$P or $^{35}$S which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed array and whether a nucleic acid hybridises to it can be determined by reference to the position of hybridisation in the fixed array.

Labelling with [$^{32}$P]dCTP may be carried out using a Rediprime® random primer labelling kit supplied by Amersham.

Primers which are suitable for use in a polymerase chain reaction (PCR; Saiki et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artefactual product called "primer dimer". When the 3' ends of the two primers hybridise, they form a "primed template" complex, and primer extension results in a short duplex product called "primer dimer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilised. The concentrations of the primers are equal in conventional (symmetric) PCR and, typically, within 0.1- to 1 μM range.

It will further be appreciated that if a control amplification reaction is to be carried out, for example using primers complementary to an ubiquitously expressed gene, that it may be beneficial for the products of the control and CRCV or CRCV-like products to be of different sizes, such that the two products may be distinguished by the detection means employed, for example by mobility on agarose gel electrophoresis. However, it may be desirable for the two products to be of similar size, for example both between 100 and 1000, or between 100 and 600 nucleotides long. This may aid simultaneous analysis of the products, for example by gel electrophoresis, and may also mean that the control and CRCV or CRCV-like amplification reactions may have similar performance characteristics, in terms, for example, of relative rates of accumulation of product at different stages during the reaction.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton, (1991) *Nature* 350, 91-92 and *AIDS* (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

When a pair of suitable nucleic acids of the invention are used in a PCR it is convenient to detect the product by gel electrophoresis and ethidium bromide staining. As an alternative, it is convenient to use a labelled oligonucleotide capable of hybridising to the amplified DNA as a probe. When the amplification is by PCR the oligonucleotide probe hybridises to the interprimer sequence as defined by the two primers. The oligonucleotide probe is preferably between 10 and 50 nucleotides long, more preferably between 15 and 30 nucleotides long. It may be longer than the amplified DNA or include one or both of the primers, but in this case, the hybridisation conditions should be such that the probe should not hybridise to the primers alone, but only to an amplified product that also contains interprimer sequence that is capable of hybridising to the probe.

The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991). "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

The invention also includes a vector comprising the CRCV or CRCV-like polynucleotide of the fourth aspect of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Generally, the CRCV or CRCV-like polynucleotide of the invention is inserted into an expression vector, such as a plasmid, in proper orientation and correct reading frame for expression. It may be linked to the appropriate transcriptional and translational regulatory control nucleotide sequences recognised by the desired host prior to insertion into the vector, although such controls are generally available in the expression vector. Thus, the polynucleotide of the invention insert may be operatively linked to an appropriate promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs desirably also contain sites for transcription initiation and termination, and in the transcribed region, a ribosome binding site for translation (Hastings et al, International Patent No. WO 98/16643).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the polynucleotide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The specific primers may contain restriction endonuclease recognition sites which can be used for cloning into expression vectors using methods known in the art.

The invention also includes a host cell transformed with the vector comprising the CRCV or CRCV-like polynucleotide. The host cell can be either prokaryotic or eukaryotic. If the CRCV or CRCV-like polynucleotide, in the vector, is to be expressed as a glycoprotein, the host cell is a eukaryotic host cell, and preferably a mammalian host cell.

Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a vector is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual,* 3$^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 μFD.

Methods for transformation of yeast by electroporation are disclosed in Becker & Guarente (1990) *Methods Enzymol.* 194, 182.

Physical methods may be used for introducing DNA into animal and plant cells. For example, microinjection uses a very fine pipette to inject DNA molecules directly into the nucleus of the cells to be transformed. Another example involves bombardment of the cells with high-velocity microprojectiles, usually particles of gold or tungsten that have been coated with DNA.

Successfully transformed cells, i.e. cells that contain a CRCV or CRCV-like DNA construct, can be identified by well known techniques. For example, one selection technique involves incorporating into the expression vector a DNA sequence (marker) that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for the selectable trait can be on another vector, which is used to co-transform the desired host cell.

The marker gene can be used to identify transformants but it is desirable to determine which of the cells contain recombinant DNA molecules and which contain self-ligated vector molecules. This can be achieved by using a cloning vector where insertion of a DNA fragment destroys the integrity of one of the genes present on the molecule. Recombinants can therefore be identified because of loss of function of that gene.

Another method of identifying successfully transformed cells involves growing the cells resulting from the introduction of an expression construct of the present invention to produce the CRCV or CRCV-like S, pol or HE protein. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

Host cells that have been transformed by the recombinant CRCV or CRCV-like polynucleotide, typically in a vector as described above, are then cultured for a sufficient time and under appropriate conditions known to those skilled in the art in view of the teachings disclosed herein to permit the expression of the CRCV or CRCV-like protein encoded by the CRCV or CRCV-like polynucleotide, which can then be recovered.

The CRCV or CRCV-like protein can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

For example, for expression in a baculovirus system, recombinant DNA encoding the CRCV spike gene may be cloned into a suitable transfer vector such as pMelBac (Invitrogen). Co-transfection with baculovirus DNA (e.g. Bac-N-Blue/Invitrogen) results in a recombinant baculovirus encoding the spike gene. Infection of a suitable insect cell line (e.g. Sf9, Sf21, High Five/Invitrogen) at an appropriate multiplicity of infection leads to expression of the recombinant spike protein. Protein expression is confirmed by western blotting or ELISA using appropriate reagents (e.g. convalescent canine serum or other virus specific antiserum).

The invention thus includes a method of obtaining a CRCV or CRCV-like protein encoded by the CRCV or CRCV-like polynucleotide of the present invention. The method comprises culturing the host cell comprising the CRCV or CRCV-like polynucleotide, typically in a vector; expressing the protein in the host cell, and purifying the protein. The invention further includes the protein obtainable by this method.

The invention thus also includes a method of obtaining a glycosylated CRCV or CRCV-like protein, typically an S protein, encoded by the CRCV or CRCV-like polynucleotide of the present invention. The method comprises culturing a eukaryotic, or more preferably mammalian, host cell comprising the CRCV or CRCV-like polynucleotide, typically in a vector; expressing the protein in the host cell; and purifying the glycosylated protein. The invention further includes the glycosylated protein obtainable by this method.

In a fifth aspect, the invention provides a method of making an anti-CRCV antibody comprising raising an immune response to a CRCV or CRCV-like S protein of the invention as described above in the first aspect of the invention in an animal, and preparing an antibody from the animal or from an immortal cell derived therefrom. Alternatively, the method may comprise selecting an antibody from an antibody-display library using a CRCV or CRCV-like S protein of the invention as described above in the first aspect of the invention.

Methods and techniques for producing a monoclonal antibody are well known to a person of skill in the art, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982), incorporated herein by reference.

Optionally, the method further comprises determining whether the antibody thus obtained has greater affinity for the CRCV S protein than for the BCV S protein, and preferably also whether the antibody has a greater affinity for the CRCV S protein than for the HCV and HEV S proteins. Methods for determining the relative affinity of antibodies for antigens are known in the art.

The invention also includes an anti-CRCV antibody obtainable by the method of the fifth aspect of the invention, that has greater affinity for the CRCV S protein than for the BCV S protein. Preferably, the antibody also has a greater affinity for the CRCV S protein than for the HCV and HEV S proteins.

The invention also includes a method of making an anti-CRCV antibody comprising raising an immune response to a CRCV or CRCV-like HE protein of the invention as described above in the third aspect of the invention in an animal, and preparing an antibody from the animal or from an immortal cell derived therefrom. Alternatively, the method may comprise selecting an antibody from an antibody-display library using a CRCV or CRCV-like HE protein of the invention as described above in the third aspect of the invention.

Optionally, the method further comprises determining whether the antibody thus obtained has greater affinity for the CRCV HE protein than for the BCV HE protein, and preferably also whether the antibody has a greater affinity for the CRCV HE protein than for the HCV and HEV HE proteins. Methods for determining the relative affinity of antibodies for antigens are known in the art.

The invention also includes an anti-CRCV antibody obtainable by the method of the fifth aspect of the invention, that has greater affinity for the CRCV HE protein than for the BCV HE protein. Preferably, the antibody also has a greater affinity for the CRCV HE protein than for the HCV and HEV HE proteins.

Preferably, the antibody is a monoclonal antibody. However, the invention includes a monospecific anti-CRCV antibody. The antibody may be an antibody fragment, as described below.

The monoclonal or monospecific antibody may be a chimaeric antibody, as discussed by Neuberger et al (1988, 8th International Biotechnology Symposium Part 2, 792-799). The monoclonal or monospecific antibody may also be a "caninised" antibody, for example by inserting the CDR regions of mouse antibodies into the framework of canine antibodies.

The invention also includes anti-CRCV antibody fragments. The variable heavy ($V_H$) and variable light ($V_L$) domains of antibodies are involved in antigen recognition, a fact first recognised by early protease digestion experiments. Further confirmation was found by "humanisation" of rodent antibodies, in which variable domains of rodent origin may be fused to constant domains of human origin such that the resultant antibody retains the antigenic specificity of the rodent parented antibody (Morrison et al (1984) Proc. Natl. Acad. Sci. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are linked via a flexible oligopeptide.

The advantages of antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the fragments.

Whole antibodies, and F(ab')₂ fragments are "bivalent". By "bivalent" we mean that the antibodies and F(ab')₂ fragments have two antigen combining sites. In contrast, Fab, Fv, ScFv and dAb fragments are monovalent, having only one antigen combining sites.

In a sixth aspect, the invention provides a method of determining whether a dog has been exposed to CRCV. The method comprises obtaining a suitable sample from the dog, and identifying CRCV or an anti-CRCV antibody in the sample. The method may be used as an aid in the diagnosis of whether a dog has CIRD.

The invention includes a method of detecting, in a sample obtained from a dog, past exposure of the dog to CRCV, the method comprising obtaining a suitable sample from the dog, and identifying anti-CRCV antibodies in the sample.

In one preferred embodiment, the suitable sample can be any antibody containing sample such as serum, saliva, tracheal wash or bronchiolar lavage.

Preferably, the anti-CRCV antibody can be detected using a BCV, HCV, HEV or CRCV antigen, more preferably, using a BCV or CRCV antigen.

More preferably, identifying an anti-CRCV antibody in the sample comprises identifying an antibody that selectively binds to an S protein whose amino acid sequence is at least 75% identical with the amino acid sequence of the CRCV S protein (FIG. 4 and SEQ ID NO: 4); an S protein whose amino acid sequence is at least 75% identical with the amino acid sequence of the BCV S protein (Genbank Accession No. AF058942); HCV S protein (Genbank Accession No. L14643); to a coronavirus having an S protein at least 75% identical with BCV S protein (Genbank Accession No. AF058942), or a fragment thereof; or to a coronavirus having an S protein at least 75% identical with the CRCV S protein, or a fragment thereof.

More preferably, identifying an antibody that selectively binds to an S protein whose amino acid sequence is at least 75% identical with the amino acid sequence of the BCV S protein, comprises identifying an antibody that selectively binds to an S protein whose amino acid sequence is at least 80% identical, or at least 85% identical, or at least 90% identical, or at least 95% identical with the amino acid sequence of the BCV S protein (Genbank Accession No. AF058942) or a fragment thereof.

More preferably, identifying an anti-CRCV antibody in the sample comprises identifying an antibody that selectively binds to the BCV S protein (Genbank Accession No. AF058942).

Even more preferably, identifying an antibody that selectively binds to an S protein whose amino acid sequence is at least 75% identical with the amino acid sequence of the CRCV S protein, comprises identifying an antibody that selectively binds to an S protein whose amino acid sequence is at least 80% identical, or at least 85% identical, or at least 90% identical, or at least 95% identical with the amino acid sequence of the CRCV S protein (FIG. 4 and SEQ ID NO: 4) or a fragment thereof.

Yet more preferably, identifying an anti-CRCV antibody in the sample comprises identifying an antibody that selectively binds to a CRCV or CRCV-like S protein as defined in the first aspect of the invention.

Most preferably, identifying an anti-CRCV antibody in the sample comprises identifying an antibody that selectively binds to the CRCV S protein as listed in FIG. 4 (SEQ ID NO: 4), or a fragment thereof.

Similarly, identifying an anti-CRCV antibody in the sample may comprise identifying an antibody that selectively binds to an HE protein whose amino acid sequence is at least 90% identical with the partial amino acid sequence of the CRCV HE protein (FIG. 14 and SEQ ID NO: 22); to an HE protein whose amino acid sequence is at least 90% identical with the amino acid sequence of the BCV HE protein (Genbank Accession No. AF058942) or the HECV HE protein (Genbank Accession No. L07747); to a coronavirus having an S protein at least 90% identical with BCV HE protein (Genbank Accession No. AF058942), or a fragment thereof; or to a coronavirus having an HE protein at least 90% identical with the CRCV HE protein, or a fragment thereof.

More preferably, identifying an antibody that selectively binds to an HE protein whose amino acid sequence is at least 90% identical with the amino acid sequence of the BCV HE protein, comprises identifying an antibody that selectively binds to an HE protein whose amino acid sequence is at least 91% identical, or at least 92% identical, or at least 93% identical, or at least 94% identical, or at least 95% identical, or at least 96% identical, or at least 97% identical, or at least 98% identical, or at least 99% identical with the amino acid sequence of the BCV HE protein (Genbank Accession No. AF058942) or a fragment thereof.

More preferably, identifying an anti-CRCV antibody in the sample comprises identifying an antibody that selectively binds to the BCV HE protein (Genbank Accession No. AF058942).

Even more preferably, identifying an antibody that selectively binds to an HE protein whose amino acid sequence is at least 90% identical with the partial amino acid sequence of the CRCV HE protein, comprises identifying an antibody that selectively binds to an HE protein whose partial amino acid sequence is at least 91% identical, or at least 92% identical, or at least 93% identical, or at least 94% identical, or at least 95% identical, or at least 96% identical, or at least 97% identical, or at least 98% identical, or at least 99% identical with the partial amino acid sequence of the CRCV HE protein (FIG. 13) or a fragment thereof.

Yet more preferably, identifying an anti-CRCV antibody in the sample comprises identifying an antibody that selectively binds to a CRCV or CRCV-like HE protein as defined in the third aspect of the invention.

Most preferably, identifying an anti-CRCV antibody in the sample comprises identifying an antibody that selectively binds to the CRCV HE protein whose partial amino acid sequence is listed in FIG. 14 (SEQ ID NO: 22), or a fragment thereof.

The invention includes a method of detecting CRCV in a sample obtained from a dog, the method comprising obtaining a suitable sample from the dog, and identifying CRCV in the sample.

It is appreciated that there may be some naturally occurring sequence variation between different isolates of CRCV. The invention thus includes identifying CRCV isolates whose S, pol and HE genes and proteins have some sequence variation from the sequences provided in FIGS. 1 to 4 and 13 and 14. It is appreciated, however, that the same methods will be used to detect the variant isolates of CRCV, as well as the isolate characterised by the sequences listed in FIGS. 1 to 4 and 13 and 14.

In a preferred embodiment, the suitable sample can be a lung wash, tracheal wash, tonsillar swab or a biopsy or postmortem sample from the respiratory tract of the dog.

Preferably, in this embodiment, identifying CRCV comprises identifying a nucleic acid component of CRCV.

Typically, this will be performed by extracting RNA from the sample, and obtaining cDNA therefrom, for example as is described in Example 1. Thereafter, a CRCV nucleic acid component is identified in the cDNA, for example using techniques involving high stringency hybridisation, specific amplification, and nucleotide sequencing, as are well known to a person of skill in the art (Sambrook et al (2001) supra).

Preferably, identifying CRCV comprises identifying a polynucleotide that hybridises at high stringency to the BCV genome, such as the LY138 strain genome (Genbank Accession No. AF058942) or a portion thereof.

Further preferably, identifying CRCV comprises identifying a polynucleotide that hybridises at high stringency to the CRCV S, pol or HE polynucleotides (FIGS. 1, 3 and 13) or a portion thereof.

By "hybridising at high stringency" is meant that the polynucleotide and the nucleic acid to which it hybridises have sufficient nucleotide sequence similarity that they can hybridise under highly stringent conditions. As is well known in the art, the stringency of nucleic acid hybridisation depends on factors such as length of nucleic acid over which hybridisation occurs, degree of identity of the hybridising sequences and on factors such as temperature, ionic strength and CG or AT content of the sequence.

Nucleic acids which can hybridise at high stringency to the CRCV cDNA molecule include nucleic acids which have >90% sequence identity, preferably those with >95% or >96% or >97% or >98, more preferably those with >99% sequence identity, over at least a portion of the CRCV cDNA.

Typical highly stringent hybridisation conditions which lead to selective hybridisation are known in the art, for example those described in Sambrook et al 2001 (supra), incorporated herein by reference.

An example of a typical hybridisation solution when a nucleic acid is immobilised on a nylon membrane and the probe nucleic acid is ≧500 bases is:

6×SSC (saline sodium citrate)
0.5% sodium dodecyl sulphate (SDS)
100 μg/ml denatured, fragmented salmon sperm DNA The hybridisation is performed at 68° C. The nylon membrane, with the nucleic acid immobilised, may be washed at 68° C. in 0.1×SSC.

20×SSC may be prepared in the following way. Dissolve 175.3 g of NaCl and 88.2 g of sodium citrate in 800 ml of $H_2O$. Adjust the pH to 7.0 with a few drops of a 10 N solution of NaOH. Adjust the volume to 1 litre with $H_2O$. Dispense into aliquots. Sterilise by autoclaving.

An example of a typical hybridisation solution when a nucleic acid is immobilised on a nylon membrane and the probe is an oligonucleotide of between 15 and 50 bases is:

3.0 M trimethylammonium chloride (TMACl)
0.01 M sodium phosphate (pH 6.8)
1 mm EDTA (pH 7.6)
0.5% SDS
100 μg/ml denatured, fragmented salmon sperm DNA
0.1% non-fat dried milk The optimal temperature for hybridisation is usually chosen to be 5° C. below the $T_i$ for the given chain length. $T_i$ is the irreversible melting temperature of the hybrid formed between the probe and its target sequence. Jacobs et al (1988) Nucl. Acids Res. 16, 4637 discusses the determination of $T_i$s.

The recommended hybridization temperature for 17-mers in 3M TMACl is 48-50° C.; for 19-mers, it is 55-57° C.; and for 20-mers, it is 58-66° C.

Preferably, identifying CRCV comprises using a polynucleotide having at least 80%, or at least 85%, or at least 90%, or at least 95% identity with a portion of the BCV genome (Genbank Accession No. AF058942).

More preferably, identifying CRCV comprises using a polynucleotide having at least 80%, or at least 85%, or at least 90%, or at least 95% identity with a portion of the CRCV S polynucleotide (FIG. 3), or having at least 90%, or at least 95% identity with a portion of the CRCV pol polynucleotide (FIG. 1), or having at least 90%, or at least 95% identity with a portion of the CRCV HE polynucleotide (FIG. 13).

More preferably, identifying CRCV comprises identifying a CRCV polynucleotide as defined above with respect to the fourth aspect of the invention.

Most preferably, identifying CRCV comprises identifying a CRCV polynucleotide comprising or consisting of a sequence listed in FIG. 1 or FIG. 3 or FIG. 13, or a fragment thereof.

In another preferred embodiment, identifying CRCV comprises identifying a protein component of CRCV.

Preferably, identifying a protein component of CRCV comprises identifying a CRCV protein as defined above in the first or second or third aspects of the invention.

Most preferably, identifying a protein component of CRCV comprises identifying a CRCV protein comprising or consisting of the amino acid sequence listed in FIG. 2 or FIG. 4 or FIG. 14, or a fragment thereof.

Assaying a protein component of CRCV in a biological sample can occur using any art-known method. Preferred for assaying CRCV protein levels in a biological sample are antibody-based techniques.

Preferably, identifying a protein component of CRCV comprises using an antibody reactive with CRCV.

More preferably, the antibody reactive with CRCV is an anti-BCV antibody, an anti-HCV antibody, an anti-HEV antibody, or an anti-CRCV antibody obtainable or obtained by the methods of the fifth aspect of the invention.

For example, CRCV protein expression can be studied with classical immunohistological methods. In these, the specific recognition is provided by the primary antibody (polyclonal or monoclonal) but the secondary detection system can utilise fluorescent, enzyme, or other conjugated secondary antibodies. As a result, an immunohistological staining of tissue section for pathological examination is obtained. Tissues can also be extracted, e.g., with urea and neutral detergent, for the liberation of CRCV protein for Western-blot or dot/slot assay (Jalkanen, M., et al, *J. Cell. Biol.* 101:976-985 (1985); Jalkanen, M., et al, *J. Cell. Biol.* 105:3087-3096 (1987)). In this technique, which is based on the use of cationic solid phases, quantitation of CRCV protein can be accomplished using isolated CRCV protein as a standard. This technique can also be applied to body fluid samples.

Other antibody-based methods useful for detecting CRCV protein expression include immunoassays, such as the enzyme linked immunosorbent assay (ELISA) and the radio-immunoassay (RIA). For example, a CRCV reactive monoclonal antibody can be used both as an immunoabsorbent and as an enzyme-labeled probe to detect and quantify the CRCV protein. The amount of CRCV protein present in the sample can be calculated by reference to the amount present in a standard preparation using a linear regression computer algorithm. Such an ELISA for detecting a tumour antigen is described in Iacobelli et al, *Breast Cancer Research and Treatment* 11: 19-30 (1988). In another ELISA assay, two distinct specific monoclonal antibodies can be used to detect CRCV protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting CRCV protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur $^{35}$S), tritium ($^{3}$H), indium ($^{112}$In), and technetium ($^{99m}$Tc), and fluorescent labels, such as fluorescein and rhodamine, and biotin.

In a seventh aspect, the invention provides an immunosorbent assay for detecting anti-CRCV S or HE antibodies. The assay comprises a solid phase coated with a CRCV or CRCV-like S or HE protein, or coated with both CRCV or CRCV-like S and HE proteins as defined in the first and third aspects of the invention, or obtainable using the methods of the fourth aspect of the invention, or an antigenic fragment thereof, wherein anti-CRCV S or HE antibodies in a sample exposed to the solid phase will bind to the protein; and a detectable label conjugate which will bind to the anti-CRCV antibodies bound to the solid phase.

It is appreciated that an antigenic fragment of the CRCV or CRCV-like S protein that coats the solid phase is of sufficient size to be bound by an anti-CRCV S antibody, and which comprises at least one of the amino acids specific for CRCV S protein as listed in Table 1.

It is also appreciated that an antigenic fragment of the CRCV or CRCV-like HE protein that coats the solid phase is of sufficient size to be bound by an anti-CRCV HE antibody, and which comprises at least one of the three amino acids specific for CRCV HE protein as defined above.

Preferably, the CRCV or CRCV-like S or HE protein, or antigenic fragment thereof, that coats the solid phase is at least 10 amino acids in length. More preferably, the CRCV or CRCV-like S protein, or antigenic fragment thereof, is at least 20, or at least 30, or at least 40, or at least 50, or at least 100, or at least 200, or at least 300, or at least 400 amino acids in length. The CRCV or CRCV-like S protein may be at least 500, or at least 600, or at least 700, or at least 800, or at least 900, or at least 1,000 amino acids in length.

Preferably, the CRCV or CRCV-like S protein, or antigenic fragment thereof, that coats the solid phase is less than about 1200 amino acids in length. More preferably, the CRCV or CRCV-like S protein, or antigenic fragment thereof, is less than about 1,100, or less than about 1,000, or less than about 900, or less than about 800, or less than about 700, or less than about 600, or less than about 500 amino acids in length. The CRCV or CRCV-like S or HE protein may be less than about 400, or less than about 300, or less than about 200, or less than about 100, or less than about 50 amino acids in length.

Preferably, the solid phase is a microtitre well.

Further preferably, the conjugate comprises anti-dog antibody.

Preferably, the conjugate comprises an enzyme, for example horseradish peroxidase. Further preferably, the immunosorbent assay also comprises a substrate for the enzyme.

Further details of suitable immunosorbent assays and ELISAs are provided above.

The invention includes a kit of parts which include the components of the immunosorbent assay. The kit of parts may thus include a solid phase such as a microtitre plate, CRCV or CRCV-like S or HE protein or both for coating the solid phase, a detectable label conjugate, such as an anti-dog antibody, which will bind to anti-CRCV antibodies bound to the solid phase. If the detectable label conjugate is an enzyme, the kit of parts may also include a substrate for the enzyme. The kit may also include a positive control sample that contains an anti-CRCV S or HE protein antibody, such as those described with reference to the fifth aspect of the invention, and a negative control sample.

The invention thus includes a solid substrate with a CRCV or CRCV-like S or HE protein as defined in the first and third aspects of the invention, or obtainable using the methods of the fourth aspect of the invention, or an antigenic fragment thereof, attached thereto, for capturing anti-CRCV S or HE antibodies or both from a liquid sample, wherein anti-CRCV S or HE antibodies in a sample exposed to the solid substrate will bind to the S or HE protein.

Typically, protein is coated on microtitre plates overnight at 4° C. to 37° C., depending on the stability of the antigen. Unbound protein is washed off with a wash buffer such as phosphate buffered saline or Tris buffered saline. Serum or other samples are incubated on the plate, typically at 37° C. for between 1 and several hours. Unbound material is washed off, the plates are incubated with enzyme-labelled (e.g. horseradish peroxidase) antibody, such as anti-canine IgG or IgM for serum samples, or anti-canine IgA for lung washes, for 1 to several hours at 37° C. Unbound antibody is washed off and plates are incubated with a substrate such as OPD for about 10 min, and the optical density measured in a photometer.

Preferably, the solid substrate is a microtitre well.

In an eighth aspect, the invention provides a vaccine composition for vaccinating dogs comprising (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronavirus protein having at least 75% amino acid identity with a BCV protein or an immunogenic fragment thereof, or (vii) a nucleic acid encoding said coronaviral protein or immunogenic fraction thereof.

Preferably, the vaccine is packaged and presented for use in dogs.

When the vaccine comprises a coronavirus protein, or an immunogenic fragment thereof, the protein preferably has at least 80%, or at least 85%, or at least 90%, or at least 95% amino acid identity with the corresponding portion of a BCV or CRCV protein.

Preferably, the coronavirus protein is a BCV, HCV, HEV or CRCV protein, or a modification thereof.

Typical protein modifications include amino acid substitutions to improve the antigenicity of the vaccine. BCV, HCV and HEV proteins may be modified to be more like a CRCV protein. For example, the spike protein of BCV, HCV or HEV may be modified to include a CRCV amino acid at any of differences shown in the comparison in FIG. 10, or listed in Table 1. Additionally or alternatively, the HE protein of BCV, HCV or HEV may be modified to include a CRCV amino acid at any of the three CRCV-specific residues as defined above.

Proteins in which one or more of the amino acid residues are chemically modified, may be used providing that the function of the protein, namely the production of specific antibodies in vivo, remains substantially unchanged. It is appreciated that synthesised proteins may be suitably modified before or after their synthesised. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism.

The protein may be present as single copies or as multiples, for example tandem repeats. Such tandem or multiple repeats may be sufficiently antigenic themselves to obviate the use of a carrier. It may be advantageous for the protein to be formed as a loop, with the N-terminal and C-terminal ends joined together, or to add one or more Cys residues to an end to increase antigenicity and/or to allow disulphide bonds to be formed. If the protein is covalently linked to a carrier, preferably a polypeptide, then the arrangement is preferably such that the protein of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys (SEQ ID NO: 52), beta-galactosidase and the 163-171 peptide of interleukin-1. The latter compound may variously be regarded as a carrier or as an adjuvant or as both. Alternatively, several copies of the same or different proteins of the invention may be cross-linked to one another, in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the protein is prepared by expression of a suitable nucleotide sequence in a suitable host, then it may be advantageous to express it as a fusion product with a peptide sequence which acts as a carrier. Kabigen's "Ecosec" system is an example of such an arrangement.

It is appreciated that the coronavirus component of the vaccine may be linked to other antigens to provide a dual effect.

Preferably, the coronavirus protein in the vaccine composition is an S protein. More preferably, the S protein is a CRCV or CRCV-like S protein as defined above in the first aspect of the invention or obtainable by the methods of the fourth aspect of the invention, a BCV S protein, an HCV S protein, an HEV S protein, or an immunogenic fragment thereof.

Most preferably, the vaccine composition contains a CRCV S protein that comprises or consists of the amino acid sequence listed in FIG. 4, or an immunogenic fragment thereof having at least 97% identity with the sequence listed in FIG. 4. Preferably, the variant has at least at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Additionally or alternatively, the vaccine composition may comprise coronavirus proteins such as a hemagglutinin-esterase protein (HE) or an integral membrane protein (M), or the small membrane protein (E) (Lai MMC & Cavanagh D, (1997) "The molecular biology of coronaviruses" Adv. Vir. Res, 48: 1-100).

In one embodiment, the HE, E or M proteins are BCV, HCV or HEV proteins. In another embodiment, the HE, E or M proteins are CRCV proteins.

Preferably, the HE protein is a CRCV or CRCV-like HE protein as defined above in the third aspect of the invention or obtainable by the methods of the fourth aspect of the invention, or an immunogenic fragment thereof.

More preferably, the vaccine composition contains a CRCV HE protein that comprises or consists of the partial amino acid sequence listed in FIG. 14, or an immunogenic fragment thereof having at least 97% identity with the sequence listed in FIG. 14. Preferably, the variant has at least at least 98%, or at least 99% amino acid sequence identity with the sequence listed in FIG. 14. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 14.

When the vaccine comprises a coronavirus, preferably the coronavirus comprises an S protein with at least 80%, or at least 85%, or at least 90%, or at least 95% amino acid identity with the BCV S protein. More preferably, the coronavirus comprises an S protein with at least 80%, or at least 85%, or at least 90%, or at least 95% amino acid identity with the CRCV S protein.

Additionally or alternatively, when the vaccine comprises a coronavirus, preferably the coronavirus comprises an HE protein with at least 90% or at least 95% amino acid identity with the BCV HE protein. More preferably, the coronavirus comprises an HE protein with at least 96%, or at least 97%, or at least 98%, or at least 99% amino acid identity with the CRCV HE protein.

In another preferred embodiment, the vaccine composition comprises a virus selected from BCV, HCV, HEV and CRCV, or a modification thereof.

It is appreciated that dog vaccines effective against a canine virus may be derived from a non-canine virus. For example U.S. Pat. No. 5,750,112 to Gill, and assigned to Solvay Animal Health Inc, discloses a vaccine against enteric canine coronavirus containing inactivated feline enteric coronavirus. The disclosure of U.S. Pat. No. 5,750,112 is incorporated herein by reference.

In one preferred embodiment, the virus is an inactivated virus. Methods for inactivating viruses for use in vaccines are well known in the art. Suitable methods include chemical methods, such as the use of beta proprio-lactone (BPL). Suitable inactivated bovine coronavirus vaccines may include inactivated BCV which is a component of bovine vaccines such as "Rotovec Corona" from Schering-Plough (http://www.ukvet.co.uk/rotovec/scour.htm); "Lactovac" by Hoechst Roussel Vet Ltd, (Veterinary Formulary 5th Edition of the Veterinary Data Sheet Compendium); "First Defense" by Immuncell Corp, USA; "Scour Bos 4" by Grand Laboratories and "Scour Guard 3K" by Pfizer.

In an alternative embodiment, the virus is an attenuated virus. Methods for attenuating viruses for use in vaccines are well known in the art.

Preferably, the vaccine composition also comprises a pharmaceutically acceptable adjuvant.

Preferably, when the vaccine comprises a nucleic acid, the nucleic acid encoding the coronaviral protein or immunogenic fraction thereof, for use as a vaccine is a CRCV or CRCV-like S polynucleotide, or a CRCV or CRCV-like HE polynucleotide or both a CRCV or CRCV-like S and HE polynucleotide. More preferably, the nucleic acid comprises or consists of the nucleotide sequence listed in FIG. 3 or FIG. 13, or fractions thereof.

For vaccine use, the CRCV or CRCV-like S or HE nucleic acid can be delivered in various replicating (e.g. recombinant adenovirus vaccine) or non-replicating (DNA vaccine) vectors.

In a preferred embodiment, the vaccine may contain recombinant CRCV or CRCV-like S protein, as well as other immunogenic coronavirus proteins such as the HE protein.

As discussed above, several viral and bacterial agents are known to be associated with respiratory disease in dogs, including canine parainfluenza virus (CPIV), canine adenovirus type 2 (CAV-2), canine herpesvirus (CHV), and *Bordetella bronchiseptica* (*B. bronchiseptica*).

In another preferred embodiment, the vaccine may contain recombinant CRCV or CRCV-like S or HE protein, as well as other pathogenic organisms involved in respiratory disease of dogs such as canine parainfluenzavirus, canine adenovirus type 2, the bacterium *Bordetella bronchiseptica*, canine herpesvirus, human reovirus and mycoplasma species, or immunogenic proteins therefrom. Thus the vaccine may contain an agent capable of raising an immune response, such as the production of antibodies against CRCV, as well as against other pathogenic organisms involved in respiratory disease of dogs such as CPIV, CAV-2, *B. bronchiseptica* and CHV.

In an embodiment, as well as containing an agent capable of stimulating the production of antibodies against CRCV, such as a CRCV or CRCV-like S or HE protein, the vaccine composition further comprises any one or more of:

(a) an agent capable of raising an immune response in a dog against CPIV;

(b) an agent capable of raising an immune response in a dog against CAV-2;

(c) an agent capable of raising an immune response in a dog against CHV; and (d) an agent capable of raising an immune response in a dog against *B. bronchiseptica*.

Thus the vaccine composition can optionally also comprise any two, or any three or all four of these additional agents (a), (b), (c) and (d).

Typically, an agent capable of raising an immune response in a dog against CPIV comprises inactivated or attenuated CPIV, or an immunogenic fragment thereof, or a nucleic acid encoding said immunogenic fraction.

Typically, an agent capable of raising an immune response in a dog against CAV-2 comprises inactivated or attenuated CAV-2, or an immunogenic fragment thereof, or a nucleic acid encoding said immunogenic fraction.

Canine adenovirus type 1 causes infectious hepatitis; canine adenovirus type 2 causes respiratory disease. It has been shown that CAV-1 provides cross-protection against CAV-2 and vice versa. The agent that raises an immune response in a dog against CAV-2 may therefore contain either CAV-1 or CAV-2, or an immunogenic fragment thereof. The vaccines listed below contain CAV-2 except for EURICAN DHPPi, which does not specify the virus type used.

Suitable agents that raise an immune response in a dog against CPIV and CAV-2 are known to a person of skill in the art. For example, the following dog vaccines are licensed in the UK.

KAVAK $DA_2PiP69$ by Fort Dodge Animal Health is a live freeze dried vaccine containing attenuated strains of canine distemper virus, canine adenovirus type 2, canine parainfluenza type 2 and canine parvovirus grown in tissue culture.

KAVAK Parainfluenza by Fort Dodge Animal Health contains live freeze-dried vaccine derived from an attenuated strain of canine parainfluenza virus type 2 cultivated on an established homologous cell-line.

NOBIVAC DHPPi by Intervet UK Limited is a live attenuated freeze-dried, virus vaccine containing canine distemper virus, canine adenovirus type 2, canine parvovirus and canine parainfluenza virus grown in cell line tissue culture.

NOBIVAC KC by Intervet UK Limited is a modified live freeze-dried vaccine containing *Bordetella bronchiseptica* strain B-C2 and canine parainfluenza virus strain Cornell (this is an intranasal vaccine). Management authorisation number Vm 06376/4026.

EURICAN DHPPi by Merial Animal Health Ltd. is a combined live freeze-dried vaccine against canine distemper, infectious canine hepatitis, canine parvovirus and canine parainfluenza virus type 2.

VANGUARD 7 by Pfizer Ltd. contains live attenuated canine distemper virus (Snyder Hill strain), adenovirus (CAV-2 Manhattan strain), parainfluenza virus (NL-CPI-5 strain), canine parvovirus (NL-35-D) propagated in an established cell line, and an inactivated culture of *Leptospira canicola* and *Leptospira icterohaemorrhagiae*.

QUANTUM DOG 7 by Schering-Plough Animal Health contains canine distemper, adenovirus type 2, parvovirus, parainfluenza virus type 2 vaccine (living) and inactivated *Leptospira canicola* and *Leptospira icterohaemorrhagiae* vaccine.

CANIGEN DHPPi by Virbac Ltd. is a live attenuated, freeze-dried, virus vaccine containing canine distemper virus, canine adenovirus (CAV2), canine parvovirus and canine parainfluenza virus grown in cell line tissue culture.

CANIGEN Ppi by Virbac Ltd. is a live attenuated, freeze-dried virus vaccine containing canine parvovirus and canine parainfluenza virus grown in cell line tissue culture.

Typically, an agent capable of raising an immune response in a dog against CHV comprises inactivated or attenuated CHV, or an immunogenic fragment thereof, or a nucleic acid encoding said immunogenic fraction.

Suitable agents that raise an immune response in a dog against CHV are known to a person of skill in the art. For example, EURICAN Herpes 205 by Merial is a purified subunit vaccine against canine herpesvirus which is indicated for the active immunisation of pregnant bitches to prevent mortality, clinical signs and lesions in puppies resulting from canine herpesvirus infections acquired in the first days of life. It is not licensed for the vaccination of adult dogs for the prevention of respiratory disease.

Typically, an agent capable of raising an immune response in a dog against *B. bronchiseptica* comprises inactivated or attenuated *B. bronchiseptica*, or an immunogenic fragment thereof, or a nucleic acid encoding said immunogenic fraction.

Suitable agents that raise an immune response in a dog against *B. bronchiseptica* are known to a person of skill in the art. For example, the following dog vaccines are licensed for use.

COUGHGUARD-B® by Pfizer Animal Health (U.S. Vet. Lic. No.: 189) contains an inactivated culture of *B. bronchiseptica*. It is for the immunisation of healthy dogs against disease caused by *B. bronchiseptica*, in particular kennel cough. COUGHGUARD-B® is prepared from a highly antigenic strain of *B. bronchiseptica* which has been inactivated and processed to be nontoxic when administered to dogs. The production method is reported to leave the immunogenic properties of *B. bronchiseptica* intact.

VANGUARD® 5/B by Pfizer Animal Health (U.S. Vet. Lic. No.: 189) contains attenuated strains of canine distemper virus (CDV), CAV-2, CPIV, and canine parvovirus (CPV) propagated on an established canine cell line. The CPV antigen was attenuated by low passage on the canine cell line and at that passage level has immunogenic properties capable of overriding maternal antibodies. The vaccine is packaged in lyophilised form with inert gas in place of vacuum. The bacterin component containing inactivated whole cultures of *B. bronchiseptica* which is supplied as diluent. The *B. bronchiseptica* component in VANGUARD® 5/B is prepared from a highly antigenic strain which has been inactivated and processed to be nontoxic when administered to dogs.

NASAGUARD-B™ by Pfizer Animal Health (U.S. Vet. Lic. No.: 112) is composed of an avirulent live culture of *B. bronchiseptica* bacteria.

PROGARD®-KC by Intervet is a modified live intranasal vaccine containing attenuated canine parainfluenza virus and *Bordetella bronchiseptica* avirulent live culture. PROGARD®-KC is presented in a desiccated form with sterile diluent provided for reconstitution. PROGARD®-KC is for vaccination of healthy, susceptible puppies and dogs for prevention of canine infectious tracheobronchitis ("kennel cough") due to canine parainfluenza virus and *B. bronchiseptica*.

PROGARD®-KC PLUS by Intervet contains live culture of avirulent strains of *B. bronchiseptica*, attenuated canine adenovirus type 2 and parainfluenza virus for intranasal administration. Vaccination with PROGARD®-KC Plus stimulates rapid, local immunity in the respiratory tract, thereby inhibiting infection at the port of entry as well as preventing clinical signs. In addition to local immunity, it also stimulates systemic immunity within three weeks of intranasal administration. The small volume (0.4 ml) and one nostril application of PROGARD®-KC Plus provide for ease in vaccination, particularly in small breeds and young puppies. PROGARD®-KC Plus is presented in a desiccated form with sterile diluent provided for reconstitution. PROGARD®-KC Plus is for vaccination of healthy dogs and puppies three weeks of age or older for prevention of canine infectious tracheobronchitis ("kennel cough") due to canine adenovirus type 2, parainfluenza virus and *B. bronchiseptica*.

Intrac by Intervet is a freeze dried modified live vaccine, containing *B. bronchiseptica* strain S 55, for intranasal administration. Product licence number PL 0201/4011

Nobivac KC, described above, also contains *B. bronchiseptica*.

Vaccination would be useful especially but not exclusively for dogs prior to entry into a boarding kennel or for the vaccination of dogs in breeding facilities.

A typical dose of a vaccine comprised of recombinant protein is about 5-10 µg. A typical dose of a vaccine comprised of inactivated virus is about 1-10 mg.

In a ninth aspect, the invention provides the use of (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronaviral protein having at least 75% amino acid identity with a BCV protein, or an immunogenic fragment thereof, or (vii) a nucleic acid encoding said coronaviral protein or immunogenic fraction thereof, in the preparation of a medicament for stimulating an immune response against CRCV in a dog.

The invention includes the use of (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronaviral protein having at least 75% amino acid identity with a BCV protein, or an immunogenic fragment thereof, or (vii) a nucleic acid encoding said coronaviral protein or immunogenic fraction thereof, in the preparation of a medicament for prophylaxis of respiratory disease in a dog, typically CIRD.

When a coronavirus protein, or an immunogenic fragment thereof, is used in the preparation of the medicament, the protein preferably has at least 80%, or at least 85%, or at least 90%, or at least 95% amino acid identity with the corresponding portion of a BCV protein. Preferably the protein has at least 80%, or at least 85%, or at least 90%, or at least 95% amino acid identity with the corresponding portion of a CRCV protein.

Preferably, the coronaviral protein used in the preparation of the medicament is a BCV, HCV, HEV or CRCV protein, or a modification thereof, as described above with reference to the eighth aspect of the invention.

More preferably, the coronaviral protein used in the preparation of the medicament is an S protein. Yet more preferably, the S protein comprises an CRCV or CRCV-like S protein as defined above in the first aspect of the invention or obtainable by the methods of the fourth aspect of the invention, a BCV S protein, an HCV S protein, or an immunogenic fragment thereof.

Most preferably, the coronaviral protein used in the preparation of the medicament comprises or consists of the amino acid sequence listed in FIG. 4, or an immunogenic fragment thereof having at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Additionally or alternatively, the coronaviral protein used in the preparation of the medicament may comprise HE, E, M or N coronavirus proteins. In one embodiment, the HE, E, M or N proteins are BCV, HCV or HEV proteins. In another embodiment, the HE, E, M or N proteins are CRCV proteins.

Typically, the HE protein comprises an CRCV or CRCV-like HE protein as defined above in the third aspect of the invention or obtainable by the methods of the fourth aspect of the invention, a BCV HE protein, an HCV HE protein, or an immunogenic fragment thereof.

Preferably, the coronaviral HE protein used in the preparation of the medicament comprises or consists of the partial amino acid sequence listed in FIG. 14, or an immunogenic fragment thereof having at least 97% identity with the sequence listed in FIG. 14. Preferably, the variant has at least 98%, or at least 99% amino acid sequence identity with the sequence listed in FIG. 14. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the partial sequence listed in FIG. 14.

When a coronavirus is used in the preparation of the medicament, the coronavirus preferably comprises an S protein with at least 80%, or at least 85%, or at least 90%, or at least 95% amino acid identity with the BCV S protein. More preferably the coronavirus comprises an S protein with at least 80%, or at least 85%, or at least 90%, or at least 95% amino acid identity with the CRCV S protein.

Additionally or alternatively, the coronavirus may comprise an HE protein with at least 90%, or at least 95% amino acid identity with the BCV HE protein. More preferably the coronavirus comprises an HE protein with at least 96%, or at least 97%, or at least 98%, or at least 99% amino acid identity with the CRCV HE protein.

In a tenth aspect, the invention provides a CRCV or CRCV-like S protein as defined above in the first aspect of the invention or obtainable by the methods of the fourth aspect of the invention, for use in medicine. Typically, the S protein will be used in veterinary medicine.

The invention includes a CRCV or CRCV-like HE protein as defined above in the third aspect of the invention or obtainable by the methods of the fourth aspect of the invention, for use in medicine. Typically, the HE protein will be used in veterinary medicine.

In an eleventh aspect, the invention provides a method of vaccinating a dog against CRCV, the method comprising administering to the dog a vaccine composition as described above in the ninth aspect of the invention.

Typically, the vaccine will be administered via the intramuscular, subcutaneous or intranasal routes In another embodiment, a dog can passively acquire immunity against CRCV by being administered an antibody that reacts with CRCV. The antibody that reacts with CRCV may be an anti-BCV, anti-HCV antibody, but is preferably an anti-CRCV antibody. Preferably, the antibody that reacts with CRCV is an anti-S protein antibody an anti-HE protein antibody. Most preferably, the antibody that reacts with CRCV is an anti-CRCV S or HE protein antibody as described in the fifth aspect of the invention.

In a twelfth aspect, the invention provides a method for combating the spread of CRCV between dogs comprising determining whether a dog is infected with CRCV according to the methods as described above in the sixth aspect of the invention, or using the immunosorbent assay or solid substrate as described above in the seventh aspect of the invention, and, if the dog is infected with CRCV, quarantining the dog.

By "quarantining" a dog we include the meaning of keeping the dog separate from all other dogs. We also include the meaning of keeping the dog separate from dogs that have not been vaccinated against CRCV, which can be performed as described above. We also include the meaning of keeping the dog separate from dogs that have not been infected by CRCV, which can be determined as described above.

In a thirteenth aspect, the invention provides a method for combating the spread of CRCV between dogs comprising determining whether a dog is infected with CRCV according to the methods described above in the sixth aspect of the invention, or using the immunosorbent assay or solid substrate as described above in the seventh aspect of the invention, and, if the dog is infected with CRCV, vaccinating other dogs that have been, are, or are likely to be in contact with the dog.

A fourteenth aspect of the invention provides a method for identifying a test vaccine capable of preventing or reducing the incidence of canine infectious respiratory disease (CIRD) in dogs. The method comprises (a) determining whether a dog has been exposed to CRCV, typically according to the methods described above in the sixth aspect of the invention or using the immunosorbent assay or solid substrate as described above in the seventh aspect of the invention, (b) if the dog has not been exposed to CRCV, administering the test vaccine to the dog, (c) inoculating the dog with CRCV, and (d) determining whether the dog develops CIRD. The absence of CIRD in step (d) indicates that the test vaccine is capable of preventing CIRD.

Typically, this method is performed on a set of dogs.

Preferably, the method involves the use of a set of control dog which are not administered the test vaccine in step (b). The significantly lower incidence of CIRD in the set of dogs that has been administered the test vaccine than in the control set indicates that the test vaccine is capable of preventing or reducing the incidence of CIRD.

The invention also includes a vaccine identified by this method.

All of the documents referred to herein are incorporated herein, in their entirety, by reference.

The invention will now be described in more detail with the aid of the following Figures and Examples.

BRIEF DESCRIPTION OF THE DRAWINGS

FIG. 1
Partial nucleotide sequence (250 residues) of the CRCV polymerase (pol) cDNA (SEQ ID NO: 1).

FIG. 2
Partial amino acid sequence (83 residues) of the CRCV pol protein (SEQ ID NO: 2), derived from the nucleotide sequence of FIG. 1.

FIG. 3
Nucleotide sequence (4092 residues) of the CRCV Spike (S) cDNA (SEQ ID NO: 3). The Y at position 3531 refers to either C or T.

FIG. 4
Amino acid sequence (1363 residues) of the CRCV S protein (SEQ ID NO: 4), derived from the nucleotide sequence of FIG. 3.

Figure 5:
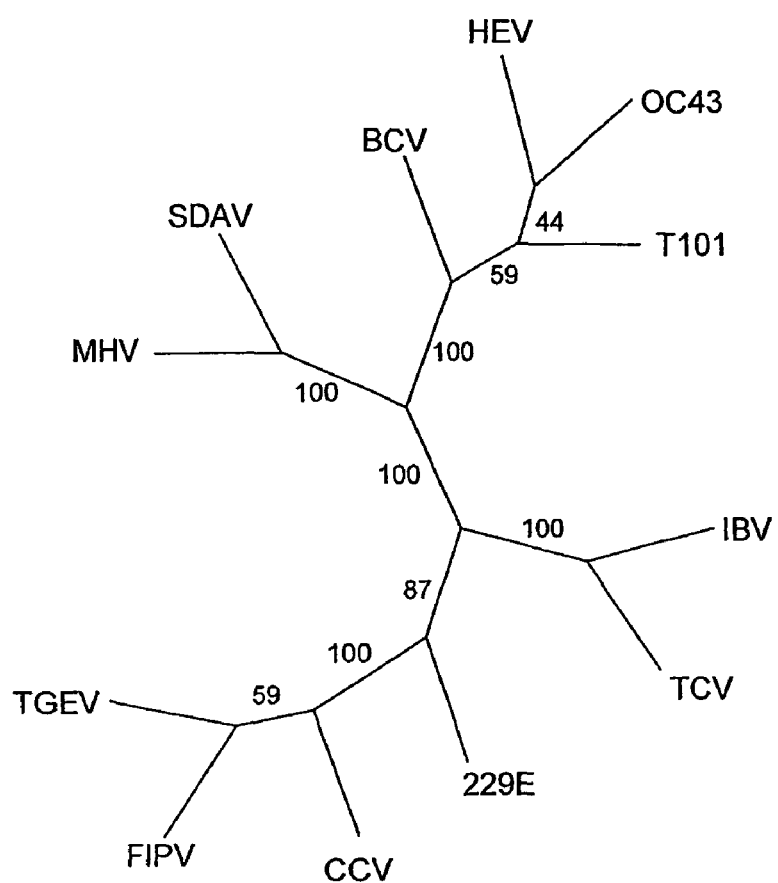
FIG. 5
Consensus tree for cDNA sequences from a 250 nucleotide region of the polymerase gene of 12 coronaviruses. The sequence obtained from the canine respiratory coronavirus is designated T101. The numbers indicate bootstrap values obtained by analysis of 100 data sets.

BCV: bovine coronavirus, CCV: canine coronavirus, FIPV: feline infectious peritonitis virus, HEV: hemagglutinating encephalomyelitis virus, IBV: infectious bronchitis virus, MHV: mouse hepatitis virus, OC43: human coronavirus strain OC43, SDAV: sialodacryoadenitis virus, TCV: turkey coronavirus, TGEV: transmissible gastroenteritis virus, 229E: human coronavirus strain 229E, T101: canine respiratory coronavirus (PCR product from tracheal sample T101)

FIG. 6

CLUSTAL X (1.8) multiple sequence alignment of the 250 nucleotide partial sequence of the pol cDNA of CRCV (sample T101, SEQ ID NO: 1), BCV (SEQ ID NO: 5), HCV strain OC43 (SEQ ID NO: 6), HEV (SEQ ID NO: 7) and CCV (enteric CCV, SEQ ID NO: 8).

FIG. 7

CLUSTAL X (1.8) multiple sequence alignment of the 83 amino acid partial sequence of the pol protein of CRCV (protCRCVpol, SEQ ID NO: 2) with HCV (protHCVpoly, SEQ ID NO: 9), HEV (protHEVpoly, SEQ ID NO: 10), BCV (protBCVpoly, SEQ ID NO: 11) and CECV (enteric CCV, protCECVpol, SEQ ID NO: 12).

FIG. 8

CLUSTAL X (1.8) sequence alignment of the nucleotide sequence of the CRCV spike cDNA (CRCVspike, SEQ ID NO: 3) and enteric CCV spike cDNA (CECVspike, SEQ ID NO: 13).

FIG. 9

CLUSTAL X (1.8) multiple sequence alignment of the 4092 nucleotides of the CRCV spike cDNA (CRCVspike, SEQ ID NO: 3) sequence with BCV (BCVspike, SEQ ID NO: 14), HCV (HCVspike, SEQ ID NO: 15) and HEV (HEVspike, SEQ ID NO: 16) spike cDNAs. The Y at position 3531 in the CRCV sequence refers to either C or T.

FIG. 10

CLUSTAL X (1.8) multiple sequence alignment of the 1363 amino acid sequence of the CRCV spike protein (CRCVspikepr, SEQ ID NO: 4) with BCV (BCVspikepro, SEQ ID NO: 17), HCV (HCVspikepro, SEQ ID NO: 18), HEV (HEVspikepro, SEQ ID NO: 19) and enteric CCV (CECVspikepr, SEQ ID NO: 20) spike proteins.

FIG. 11

RT-PCR using nested set of primers (Spike 1 and 2 (SEQ ID NOS: 34 and 35) followed by Spike 3 and 4 (SEQ ID NOS: 36 and 37)). BCV: Bovine coronavirus positive control sample; A72: Coronavirus negative A72 cells; H$_2$O: PCR mix without DNA; T5-T21: Tracheal samples of study dogs. The agarose gel electrophoresis shows PCR products of the expected size of 442 bp for the positive control (BCV) and samples T12 and T21.

FIG. 12

Comparison of the prevalence of respiratory disease in two groups of dogs. Dogs in group 1 were positive for serum antibodies to respiratory coronavirus on day of entry into the kennel, dogs in group 2 were negative. The graph shows the percentage of dogs developing respiratory disease in group 1 compared to group 2 (p<0.001). n is the total number of dogs in each group.

FIG. 13

Partial nucleotide sequence (497 residues) of the CRCV hemagglutinin/esterase (HE) gene (SEQ ID NO: 21). The sequence corresponds to nucleotides 418 to 914 of the HE genes of BCV (GenBank M84486) and HCV OC43 (GenBank Accession No. M76373).

FIG. 14

Partial amino acid sequence (165 residues) of the CRCV HE protein (SEQ ID NO: 22), derived from the nucleotide sequence of FIG. 13. This sequence corresponds to amino acid residues 140 to 304 of BCV (GenBank M84486) and HCV OC43 (GenBank Accession No. M76373).

FIG. 15

CLUSTAL X (1.8) multiple sequence alignment of a 497 nucleotide partial sequence of the hemagglutinin/esterase (HE) gene of CRCV (canine respiratory coronavirus, SEQ ID NO: 21) with BCV (bovine coronavirus strain LY138, (SEQ ID NO: 23, taken from Genbank Accession No. AF058942), OC43 (human coronavirus strain OC43, SEQ ID NO: 24 taken from Genbank Accession No. M76373), HECV (human enteric coronavirus, SEQ ID NO: 25, taken from Genbank Accession No. L07747), and HEV (hemagglutinating encephalomyelitis virus, SEQ ID NO: 26, taken from Genbank Accession No. AF481863).

FIG. 16

CLUSTAL X (1.8) multiple sequence alignment of a 165 amino acid partial sequence of the HE protein of CRCV (canine respiratory coronavirus, (SEQ ID NO: 22) with BCV (bovine coronavirus strain LY138, SEQ ID NO: 27, taken from Genbank Accession No. AF058942), OC43 (human coronavirus strain OC43, SEQ ID NO: 28, taken from Genbank Accession No. M76373), HECV (human enteric coronavirus, SEQ ID NO: 29, taken from Genbank Accession No. L07747), and HEV (hemagglutinating encephalomyelitis virus, SEQ ID NO: 30, taken from Genbank Accession No. AF481863). The three CRCV-specific amino acids F, N and L are indicated in bold and are underlined.

FIG. 17

RT-PCR using consensus primers HE1 (SEQ ID NO: 38) and HE2 (SEQ ID NO: 39) directed to the HE gene of BCV and HCV (strain OC43). The agarose gel electrophoresis shows a PCR product of the expected size of 497 bp for the BCV positive control and for four tracheal samples from study dogs (T90, T91, T101 and T105), and not for coronavirus-negative A72 cells or the PCR mix without DNA (H$_2$O). 1 kb indicates a molecular size standard (Promega).

FIG. 18

CRCV Spike gene cloning strategy.

DETAILED DESCRIPTION OF THE INVENTION

EXAMPLE 1

Detection of a Novel Coronavirus Associated with Canine Infectious Respiratory Disease Summary An investigation into the causes of canine infectious respiratory disease (CIRD) was carried out in a large re-homing kennel. Tissue samples taken from the respiratory tract of diseased dogs were tested for the presence of coronaviruses using RT-PCR with conserved primers for the polymerase gene. Sequence analysis of four positive samples showed the presence of a novel coronavirus with high similarity to both bovine and human coronavirus (strain OC43) in their polymerase and spike genes whereas there was a low similarity to comparable genes in the enteric canine coronavirus. This canine respiratory coronavirus (CRCV) was detected by RT-PCR in 32/119 tracheal and 20/119 lung samples with the highest prevalence being detected in dogs with mild clinical symptoms. Serological analysis showed that the presence of antibodies against CRCV on the day of entry into the kennel decreased the risk of developing respiratory disease.

Materials and Methods

Study Population

Dogs from a well-established re-homing kennel with a history of endemic respiratory disease were monitored for this study. On entry into the kennel, all dogs were vaccinated with KAVAK DA$_2$ PiP69 (Fort Dodge) a live attenuated vaccine for distemper virus, canine adenovirus type 2, canine parainfluenzavirus and canine parvovirus. Also, a killed leptospirosis vaccine was used (Fort Dodge). The health status of each dog was assessed twice a day by a veterinary clinician and the respiratory symptoms were graded as follows: 1: no respiratory signs, 2: mild cough, 3: cough and nasal discharge, 4: cough, nasal discharge and inappetence, 5: bronchopneumonia. The overall health status of the dogs was graded as follows: 1: good health, 2: poor health, 3: very poor health. The age, breed and sex of the dogs were recorded.

For 119 dogs a full post mortem examination was performed. The tissue samples were stored at −70° C. until further use.

Serum samples were collected from 111 dogs on day of entry into the re-homing kennel. For 81 dogs a follow-up serum was available on day 7 and for 111 dogs a serum was available on day 21 after entry.

Of the 111 dogs, 30 remained healthy during the 21 days between the first and the last serum sample whereas 81 dogs developed respiratory disease.

Sera from 35 dogs housed elsewhere were obtained from the diagnostic service of the Royal Veterinary College. These sera had been submitted for biochemical analysis for various reasons. Five of these sera were from 18-month-old beagles with no history of respiratory disease. Sera were routinely stored at −20° C.

RNA Extraction and RT-PCR

RNA was extracted from tracheal and lung tissue of 119 dogs using TriReagent (Sigma). Approximately 25-50 mg of homogenised tissue was used and RNA was extracted as recommended by the manufacturer.

Synthesis of cDNA was performed using Random Hexamers (Roche) and ImPromII reverse transcriptase (Promega).

The polymerase gene of coronaviruses is known to be highly conserved, and has previously been used for phylogenetic analysis of this virus family (Stephensen et al., 1999). For the detection of coronaviruses a modification of the primers 2 Bp and 4Bm directed against the polymerase gene as described by Stephensen et al. (1999) were used (Conscoro5: 5'-ACT-CAR-ATG-AAT-TTG-AAA-TAT-GC (SEQ ID NO: 31); and Conscoro6: 5'-TCA-CAC-TTA-GGA-TAR-TCC-CA (SEQ ID NO: 32)).

PCR was performed using Taq polymerase (Promega) in the provided reaction buffer containing a final concentration of 2.5 mM MgCl$_2$ and 0.5 µM of primers. For PCR with the primers Conscoro5 and Conscoro6 the following temperature profile was used: After denaturation at 95° C. for 5 min, 10 cycles were carried out at 95° C. for 1 min, annealing at 37° C. for 1 min and extension at 72° C. for 1 min. This was followed by 10 cycles using an annealing temperature of 45° C., 10 cycles at an annealing temperature of 50° C. and 10 cycles at an annealing temperature of 53° C. followed by a final extension at 72° C. for 10 min.

A 20 µl fraction of the PCR product was analysed on a 1.5% agarose gel and blotted onto a nylon membrane (Roche) after electrophoresis. The nylon membrane was hybridised with an oligonucleotide probe specific for the PCR product at 37° C. overnight (Probe Conscoro: AAG-TTT-TAT-GGY-GGY-TGG-GA (SEQ ID NO: 33)). The probe was 3' A-tailed with Digoxigenin-dUTP and was detected using anti-Digoxigenin conjugate and CSPD chemoluminescent substrate (Roche).

Primer sequences specific for the spike gene were derived from an alignment of the spike region of bovine coronavirus strain LY-138 (AF058942) and human coronavirus strain OC43 (L14643).

A PCR was performed with the primers Spike 1 and Spike 2, followed by a nested PCR using the primers Spike 3 and Spike 4 and 2 µl of the product of the first amplification.

The numbers in brackets refer to the nucleotide position in the bovine coronavirus genome.

```
Spike 1:
5'-CTT-ATA-AGT-GCC-CCC-AAA-CTA-AAT      (25291-25314)

Spike 2:
5'-CCT-ACT-GTG-AGA-TCA-CAT-GTT-TG       (25912-25890)

Spike 3:
5'-GTT-GGC-ATA-GGT-GAG-CAC-CTG          (25320-25339)

Spike 4:
5'-GCA-ATG-CTG-GTT-CGG-AAG-AG           (25762-25742)
```

Oligonucleotide Spike 1 has SEQ ID NO: 34, Spike 2 has SEQ ID NO: 35, Spike 3 has SEQ ID NO: 36, Spike 4 has SEQ ID NO: 37.

The temperature profile used was denaturation at 95° C. for 5 min, followed by 35 cycles of denaturation at 95° C. for 1 min, annealing at 55° C. for 40 sec and elongation at 72° C. for 1 min. The final extension was performed at 72° C. for 10 min. The nested PCR produced a 442 bp fragment.

PCR products were cloned into the pGEM-T-easy vector (Promega) and sequenced using the Thermo sequenase fluorescent labelled primer cycle sequencing kit with 7-deaza-dGTP (Amersham Pharmacia) using Cy5 labelled primers.

Phylogenetic Analysis

An alignment of the 250 bp cDNA sequence from the polymerase gene to the corresponding sequences of 11 coronaviruses was performed using ClustalX (Thompson et al., 1997).

The phylogenetic relationship to known coronaviruses was analysed using the Phylip 3.6 package (Felsenstein, 1989). The alignments were followed by a bootstrap analysis using the Seqboot programme. The obtained data sets were used for a maximum parsimony analysis using the DNApars programme and a consensus tree was calculated using Consense. The resulting trees were drawn using the Treeview programme (Page, 1996).

ELISA

ELISA antigen for bovine coronavirus or enteric canine coronavirus (CECV) (the antigens are a preparation from virus infected cell cultures obtained from Churchill Applied Biosciences, Huntingdon, UK) was resuspended in PBS at the concentration recommended by the manufacturer and incubated on 96 well plates (Falcon) overnight at 37° C.

The plates were washed with PBS and blocked with PBS containing 5% skimmed milk powder for 30 min. The sera were diluted 1:100 in blocking buffer and incubated on the plates for 1 h. After washing with PBS/0.05% Tween 20 (Sigma), a peroxidase labelled rabbit anti-dog IgG conjugate (Sigma) was added (1:5000 in PBS/0.05% Tween 20) for 1 h. The plates were incubated with colour substrate (OPD, Sigma) for 10 min and the reaction was stopped by adding 2M H$_2$SO$_4$. The adsorption was determined in an ELISA photometer at 492 nm.

Virus Culture

Virus isolation is performed on canine adult lung fibroblasts (passage 3 to 7), MDCK and A72 cells. (It is appreciated, however, that virus isolation could be performed using primary cells or cell lines such as MDCK or A72 (canine), MDBK (bovine), HRT-18 (human rectal tumour cell line) and Vero (African Green Monkey). The lung fibroblasts are maintained in MEM with 20% fetal calf serum (FCS), MDCK and A72 cells are maintained in MEM with 5% FCS. Tracheal tissue samples (approx. 25 mg) are homogenised using a scalpel and mixed vigorously in 1 ml MEM containing Penicillin (100 U/ml), Streptomycin (0.1 mg/ml), Amphotericin B (2.5 µg/ml) and Trypsin (1 µg/ml). The samples are centrifuged at 13000 rpm for 10 min. and the supernatant is used to inoculate cell cultures. After 30 min. at 37° C. the supernatant is removed and maintenance medium added to the cultures. The cultures are passaged three times in the absence of a cytopathic effect. Then, RNA is extracted from the cells and RT-PCR to detect the presence of CRCV is performed.

Statistical Analysis

The data were analysed using the chi-square test or Fisher's exact test and p values below 0.05 were considered statistically significant.

Results

PCR Using Consensus Primers for the Coronavirus RNA Polymerase Gene

Using the primers Conscoro5 and Conscoro6, cDNA obtained from 40 tracheal samples was analysed by RT-PCR.

Out of these, seven were found to be positive by PCR and subsequent hybridisation (17.5%).

The PCR products were cloned and sequenced (FIGS. 1 and 2) and the sequence data were compared to available viral sequences using the FASTA search program (Pearson, 1990).

Comparison of the coronavirus cDNA polymerase sequence obtained from four of the canine tracheal samples to other coronavirus sequences revealed that they were most similar to sequence data from BCV strain Quebec and LY138 (Genbank Accession Nos. AF220295 and AF058942, respectively) and human coronavirus strain OC43 (Genbank Accession No. AF124989).

The similarity in the analysed 250 bp sequence was 98.8% for BCV Quebec, and 98.4% for BCV LY138 and the HCV pol genes, whereas it was only 68.53% for CCV strain 1-71 pol gene (FIGS. 6 and 7).

An alignment of the novel sequence with the corresponding sequences of 11 coronaviruses and phylogenetic analysis using the maximum parsimony method resulted in the consensus tree shown in FIG. 5. The cDNA sequence obtained from a tracheal sample (T101) was found on a common branch with bovine coronavirus, human coronavirus-OC43 and hemagglutinating encephalomyelitis virus.

The virus was called canine respiratory coronavirus (CRCV).

PCR Using Primers for the Spike Gene

Figure 11:
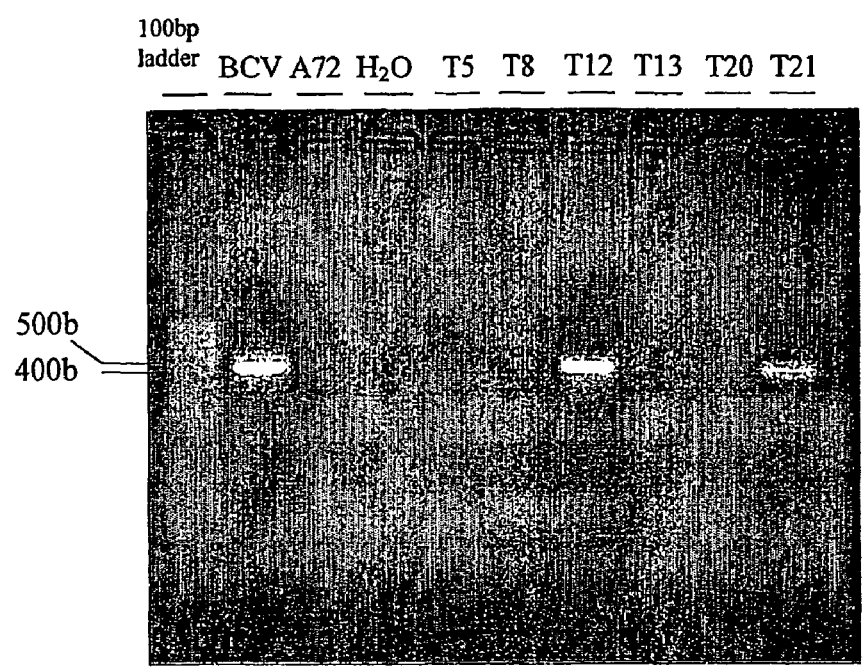

For further analysis of the RNA sequence of CRCV, an alignment of the RNA for the spike gene of the bovine coronavirus LY 138 strain (AF058942) and the human coronavirus OC43 strain (L14643) was performed using Clustal X (Thompson et al., 1997). Consensus regions were chosen for the selection of the nested primer sets Spike 1-2 and Spike 3-4 (FIG. 11). PCR analysis was performed with the cDNA obtained from 119 tracheal and lung samples using these nested primers.

In total 32 tracheal samples (26.9%) and 20 lung samples (16.8%) were found positive by nested PCR. For eight dogs a positive PCR result was obtained for both, trachea and lung.

Sequence analysis of the PCR products obtained from tissues of six different dogs showed identical DNA sequences for these cDNAs (FIGS. 3 and 4). A comparison to known coronavirus spike sequences using the FASTA program revealed a 98.1% similarity to bovine coronavirus and a 97.8% similarity to human coronavirus OC43 (FIGS. 9 and 10).

PCR Using Primers for the HE Gene

Bovine coronavirus and other group II coronaviruses contain an additional structural protein, the hemagglutinin/esterase (HE). Because of the high similarity of CRCV with BCV, we analysed the presence of an HE gene in CRCV.

Figure 17:
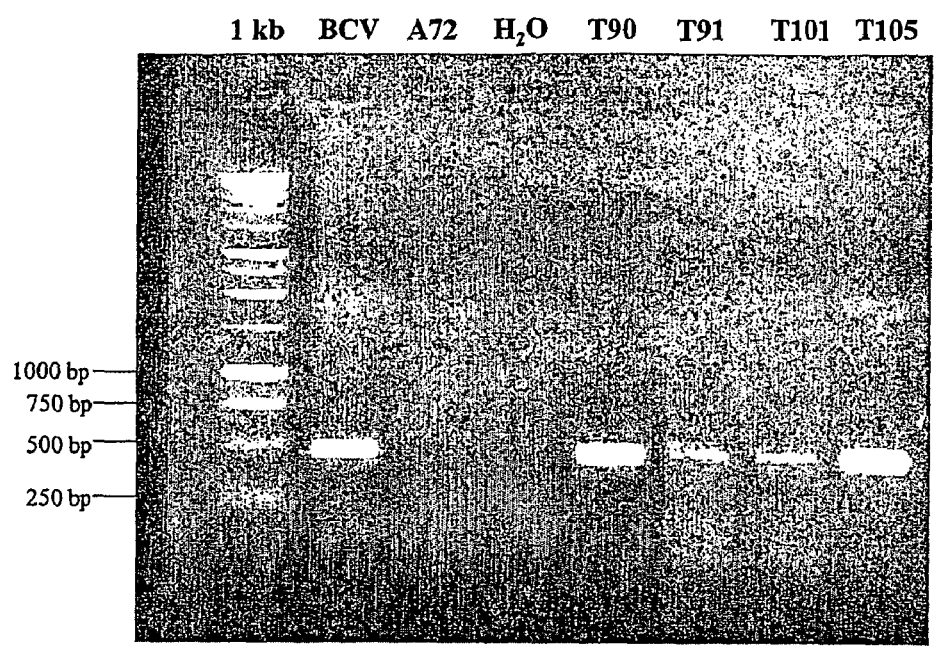

An alignment of the HE genes sequences of BCV and HCv OC43 was used to design the primers HE1 and HE2 (Table 2). Four tracheal samples that had previously been identified as positive for coronavirus RNA by RT-PCR with primers for the S gene were tested by RT-PCR with the primer set for the HE gene. All four samples showed a PCR band of the expected size after agarose gel electrophoresis (FIG. 17).

TABLE 2

Primers designed from an alignment of the hemagglutinin/esterase genes of BCV (GenBank Accession No. M84486) and HCV OC43 (GenBank Accession No. M76373)

| Name | Sequence | Location in BCV HE gene |
|---|---|---|
| HE 1 | 5'-TAT-CGC-AGC-CTT-ACT-TTT-GT | 418-437 |
| HE 2 | 5'-ACC-GCC-GTC-ATG-TTA-TCA-G | 914-896 |

Primer HE1 has SEQ ID No: 38 and HE2 has SEQ ID No: 39. The sequence of the CRCV PCR product obtained using primers HE 1 and HE 2 is given in FIG. 13 (SEQ ID No: 21), and its predicted amino acid sequence is listed in FIG. 14 (SEQ ID No: 22). A comparison of these nucleotide and amino acid sequences with the corresponding fragments of other related coronaviruses is shown in FIGS. 15 and 16. Three amino acids were shown to be unique to CRCV, as shown in Table 3.

TABLE 3

Unique amino acids in CRCV HE gene

| Amino acid in CRCV | Amino acid in BCV/ HECV/ HCV/ HEV | Position in BCV/ HECV/ HCV/ HEV | Position in PCR product HE1-HE2 |
|---|---|---|---|
| F (Phe) | L (Leu) | 235 | 96 |
| N (Asn) | T (Thr) | 242 | 103 |
| L (Leu) | V (Val) | 253 | 114 |

The amino acid positions in BCV, HECV, HCV and HEV are numbered from the initial M (which is number 1) at the start of the BCV and HCV OC43 HE proteins (GenBank Accession Nos. M84486 and M76373, respectively).

Association of PCR Positive Samples with Respiratory Signs

Using primers for the spike gene, tracheal and lung samples from 119 dogs were analysed by RT-PCR for CRCV. Of these 42 were from dogs with no respiratory signs (grade 1), 18 dogs had shown mild respiratory signs (grade 2), 46 had shown moderate (grade 3) and 13 severe respiratory signs (grades 4 and 5). Grades 4 and 5 were merged due to the low case numbers in these groups.

Table 4 shows the PCR results for coronavirus in dogs with different grades of respiratory disease. Specifically, Table 4 shows the RT-PCR results from tracheal and lung samples of 119 dogs with different respiratory signs (none to severe) using a nested PCR directed against the coronavirus spike gene as well as the number of positive samples out of total sample number and the percentage of positive samples (in brackets).

TABLE 4

RT-PCR results for tracheal and lung samples

| Respiratory signs | Trachea: Positive samples | Lung Positive samples | Trachea and lung Positive samples |
|---|---|---|---|
| None | 11/42 (26.2%) | 8/42 (19.1%) | 2/42 |
| Mild | 10/18 (55.6%) | 4/18 (22.2%) | 4/18 |
| Moderate | 9/46 (19.6%) | 8/46 (17.4%) | 2/46 |
| Severe | 2/13 (15.4%) | 0/13 | 0/13 |

Establishment of a Serological Assay for CRCV

Because of the homology of the spike cDNA of CRCV to the spike region of bovine coronavirus, an ELISA antigen for BCV was used for serological analysis of CRCV.

Sera from five dogs with no history of infectious respiratory disease that had not been housed in the investigated kennel were tested. The OD values ranged from −0.013 to 0.39 with an average OD value of 0.154. Furthermore, sera from 30 dogs admitted to a veterinary clinic for various reasons were tested for antibodies to coronavirus. Of these, 20 samples showed an OD of <0.4 (−0.46 to 0.396) and 10 samples showed an OD of >1.0 (1.012 to 1.949). Samples with an OD of 0.6 or above were subsequently considered positive.

Comparison of the Immune Response to CRCV of Dogs with and Without Respiratory Disease The BCV-antigen ELISA was performed using paired sera of 111 dogs from the study kennel. Of these, 81 dogs had shown symptoms of respiratory disease during a period of 21 days and 30 had remained healthy.

Of the group of dogs with respiratory disease, 17 were positive for antibodies to CRCV on the day of entry into the kennel and 64 were negative.

Of the 64 dogs with no detectable antibodies to BCV on day one, 63 tested positive on day 21. All 46 dogs out of these 63 for which a sample on day 7 was available tested negative on day 7. Therefore 63 dogs showed a seroconversion during the study-period whereas only one dog remained negative.

Of the 31 dogs that had remained healthy, 17 had antibodies to CRCV on the day of entry. All of the 13 dogs that were negative on day 1 tested negative on day 7 but showed a seroconversion by day 21.

Figure 12:
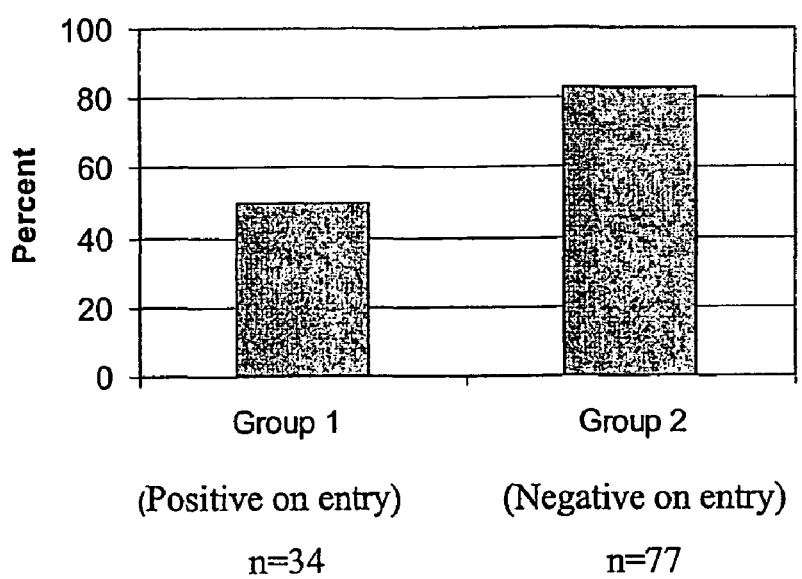

Thus, of 34 dogs that were positive for antibodies to CRCV on arrival in the kennel, 17 developed respiratory disease (50%) whereas of 77 dogs that were negative on arrival, 64 developed respiratory signs during the study-period (83.1%), (FIG. 12).

Therefore dogs that had no antibodies to CRCV on entry into the kennel had an increased probability of developing respiratory disease (p<0.001).

Only one out of the 77 dogs that were negative on arrival remained negative during the study period of 21 days whereas 76 dogs showed a seroconversion.

Serology Using Canine Enteric Coronavirus (CECV) Antigen

An ELISA assay using a canine coronavirus antigen was performed to investigate whether CRCV showed a serological cross reaction to canine enteric coronavirus. Sera from 27 dogs, previously tested for antibodies to CRCV using the BCV antigen were selected.

It was found that eight dogs had antibodies to CECV on the day of entry into the kennel, of these four also had antibodies to CRCV. Nineteen dogs were found to be negative for CECV on day 1, 17 of these were also negative for CRCV. Of the 19 negative dogs, five showed a seroconversion to CECV during the 21-day period of the investigation and 17 showed a seroconversion to CRCV.

Analysis of the prevalence of respiratory disease in this group showed that six out of the eight dogs (75%) that were positive for antibodies to CECV on day 1 developed respiratory disease. Out of the group of 19 dogs that had no detectable antibodies to CECV on day 1, 15 showed signs of respiratory disease (78.9%), (p=0.594).

Virus Isolation

Tracheal tissue samples from dogs that are identified as positive for CRCV RNA by RT-PCR are inoculated on cell cultures of canine adult lung fibroblasts and MDCK cells. For some samples, virus isolation is also performed on A72 cells. The cultures show no signs of a cytopathic effect during three passages. After several passage, RNA is extracted from the cultures and tested for the presence of CRCV RNA by RT-PCR.

DISCUSSION

This study reports the detection of a novel coronavirus, CRCV, in kenneled dogs with respiratory disease.

Coronaviruses have been reported to cause respiratory disease of man, cattle, swine and poultry, but their presence in the respiratory tract of dogs and a possible association with canine infectious respiratory disease (CIRD) has not been determined.

Dogs were investigated from a kennel in which CIRD was endemic and could not be controlled by the use of vaccines recommended against CIRD. Samples taken from the respiratory tract of these dogs were examined using RT-PCR primers directed to the conserved polymerase gene of coronaviruses (Stephensen et al., 1999).

Initially, seven tracheal samples were found to be positive; the sequence of the RT-PCR products was determined and compared to all available coronavirus polymerase gene sequences. This analysis revealed that the cDNA sequence obtained from the canine samples had the highest similarity to the polymerase gene of bovine coronavirus (98.8%) and human coronavirus OC43 (98.4%) but only a very low similarity to the polymerase gene of the enteric canine coronavirus (strain 1-71, 68.53% similarity).

A phylogenetic analysis was performed using the polymerase sequences of eleven additional coronaviruses. The coronavirus detected in the respiratory tract of dogs (CRCV) was located on a common branch with three group 2 viruses: BCV, HCV strain OC43 and HEV. However, canine enteric coronavirus, a group 1 coronavirus, was shown to be only distantly related.

Canine respiratory coronavirus therefore is a novel coronavirus of dogs that is most closely related to BCV and HCV-OC43, both of which are known to cause respiratory disease.

To obtain more sequence information and to further determine the relationship to other coronaviruses using a more variable gene, a part of the spike gene was analysed. Since CRCV bad been shown to be most similar to BCV and HCV-OC43, an alignment of the sequences of their spike genes was used to design a nested set of primers. Nested primers were chosen to achieve a more sensitive assay.

Sequencing of the products of this RT-PCR confirmed the high similarity of CRCV with BCV and HCV-OC43.

The presence of antibodies to CRCV was analysed using an ELISA based on a BCV antigen because of the high sequence similarity of the two viruses in the spike cDNA. The ELISA results confirmed the presence of a virus similar to BCV in the study population.

The prevalence of antibodies was 30% at the time of entry into the kennel and 99% after 21 days.

Interestingly and unexpectedly, serological analysis revealed that dogs with antibodies to CRCV on day of entry into the kennel developed respiratory disease less frequently than dogs without antibodies (p<0.001). Therefore the presence of antibodies to CRCV bad a protective effect against respiratory disease in this population.

Almost all dogs negative on day of entry into the kennel showed a seroconversion to CRCV within three weeks, indicating that the virus is highly contagious. Serology using an antigen for canine enteric coronavirus (CECV) showed a much lower prevalence of antibodies to CECV on day 21. Therefore the BCV-ELISA results did not reflect an infection with canine enteric coronavirus and the cross-reactivity between the two antigens seems to be low.

Serum antibodies to CRCV were present in about 30% of dogs of various origins including dogs entering a re-homing kennel as well as pet dogs. The presence of CRCV is therefore not limited to the investigated kennel and the virus seems to be established in the dog population.

By PCR, CRCV was detected in tracheal tissue and lung tissue and therefore appears to infect the upper and lower respiratory tract of dogs. Within the kenneled population, CRCV-RNA was detected in 27.3% of dogs with all grades of respiratory disease as well as in 26.2% of dogs that were apparently healthy at the time of euthanasia.

CRCV-RNA was most frequently found in the trachea of dogs with mild cough (55%). Studies using the human coronavirus strain 229E have shown, that coronaviruses can cause disruption of the respiratory epithelium and ciliary dyskinesia (Chilvers et al., 2001). Without being bound by theory, we believe that an infection with CRCV has a similar effect, and that the virus plays an important role in the early stages of the pathogenesis of CIRD. By damaging the respiratory epithelium and disrupting ciliary clearance CRCV facilitates the entry of other viral or bacterial pathogens. Therefore while CRCV infection on its own may cause only mild respiratory symptoms, in conjunction with other pathogenic agents it could lead to severe respiratory disease.

The pathogenesis of CIRD has not been thoroughly investigated since the 1970s when Bordetella bronchiseptica, canine adenovirus type 2 and canine parainfluenza were determined to be the main causes of the disease. However the vaccination of all dogs against CPIV, CAV-2 and distemper virus did not help to control the disease in this kennel despite evidence that the majority of dogs responded to the vaccine within 21 days (data not shown).

This study shows an association of a novel canine respiratory coronavirus with CIRD. The aetiology of CIRD therefore needs to be re-evaluated and the role of novel microorganisms or microorganisms previously not associated with the disease has to be established.

REFERENCES

Appel, M., and Binn L. N. (1987) Canine infectious tracheobronchitis, Short review: kennel cough. In "Virus infections of carnivores" (M. Appel Ed.), 1st Edition, pp 201-211 Elsevier Science Publishers, Amsterdam).

Bemis, D. A., Carmichael, L. E., and Appel, M. J. (1977). Naturally occurring respiratory disease in a kennel caused by Bordetella bronchiseptica. Cornell Vet. 67, 282-93.

Binn, L. N., Alford, J. P., Marchwicki, R. H., Keefe, T. J., Beattie, R. J., and Wall, H. G. (1979). Studies of respiratory disease in random-source laboratory dogs: viral infections in unconditioned dogs. Lab Anim Sci. 29, 48-52

Binn, L. N., Eddy, G. A., Lazar, E. C., Helms, J., and Murnane, T. (1967). Viruses recovered from laboratory dogs with respiratory disease. Proc Soc Exp Biol Med 126, 140-5

Chilvers, M. A., McKean, M., Rutman, A., Myint, B. S., Silverman, M., and O'Callaghan, C. (2001). The effects of coronavirus on human nasal ciliated respiratory epithelium. Eur Respir J. 18, 965-70.

Ditchfield, J., Macpherson, L. W., and Zbitnew, A. (1962). Association of a canine adenovirus (Toronto A 26/61) with an outbreak of laryngotracheitis ("kennel cough"). Can. Vet. Jour. 3, 238-247

Felsenstein, J. (1989). PHYLIP-Phylogeny Inference Package (Version 3.2c). Cladistics 5, 164-166

Ignjatovic, J., and Sapats, S. (2000). Avian infectious bronchitis virus. Rev Sci Tech. 19, 493-508.

Karpas, A., King, N. W., Garcia, F. G., Calvo, F., and Cross, R. E. (1968). Canine tracheobronchitis: Isolation and characterization of the agent with experimental reproduction of the disease. Proc Soc Exp Biol Med. 127, 45-52.

Keil, D. J., and Fenwick, B. (1998). Role of Bordetella bronchiseptica in infectious tracheobronchitis in dogs. J Am Vet Med Assoc. 15, 200-7.

Lou, T. Y., and Wenner, H. A. (1963). Natural and experimental infection of dogs with reovirus, type 1: pathogenicity of the strain for other animals. Am. J. Hyg. 77, 293-304.

Makela, M. J., Puhakka, T., Ruuskanen, O., Leinonen, M., Saikku, P., Kimpimaki, M., Blomqvist, S., Hyypia, T., Arstila, P. (1998). Viruses and bacteria in the etiology of the common cold. J Clin Microbiol. 36, 539-42.

Page, R. D. M. Treeview: An application to display phylogenetic trees on personal computers. Computer Applications in the Biosciences 1996 12: 357-358

Pearson W R. Rapid and sensitive sequence comparison with FASTP and FASTA. Methods Enzymol. 1990; 183:63-98.

Pensaert M, Callebaut P, Vergote J. Isolation of a porcine respiratory, non-enteric coronavirus related to transmissible gastroenteritis. Vet Q. 1986 July; 8(3):257-61.

Randolph J F, Moise N S, Scarlett J M, Shin S J, Blue J T, Bookbinder P R. Prevalence of mycoplasmal and ureaplasmal recovery from tracheobronchial lavages and prevalence of mycoplasmal recovery from pharyngeal swab specimens in dogs with or without pulmonary disease. Am J Vet Res. 1993 March; 54 (3):387-91.

Spaan W, Cavanagh D, Horzinek M C. Coronaviruses: structure and genome expression. J Gen Virol. 1988 December; 69 (Pt 12):2939-52.

Stephensen C B, Casebolt D B, Gangopadhyay N N. Phylogenetic analysis of a highly conserved region of the polymerase gene from 11 coronaviruses and development of a consensus polymerase chain reaction assay. Virus Res. April; 60 (2):181-9.

Storz J, Purdy C W, Lin X, Burrell M, Truax R E, Briggs R E, Frank G H, Loan R W Isolation of respiratory bovine coronavirus, other cytocidal viruses, and Pasteurella spp from cattle involved in two natural outbreaks of shipping fever. J Am Vet Med Assoc. 2000 May 15; 216(10):1599-604.

Tennant B J, Gaskell R M, Jones R C, Gaskell C J. Studies on the epizootiology of canine coronavirus. Vet Rec. 1993 Jan. 2; 132(1):7-11.

Thompson J D, Gibson T J, Plewniak F, Jeanmougin F, Higgins D G The ClustalX windows interface: flexible strategies for multiple sequence alignment aided by quality analysis tools. Nucleic Acids Res. 1997 Dec. 15; 25(24): 4876-82.

EXAMPLE 2

Cloning and Expression of CRCV Spike

Figure 18:
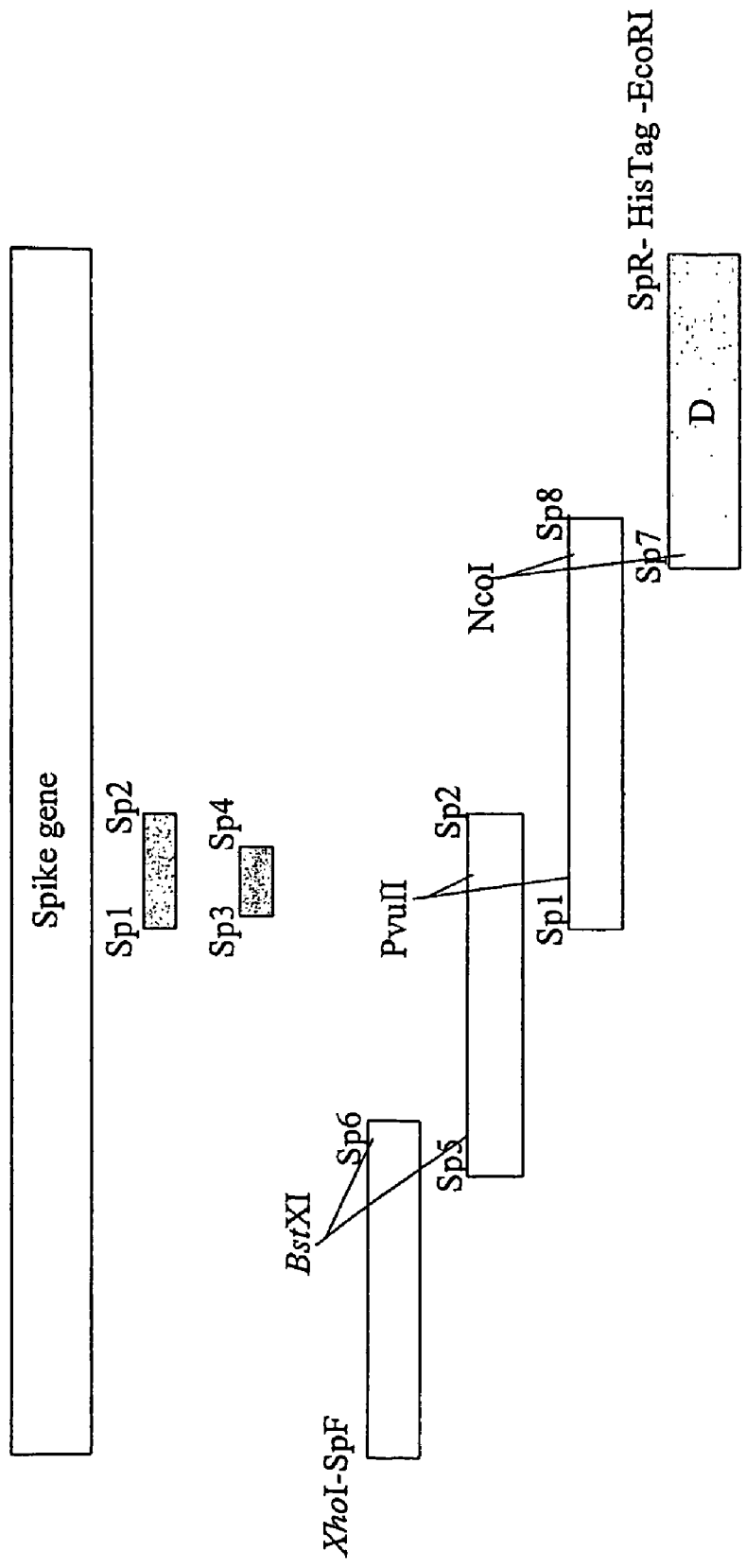

The CRCV Spike gene was cloned using the primers listed in Table 5 and using the following cloning strategy, which is illustrated in FIG. 18.
1. The spike gene was amplified in four overlapping fragments (A,B,C,D).
2. The PCR product Sp5-Sp2 (B) was joined to the product Sp1-Sp8 (C) using the PvuII site in the overlap.
3. This fragment was cloned into the pT7blue2 vector (Novagen) using the restriction sites NcoI and BstXI.
4. The PCR fragment SpFXho-Sp6 (A) was joined to BC using the restriction site BstXI in the overlap and the XhoI site that had been incorporated into the primer SpF-Xho.
5. Fragment ABC was moved into the baculovirus transfer vector pMelBacB (Invitrogen) using the restriction sites XhoI and NcoI.
6. The PCR fragment Sp7-SpR-HisTag-Eco (D) was joined to ABC using the restriction site NcoI in the overlap and the EcoRI site that had been incorporated into the primer SpR-Eco-HisTag resulting in the complete spike gene in pMelBacB (Spike MelBac). This construct contains a HisTag (6xHis) at the C terminus of the expressed protein.
7. For mammalian expression the complete gene was moved to pSecTagA (Invitrogen) using the BamHI site in pMelBacB and the EcoRI site at the end of ABCD resulting in the plasmid SpikeSecTag.

Construction of a Recombinant Baculovirus

A co-transfection was performed in Sf9 cells using the Bac-N-Blue baculovirus DNA (Invitrogen) and Spike MelBac. The resulting baculovirus (AcSpCRCV 1-11) was shown to contain a full-length insert by PCR using primers (Invitrogen) located upstream and downstream of the recombination site.

Expression in Mammalian Cells

The plasmid Spike SecTag was transfected into BHK-21 cells using Lipofectamine (Invitrogen). Expression of the Spike protein was analysed using a serum sample from a dog that had been shown to be positive for antibodies to CRCV using ELISA (BCV antigen obtained from Churchill) and a positive control serum for BCV obtained from Churchill (chicken anti BCV). The transfected cells showed a positive signal in an immunofluorescence assay using the canine or the chicken serum and a FITC labelled conjugate (FITC anti-dog IgG or FITC anti Chicken IgG).

TABLE 5

Primers designed from an alignment of the spike genes of bovine coronavirus (GenBank accession No. AF058942) and human coronavirus, OC43 (GenBank accession No. L14643)

| Name | Sequence | SEQ ID NO: | Location in BCV spike gene |
|---|---|---|---|
| Sp 1 | 5'-CTT-ATA-AGT-GCC-CCC-AAA-CTA-AAT | 40 | 1637-1660 |
| Sp 2 | 5'-CCT-ACT-GTG-AGA-TCA-CAT-GTT-TG | 41 | 2258-2236 |
| Sp 3 | 5'-GTT-GGC-ATA-GGT-GAG-CAC-TG | 42 | 1666-1686 |
| Sp 4 | 5'-GCA-ATG-CTG-GTT-CGG-AAG-AG | 43 | 2107-2088 |
| Sp 5 | 5'-AAC-GGT-TAC-ACT-GTT-CAG-CC | 44 | 931-950 |
| Sp 6 | 5'-CAA-GTA-AAT-GAG-TCT-GCC-TG | 45 | 1121-1102 |
| Sp 7 | 5'-GGC-TGC-CAC-CTC-TGC-TAG-TC | 46 | 2919-2938 |
| Sp 8 | 5'-ATT-GTT-AAA-TGC-ATT-AGC-AAT-AAG-C | 47 | 3069-3045 |
| SpF | 5'-TTT-TTG-ATA-CTT-TTA-ATT-TCC-TTA-CC | 48 | 4-29 |
| SpR | 5'-GTC-GTC-ATG-TGA-WGT-TTT-RAT-TAC | 49 | 4089-4066 |
| SpF-XhoI | 5'-AGC-TCG-AGC-TTT-TTG-ATA-CTT-TTA-ATT-TCC-TTA-CC | 50 | |
| SpR His-EcoRI | 5'-TTG-AAT-TCT-<u>TAA</u>-<u>TGA-TGA-TGA-TGA-TGA-TGG</u>-TCG-TCA-TGT-GAW-GTT-TTR-ATT-AC | 51 | |

SpF-XhoI contains a XhoI site (bold). SpR-His-EcoRI contains a 6xHisTag (double-underlined), a stop codon (underlined) and an EcoRI site (bold)

The invention claimed is:

1. An immunogenic composition for raising an immune response against a coronavirus in a dog, the composition comprising:
   a coronavirus having a Spike (S) protein with at least 97% amino acid identity to SEQ ID NO: 4, or a coronavirus S protein having at least 97% amino acid identity with SEQ ID NO: 4; and
   a pharmaceutically acceptable carrier or adjuvant.

2. An immunogenic composition according to claim 1 wherein the coronavirus S protein is a Canine Respiratory Coronavirus (CRCV) protein.

3. An immunogenic composition according to claim 1 wherein the S protein comprises at least one of the Canine Respiratory Coronavirus (CRCV)-specific amino acids of SEQ ID NO: 4 selected from the group consisting of 103V, 118V, 166D, 171M, 179K, 192P, 210S, 235H, 267F, 388F, 407M, 436S, 440I, 447I, 501F, 525Y, 528N, 540L, 582K, 608G, 692G, 695S, 757W, 758G, 763Q, 769T, 786P, 792H, 818R, 827P, 828V, 887F, 933D, 977F, 1011T, 1018S, 1063K, 1256L, and 1257M.

4. An immunogenic composition according to claim 1 wherein the coronavirus is Canine Respiratory Coronavirus (CRCV).

5. An immunogenic composition according to claim 1 further comprising any one or more of:
   (a) an agent capable of raising an immune response in a dog against canine parainfluenza virus (CPIV);
   (b) an agent capable of raising an immune response in a dog against canine adenovirus type 2(CAV-2);
   (c) an agent capable of raising an immune response in a dog against canine herpesvirus (CHV); and
   (d) an agent capable of raising an immune response in a dog against *Bordetella bronchiseptica* (*B. bronchiseptica*).

6. A method of raising an immune response against a coronavirus in a dog, the method comprising administering to the dog an immunogenic composition according to claim 1.

7. The immunogenic composition according to claim 1, wherein said coronavirus is inactivated.

8. The immunogenic composition according to claim 1, wherein said coronavirus is attenuated.

9. The immunogenic composition according to claim 4, wherein said coronavirus is inactivated.

10. The immunogenic composition according to claim 4, wherein said coronavirus is attenuated.

* * * * *

SEQUENCE LISTING

<160> NUMBER OF SEQ ID NOS: 52

<210> SEQ ID NO 1
<211> LENGTH: 250
<212> TYPE: DNA
<213> ORGANISM: canine respiratory coronavirus

<400> SEQUENCE: 1
ctcagatgaa tttgaaatat gctattagtg ctaagaatag agcccgcact gttgctggtg 60
tttccatact tagtactatg actggcagaa tgtttcatca aaaatgtttg aaaagtatag 120
cagctacacg tggtgttcct gttgttatag gcaccactaa attttatggc ggctgggatg 180
atatgttacg tcgccttatt aaagatgttg acaatcctgt acttatgggt tgggattatc 240
ctaagtgtga 250

<210> SEQ ID NO 2
<211> LENGTH: 83
<212> TYPE: PRT
<213> ORGANISM: canine respiratory coronavirus

<400> SEQUENCE: 2

Gln Met Asn Leu Lys Tyr Ala Ile Ser Ala Lys Asn Arg Ala Arg Thr
1 5 10 15

Val Ala Gly Val Ser Ile Leu Ser Thr Met Thr Gly Arg Met Phe His
20 25 30

Gln Lys Cys Leu Lys Ser Ile Ala Ala Thr Arg Gly Val Pro Val Val
35 40 45

Ile Gly Thr Thr Lys Phe Tyr Gly Gly Trp Asp Asp Met Leu Arg Arg
50 55 60

Leu Ile Lys Asp Val Glu Asn Pro Val Leu Met Gly Trp Asp Tyr Pro
65 70 75 80

Lys Cys Glu

<210> SEQ ID NO 3
<211> LENGTH: 4092
<212> TYPE: DNA
<213> ORGANISM: canine respiratory coronavirus

<400> SEQUENCE: 3
atgtttttga tacttttaat ttccttacca atggcttttg ctgttatagg agatttaaag 60
tgtactacgg tttccatcaa tgatgttgac accggtgctc cttctattag cactgatgtt 120
gtcgatgtta ctaatggttt aggtacttat tatgttttag atcgtgtgta tttaaatact 180
acattgttgc ttaatggtta ttatcctact tcaggttcta catatcgtaa tatggcactg 240
aagggaactt tactattgag cacactatgg tttaaaccac catttctttc tgattttatt 300
gatggtgttt ttgctaaggt aaaaaatacc aaggttatta aagatggtgt agtgtatagt 360
gagtttcctg ctataactat aggtagtact tttgtaaata catcctatag tgtggtagta 420
caaccacata ctactaattt agataataaa ttacaaggtc tcttagagat ctctgtttgc 480
cagtatacta tgtgcgatta cccacatacg atgtgtcatc ctaatctggg taataaacgc 540
atagaactat ggcattggga tacaggtgtt gttccctgtt tatataagcg taatttcaca 600
tatgatgtga atgctgatta tttgtattcc catttttatc aagaaggtgg tactttttat 660
gcatatttta cagacactgg tgttgttact aagtttctgt ttcatgttta tttaggcacg 720

```
gtgctttcac attattatgt catgcccttg acttgtaata gtgctatgac tttagaatac    780
tgggttacac ctctcacttt taaacaatat ttactcgctt tcaatcaaga tggtgttatt    840
tttaatgctg ttgattgtaa gagtgatttt atgagtgaga ttaagtgtaa aacactatct    900
atagcaccat ctactggtgt ttatgaatta acggttaca ctgttcagcc aattgcagat     960
gtttaccgac gtatacctaa tcttcccgat tgtaatatag aggcttggct taatgataag   1020
tcggtgcctt ctccattaaa ttgggaacgt aagacctttt caaattgtaa ttttaatatg   1080
agcagcctga tgtctttat ccaggctgac tcgtttactt gtaataatat tgatgctgct    1140
aagatatacg gtatgtgttt tttcagcata actatagata agtttgctat acccaatggt   1200
aggaaggttg acctacaaat gggcaatttg gctatttgc agtcttttaa ctatagaatt    1260
gatactactg ctacaagttg tcagttgtat tataatttac ctgctagtaa tgtttctatt   1320
agcaggttta atccttctat ttggaatagg agatttggtt ttacagaaca atctgttttt   1380
aagcctcaac ctgtaggtgt ttttactgat catgatgttg tttatgcaca acattgtttt   1440
aaagctccca caaatttctg tccgtgtaaa ttgaatgggt cttttgtgtgt aggtagtggt   1500
tttggtatag atgctggtta aaaaatagt ggtataggca cttgtcctgc aggtactaat    1560
tatttaactt gttataatgc taaccaatgt gattgtttgt gcactccaga ccctatttta   1620
tctaaatcta cagggcctta aagtgcccc caaactaaat acttagttgg cataggtgag    1680
cactgttctg gtcttgctat taaaagtgat tattgtggag gcaatccttg tacttgccaa   1740
ccaaaagcat ttttggggttg gtctgtggac tcttgtttac aagggggatag gtgtaatatt   1800
tttgctaatt ttatttttgca tggtgttaat agtggtacta cttgttctac tgatttacaa   1860
aaatcaaaca cagacataat tcttggtgtt tgtgttaatt atgatcttta tggtattaca   1920
ggccaaggta ttttgttga ggttaatgcg acttattata atagttggca gaacctttta    1980
tatgattcta atggtaatct ctatggtttt agggactact taacaaacag aacttttatg   2040
attcgtagtt gctatagcgg tcgtgtttca gcgggctttc actctaactc ttccgaacca   2100
gcattgctat ttcggaatat taaatgcaat tacgttttta ataatactct ttcacgacag   2160
ctgcaaccta ttaactattt tgatagttat cttggttgtg ttgtcaatgc tgataatagt   2220
acttctagtt ctgttcaaac atgtgatctc acagtaggta gtggtactg ggggattac     2280
tctacacaaa gacgaagtcg tagaacgatt accactggtt atcggtttac taattttgag   2340
ccatttactg ttaatccagt aaatgatagt ttacaccctg taggtggttt gtatgaaatt   2400
caaataccct tcagagttac tataggtaat atggaggagt ttattcaaac aagatctcct   2460
aaagttacta ttgattgtcc tgtttttgtc tgtggtgatt atgcagcatg taaatcacag   2520
ttggttgaat atggtagttt ttgtgacaat attaatgcta tactcacaga agtaaatgaa   2580
ctacttgaca ctacacagtt gcaagtagct aatagtttaa tgaatggtgt cactcttagc   2640
actaagctta aagatggctt taatttcaat gtagatgaca tcaattttc ccctgtatta    2700
ggttgtttag gaagcgaatg taataaagtt tccagtagat ctgctataga ggatttactt   2760
ttttctaaag taaagttatc tgatgttggt tttgttgatg cttataataa ttgtactgga   2820
ggtgccgaaa ttagggacct catttgtgtg caaagttata atggtatcaa agtgttgcct   2880
ccactgctct cagaaaatca gatcagtgga tacacttgg ctgccacctt tgctagtctg   2940
ttcctccctt ggtcagcagc agcaggcgta ccatttatt taaatgttca gtatcgtatt   3000
aatggtattg tgttaccat ggatgtgcta actcaaaatc aaaagctat ttctaatgca     3060
tttaacaatg cccttgatgc tattcaggaa gggtttgatg ctaccaattc tgctttagtt   3120
```

```
aaaattcaag ctgttgttaa tgcaaatgct gaagctctta ataacttatt gcaacaactc    3180
tctaataaat ttggtgctat aagtgcttct ttacaagaaa ttctatctag acttgatgct    3240
cttgaagcgc aagctcagat agacagactt atcaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420 aatcatatta tatcattagt gcagaatgct ccatatggtt tgtattttat ccactttagc    3480
tatgtcccta ctaagtatgt cactgcgaag gttagtcccg gtctgtgcat ygcaggtgat    3540
agaggtatag ctcctaagag tggttatttt gttaatgtaa ataacacttg gatgttcact    3600
ggtagtggtt attactaccc tgaacctata actggaaata atgtggttgt tatgagtacc    3660
tgtgctgtta actatactaa agcaccggat gtaatgctga acatttcaac acccaacctc    3720
cctgatttta aggaagagtt ggatcaatgg tttaaaaacc aaacattaat ggcaccagat    3780
ttgtcacttg attatataaa tgttacattc ttggacctac aagatgaaat gaataggtta    3840
caggaggcaa taaagttttt aaatcatagc tacatcaatc tcaaggacat tggtacatat    3900
gaatattatg taaaatggcc ttggtatgta tggcttttaa ttggccttgc tggcgtagct    3960
atgcttgttt tactattctt catatgctgt tgtacaggat gtgggactag ttgttttaag    4020
aaatgcggtg gttgttgtga tgattatact ggacatcagg agttagtaat caaaacgtca    4080
catgacgact aa                                                         4092

<210> SEQ ID NO 4
<211> LENGTH: 1363
<212> TYPE: PRT
<213> ORGANISM: canine respiratory coronavirus

<400> SEQUENCE: 4

Met Phe Leu Ile Leu Leu Ile Ser Leu Pro Met Ala Phe Ala Val Ile
1               5                   10                  15

Gly Asp Leu Lys Cys Thr Thr Val Ser Ile Asn Asp Val Asp Thr Gly
            20                  25                  30

Ala Pro Ser Ile Ser Thr Asp Val Val Asp Val Thr Asn Gly Leu Gly
        35                  40                  45

Thr Tyr Tyr Val Leu Asp Arg Val Tyr Leu Asn Thr Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Thr Leu Trp Phe Lys Pro Pro Phe Leu
                85                  90                  95

Ser Asp Phe Ile Asp Gly Val Phe Ala Lys Val Lys Asn Thr Lys Val
            100                 105                 110

Ile Lys Asp Gly Val Val Tyr Ser Glu Phe Pro Ala Ile Thr Ile Gly
        115                 120                 125

Ser Thr Phe Val Asn Thr Ser Tyr Ser Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Asp Tyr Pro His Thr Met Cys His Pro Asn Leu
                165                 170                 175

Gly Asn Lys Arg Ile Glu Leu Trp His Trp Asp Thr Gly Val Val Pro
            180                 185                 190
```

-continued

```
Cys Leu Tyr Lys Arg Asn Phe Thr Tyr Asp Val Asn Ala Asp Tyr Leu
    195                 200                 205

Tyr Ser His Phe Tyr Gln Glu Gly Gly Thr Phe Tyr Ala Tyr Phe Thr
    210                 215                 220

Asp Thr Gly Val Val Thr Lys Phe Leu Phe His Val Tyr Leu Gly Thr
225                 230                 235                 240

Val Leu Ser His Tyr Tyr Val Met Pro Leu Thr Cys Asn Ser Ala Met
                245                 250                 255

Thr Leu Glu Tyr Trp Val Thr Pro Leu Thr Phe Lys Gln Tyr Leu Leu
        260                 265                 270

Ala Phe Asn Gln Asp Gly Val Ile Phe Asn Ala Val Asp Cys Lys Ser
            275                 280                 285

Asp Phe Met Ser Glu Ile Lys Cys Lys Thr Leu Ser Ile Ala Pro Ser
        290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
    370                 375                 380

Met Cys Phe Phe Ser Ile Thr Ile Asp Lys Phe Ala Ile Pro Asn Gly
385                 390                 395                 400

Arg Lys Val Asp Leu Gln Met Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
            420                 425                 430

Leu Pro Ala Ser Asn Val Ser Ile Ser Arg Phe Asn Pro Ser Ile Trp
        435                 440                 445

Asn Arg Arg Phe Gly Phe Thr Glu Gln Ser Val Phe Lys Pro Gln Pro
    450                 455                 460

Val Gly Val Phe Thr Asp His Asp Val Val Tyr Ala Gln His Cys Phe
465                 470                 475                 480

Lys Ala Pro Thr Asn Phe Cys Pro Cys Lys Leu Asn Gly Ser Leu Cys
                485                 490                 495

Val Gly Ser Gly Phe Gly Ile Asp Ala Gly Tyr Lys Asn Ser Gly Ile
            500                 505                 510

Gly Thr Cys Pro Ala Gly Thr Asn Tyr Leu Thr Cys Tyr Asn Ala Asn
        515                 520                 525

Gln Cys Asp Cys Leu Cys Thr Pro Asp Pro Ile Leu Ser Lys Ser Thr
    530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Lys Ala Phe Leu Gly Trp Ser Val Asp Ser Cys
            580                 585                 590

Leu Gln Gly Asp Arg Cys Asn Ile Phe Ala Asn Phe Ile Leu His Gly
        595                 600                 605
```

```
Val Asn Ser Gly Thr Thr Cys Ser Thr Asp Leu Gln Lys Ser Asn Thr
    610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
        675                 680                 685

Val Ser Ala Gly Phe His Ser Asn Ser Ser Glu Pro Ala Leu Leu Phe
    690                 695                 700

Arg Asn Ile Lys Cys Asn Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Val Gln Thr Cys Asp Leu Thr Val
            740                 745                 750

Gly Ser Gly Tyr Trp Gly Asp Tyr Ser Thr Gln Arg Arg Ser Arg Arg
    755                 760                 765

Thr Ile Thr Thr Gly Tyr Arg Phe Thr Asn Phe Glu Pro Phe Thr Val
770                 775                 780

Asn Pro Val Asn Asp Ser Leu His Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Thr Arg Ser Pro Lys Val Thr Ile Asp Cys Pro Val Phe Val Cys Gly
            820                 825                 830

Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
    850                 855                 860

Thr Gln Leu Gln Val Ala Asn Ser Leu Met Asn Gly Val Thr Leu Ser
865                 870                 875                 880

Thr Lys Leu Lys Asp Gly Phe Asn Phe Asn Val Asp Asp Ile Asn Phe
                885                 890                 895

Ser Pro Val Leu Gly Cys Leu Gly Ser Glu Cys Asn Lys Val Ser Ser
            900                 905                 910

Arg Ser Ala Ile Glu Asp Leu Leu Phe Ser Lys Val Lys Leu Ser Asp
        915                 920                 925

Val Gly Phe Val Asp Ala Tyr Asn Asn Cys Thr Gly Gly Ala Glu Ile
    930                 935                 940

Arg Asp Leu Ile Cys Val Gln Ser Tyr Asn Gly Ile Lys Val Leu Pro
945                 950                 955                 960

Pro Leu Leu Ser Glu Asn Gln Ile Ser Gly Tyr Thr Leu Ala Ala Thr
                965                 970                 975

Phe Ala Ser Leu Phe Pro Pro Trp Ser Ala Ala Gly Val Pro Phe
            980                 985                 990

Tyr Leu Asn Val Gln Tyr Arg Ile Asn Gly Ile Gly Val Thr Met Asp
        995                 1000                1005

Val Leu Thr Gln Asn Gln Lys Leu Ile Ser Asn Ala Phe Asn Asn
    1010                1015                1020
```

Ala Leu Asp Ala Ile Gln Glu Gly Phe Asp Ala Thr Asn Ser Ala
1025                1030                1035

Leu Val Lys Ile Gln Ala Val Val Asn Ala Asn Ala Glu Ala Leu
1040                1045                1050

Asn Asn Leu Leu Gln Gln Leu Ser Asn Lys Phe Gly Ala Ile Ser
1055                1060                1065

Ala Ser Leu Gln Glu Ile Leu Ser Arg Leu Asp Ala Leu Glu Ala
1070                1075                1080

Gln Ala Gln Ile Asp Arg Leu Ile Asn Gly Arg Leu Thr Ala Leu
1085                1090                1095

Asn Ala Tyr Val Ser Gln Gln Leu Ser Asp Ser Thr Leu Val Lys
1100                1105                1110

Phe Ser Ala Ala Gln Ala Met Glu Lys Val Asn Glu Cys Val Lys
1115                1120                1125

Ser Gln Ser Ser Arg Ile Asn Phe Cys Gly Asn Gly Asn His Ile
1130                1135                1140

Ile Ser Leu Val Gln Asn Ala Pro Tyr Gly Leu Tyr Phe Ile His
1145                1150                1155

Phe Ser Tyr Val Pro Thr Lys Tyr Val Thr Ala Lys Val Ser Pro
1160                1165                1170

Gly Leu Cys Ile Ala Gly Asp Arg Gly Ile Ala Pro Lys Ser Gly
1175                1180                1185

Tyr Phe Val Asn Val Asn Asn Thr Trp Met Phe Thr Gly Ser Gly
1190                1195                1200

Tyr Tyr Tyr Pro Glu Pro Ile Thr Gly Asn Asn Val Val Val Met
1205                1210                1215

Ser Thr Cys Ala Val Asn Tyr Thr Lys Ala Pro Asp Val Met Leu
1220                1225                1230

Asn Ile Ser Thr Pro Asn Leu Pro Asp Phe Lys Glu Glu Leu Asp
1235                1240                1245

Gln Trp Phe Lys Asn Gln Thr Leu Met Ala Pro Asp Leu Ser Leu
1250                1255                1260

Asp Tyr Ile Asn Val Thr Phe Leu Asp Leu Gln Asp Glu Met Asn
1265                1270                1275

Arg Leu Gln Glu Ala Ile Lys Val Leu Asn His Ser Tyr Ile Asn
1280                1285                1290

Leu Lys Asp Ile Gly Thr Tyr Glu Tyr Tyr Val Lys Trp Pro Trp
1295                1300                1305

Tyr Val Trp Leu Leu Ile Gly Leu Ala Gly Val Ala Met Leu Val
1310                1315                1320

Leu Leu Phe Phe Ile Cys Cys Cys Thr Gly Cys Gly Thr Ser Cys
1325                1330                1335

Phe Lys Lys Cys Gly Gly Cys Cys Asp Asp Tyr Thr Gly His Gln
1340                1345                1350

Glu Leu Val Ile Lys Thr Ser His Asp Asp
1355                1360

<210> SEQ ID NO 5
<211> LENGTH: 250
<212> TYPE: DNA
<213> ORGANISM: bovine coronavirus strain LY138

-continued

```
<400> SEQUENCE: 5
ctcaaatgaa tttgaaatat gctattagtg ctaagaatag agcccgcact gttgctggtg      60
tttccatact cagtactatg actggcagaa tgtttcatca aaaatgtttg aaaagtatag     120
cagctacacg tggtgttcct gttgttatag gcaccactaa gttttatggc ggctgggatg     180
atatgttacg tcgccttatt aaagatgttg ataatcctgt acttatgggt tgggattatc     240
ctaagtgtga                                                            250

<210> SEQ ID NO 6
<211> LENGTH: 250
<212> TYPE: DNA
<213> ORGANISM: human coronavirus strain OC43

<400> SEQUENCE: 6
ctcaaatgaa tttgaaatat gctattagtg ctaagaatag agcccgcact gttgctggtg      60
tttccatact tagtactatg actggcagaa tgtttcatca aaaatgtttg aaaagtatag     120
cagctacacg tggtgttcct gtagttatag gcaccactaa attttatggt ggctgggatg     180
atatgttacg ccgccttatt aaagatgttg acaatcctgt acttatgggt tgggattatc     240
ctaagtgtga                                                            250

<210> SEQ ID NO 7
<211> LENGTH: 250
<212> TYPE: DNA
<213> ORGANISM: hemagglutinating encephalomyelitis virus

<400> SEQUENCE: 7
ctcaaatgaa tttgaaatat gctattagtg ccaagaatag agcccgcact gttgctggtg      60
tttccatact tagtactatg actggcagaa tgtttcatca aaaatgcttg aaaagtatag     120
cagctacacg tggcgttcct gtggttatag gcaccactaa attttatggc ggctgggatg     180
atatgttacg ccgccttatt aaagatgttg ataatcctgt acttatgggt tgggattatc     240
caaagtgtga                                                            250

<210> SEQ ID NO 8
<211> LENGTH: 250
<212> TYPE: DNA
<213> ORGANISM: canine enteric coronavirus

<400> SEQUENCE: 8
ctcagatgaa tttgaaatat gctatttctg gaaaggctag agctcgtaca gtaggaggag      60
tttcacttct ttctaccatg actacgagac aataccacca gaagcatttg aagtcaattg     120
ctgcaacacg caatgccact gtggttattg gctcaaccaa gttttatggt ggttgggata     180
acatgcttaa aaatttaatg cgtgatgttg ataatggttg tttgatggga tgggactatc     240
ctaagtgtga                                                            250

<210> SEQ ID NO 9
<211> LENGTH: 81
<212> TYPE: PRT
<213> ORGANISM: human coronavirus strain OC43

<400> SEQUENCE: 9

Met Asn Leu Lys Tyr Ala Ile Ser Ala Lys Asn Arg Ala Arg Thr Val
 1               5                  10                  15

Ala Gly Val Ser Ile Leu Ser Thr Met Thr Gly Arg Met Phe His Gln
             20                  25                  30
```

```
Lys Cys Leu Lys Ser Ile Ala Ala Thr Arg Gly Val Pro Val Ile
        35                  40                  45

Gly Thr Thr Lys Phe Tyr Gly Gly Trp Asp Asp Met Leu Arg Arg Leu
    50                  55                  60

Ile Lys Asp Val Asp Asn Pro Val Leu Met Gly Trp Asp Tyr Pro Lys
65                  70                  75                  80

Cys

<210> SEQ ID NO 10
<211> LENGTH: 81
<212> TYPE: PRT
<213> ORGANISM: hemagglutinating encephalomyelitis virus

<400> SEQUENCE: 10

Met Asn Leu Lys Tyr Ala Ile Ser Ala Lys Asn Arg Ala Arg Thr Val
1               5                   10                  15

Ala Gly Val Ser Ile Leu Ser Thr Met Thr Gly Arg Met Phe His Gln
            20                  25                  30

Lys Cys Leu Lys Ser Ile Ala Ala Thr Arg Gly Val Pro Val Val Ile
        35                  40                  45

Gly Thr Thr Lys Phe Tyr Gly Gly Trp Asp Asp Met Leu Arg Arg Leu
    50                  55                  60

Ile Lys Asp Val Asp Asn Pro Val Leu Met Gly Trp Asp Tyr Pro Lys
65                  70                  75                  80

Cys

<210> SEQ ID NO 11
<211> LENGTH: 81
<212> TYPE: PRT
<213> ORGANISM: bovine coronavirus strain LY138

<400> SEQUENCE: 11

Met Asn Leu Lys Tyr Ala Ile Ser Ala Lys Asn Arg Ala Arg Thr Val
1               5                   10                  15

Ala Gly Val Ser Ile Leu Ser Thr Met Thr Gly Arg Met Phe His Gln
            20                  25                  30

Lys Cys Leu Lys Ser Ile Ala Ala Thr Arg Gly Val Pro Val Val Ile
        35                  40                  45

Gly Thr Thr Lys Phe Tyr Gly Gly Trp Asp Asp Met Leu Arg Arg Leu
    50                  55                  60

Ile Lys Asp Val Asp Asn Pro Val Leu Met Gly Trp Asp Tyr Pro Lys
65                  70                  75                  80

Cys

<210> SEQ ID NO 12
<211> LENGTH: 84
<212> TYPE: PRT
<213> ORGANISM: canine enteric coronavirus

<400> SEQUENCE: 12

Met Thr Gln Met Asn Leu Lys Tyr Ala Ile Ser Gly Lys Ala Arg Ala
1               5                   10                  15

Arg Thr Val Gly Gly Val Ser Leu Leu Ser Thr Met Thr Thr Arg Gln
            20                  25                  30

Tyr His Gln Lys His Leu Lys Ser Ile Ala Ala Thr Arg Asn Ala Thr
        35                  40                  45
```

```
Val Val Ile Gly Ser Thr Lys Phe Tyr Gly Gly Trp Asp Asn Met Leu
 50                  55                  60

Lys Asn Leu Met Arg Asp Val Asp Asn Gly Cys Leu Met Gly Trp Asp
 65                  70                  75                  80

Tyr Pro Lys Cys

<210> SEQ ID NO 13
<211> LENGTH: 4363
<212> TYPE: DNA
<213> ORGANISM: canine enteric coronavirus

<400> SEQUENCE: 13
atgattgtgc tcgtaacttg cattttattg ttatgttcat accacactgc ttcgagtacg      60
tcaaataatg attgtagaca agttaacgta acacaattag atggcaatga aaacctcatt     120
agagactttt tgtttcaaaa ctttaaagaa gaggaactg tagttgttgg tggttactac      180
cctacagagg tttggtataa ctgttctaga acagcaacaa ctactgccta tgagtatttc     240
agtaatatac acgcattcta ttttgatatg gaagccatgg agaatagtac tggtaatgca     300
cgtggtaaac ctttattatt tcatgttcat ggtgagcctg ttagtgtcat catatacata     360
tcttatagag atgatgtgca acataggcca cttttaaaac acggattagt gtgcataact     420
gaaagtcgca acattgacta taacagtttc accagtagcc agtggaattc catatgtacg     480
ggtaatgaca gaaaaattcc tttctctgtc atacccacgg acaatggaac aaaaatttat     540
ggtcttgagt ggaatgatga atttgttaca gcgtacatta gtggtcgttc ttataattgg     600
aacatcaata taattggtt taacaatgtc acgcttctgt atagtcgctc aagcactgcc     660
acatggcaac acagtgctgc atacgtttac caaggtgttt ctaacttcac ttattacaag     720
ttaaataaca ccaatggtct aaaaacctat gaattatgtg aagattatga atattgcact     780
ggctacgcca ctaacatctt tgccccaact gtgggaggtt acatacctga tggatttagt     840
tttaacaatt ggtttttgct tacaaacagc tccacttttg ttagtggcag atttgtaaca     900
aatcaaccat tattagttaa ttgcttgtgg ccagttccta gttttggtgt tgcagcacaa     960 gaatttgtt ttgaaggtgc acagtttagc aatgtaatg gtgtgttttt aaataacaca    1020
gtagatgtca ttagattcaa ccttaatttt actgcagatg tacaatctgg catgggtgct    1080
acagtatttt cactgaatac aacaggtggt tgcattcttg agatttcttg ttataatgat    1140
atagtgagcg agtcaagttt ctacagttat ggtgaaattc ccttcggcgt aactgatgga    1200
ccgcgttatt gttatgtcct ctataatggc acagctctta gtatttcgg cacattaccc    1260 cctagtgtca aggaaattgc tattagtaag tggggccaat tttatattaa tggttacaat    1320
ttctttagca cttttcctat tgattgtata tcttttaact taaccactgg tgatagtgga    1380
gcattttgga caattgctta cacatcgtac actgaagcat tagtacaagt tgaaaacaca    1440
gccattaaaa aggtgacgta ttgtaacagt cacattaata catcaaatg ttctcaactt    1500 actgctaatt tgcaaaatgg ctttatcct gttgcttcaa gtgaagttgg tcttgtcaat    1560
aagagtgttg tgttactacc tagtttctat tcacatacca gtgttaatat aactattgat    1620
cttggtatga agcgtagtgg ttatggtcaa cccatagcct caacactaag taacatcaca    1680
ctaccaatgc aggataataa caccgatgtg tactgtattc gttctaacca attctcagtt    1740
tatgttcact ccacttgcaa aagttcttta tgggacaaca attttaatca agattgcaca    1800 gatgtttat atgccacagc tgttataaaa actggtactt gccccttctc atttgataaa    1860
ttgaataatt acttaacttt taacaagctt tgtttgtcgt tgaatcctac tggtgccaac    1920
```

```
tgtaagtttg atgttgctgc ccgtacaaga accaatgagc aggttgttag aagtttatat    1980
gtaatatatg aagaaggaga caacatagtg ggtgtaccgt ctgataatag tggtcttcac    2040
gatttgtcag tgttacactt agactcctgt acagattaca atatatatgg tagaactggt    2100
gttggtatta ttagacaaac taacagcaca atacttagtg gcttacatta tacatcacta    2160
tcaggtgatt tattaggttt taaaaatgtt agtgatggtg ttgtctattc tgtgacacca    2220
tgtgatgtaa gcgcacaagc ggctgttatt gatggggcca tagttggagc tatgacttcc    2280
attaatagtg aactgttagg tctaacacat tggacaacaa caccaaattt ttattactac    2340
tctatatata atacaacaaa tgagagaact cgtggcactg caatcgacag taacgatgta    2400
gattgtgaac ctatcataac ctattctaac ataggtgttt gtaaaaatgg tgcgttggtt    2460
tttattaacg tcacacattc tgatggagat gttcaaccaa ttagcactgg caatgtcacg    2520
atacccacaa actttaccat atctgtgcaa gttgaataca tccaggttta cactacaccg    2580 gtgtcaaatag attgttctag atacgtttgt aatggtaacc ctagatgtaa taaattgtta    2640
acacaatatg tttctgcatg tcaaactatt gagcaagcgc ttgcaatgag tgccagcctt    2700
gaaaacatgg aagttgattc catgttgttt gtttcagaaa atgcccttaa attggcatct    2760
gttgaggcgt tcaatagtac agaacattta gatcctattt acaaagaatg gcctaacata    2820
ggtggttctt ggctaggagg tctaaaagac atacttccgt cccataatag caaacgtaag    2880
tatcgttctg ctatagaaga cttgcttttt gataaagttg taacttctgg tctaggtaca    2940
gttgatgaag attataaacg ttgtacaggt ggttatgaca tagctgactt agtttgtgca    3000
caatattaca atggcatcat ggttctacct ggtgttgcta atgatgacaa gatgactatg    3060
tacacagcct ctcttgcagg tggtataagca ttaggtgcac taggtggtgg cgccgtggct    3120
ataccttttg cagtagcagt tcaggctaga cttaattatg ttgctctaca aactgatgta    3180
ttgaacaaaa accagcagat cctggctaat gctttcaacc aagctattgg taacattaca    3240
caggcatttg gtaaggttaa tgatgctata catcaaacat cacaaggtct tgccactgtt    3300
gctaaagcat tggcaaaagt gcaagatgtt gttaacacac aagggcaagc tttaagccac    3360
ctaacagtac aactgcaaaa tagcttccaa gccattagta gttctattag tgacatttat    3420
aataggcttg atgaactgag tgctgatgca caagttgata ggctgattac aggtagactt    3480
acagcactta atgcatttgt atctcagact ctaaccagac aagcggaggt tagggctagt    3540
agacaacttg ccaaagacaa ggttaatgaa tgtgttaggt ctcagtctca gagatttgga    3600
ttttgtggta atggtacaca tttgttttca cttgcaaatg cagcaccaaa tggcatggtt    3660
ttctttcaca cagtgctatt accaacagct tatgaaactg taacagcttg gtcaggtatt    3720
tgtgcttcag atggcgatcg cacttttgga cttgtcgtta aagatgttca gttgacgttg    3780
tttcgtaatc tagatgacaa gttctatttg actcccagaa ctatgtatca gcctagagct    3840
gcaactagtt ctgattttgt tcagattgag gggtgcgacg tgttgtttgt caatgcaact    3900
gtaattgact tgcctagtat tatacctgac tatatcgaca ttaatcagac tgttcaagac    3960
atattagaaa actacagacc aaactggact gtacctgaat tgacaattga cattttttaac    4020 gcaacctatt taaatctgac tggtgaaatt gatgacttag aatttaggtc agaaaagcta    4080
cataacacca cagtagagct tgccattctc attgacaata ttaacaatac attagtcaat    4140
cttgaatggc tcaatagaat tgaaactttat gtgaaatggc cttggtatgt gtggctacta    4200
ataggcttag tagtagtgtt ttgcataccg ctattgctat tttgctgttg tagtacaggt    4260
```

-continued

| | |
|---|---|
| tgctgtggat gcataggttg tttgggaagt tgttgtcatt ctatttgtag tagaagacaa | 4320 |
| tttgaaaatt acgaaccaat tgaaaagtg catgtccact aaa | 4363 |

<210> SEQ ID NO 14
<211> LENGTH: 4049
<212> TYPE: DNA
<213> ORGANISM: bovine coronavirus strain LY138

<400> SEQUENCE: 14

| | |
|---|---|
| atgtttttga tacttttaat ttccttacca atggctcttg ctgttatagg agatttaaag | 60 |
| tgtactacgg tttccattaa tgatgttgac accggtgttc cttctgttag cactgatact | 120 |
| gtcgatgtta ctaatggttt aggtacttat tatgttttag atcgtgtgta tttaaatact | 180 |
| acgttgttgc ttaatggtta ctaccctact tcaggttcta catatcgtaa tatggcactg | 240 |
| aagggaactt tactattgag cacactatgg tttaaaccac ttttctttc tgattttatt | 300 |
| aatggtattt ttgctaaggt caaaaatacc aaggttatta aaaatggtgt aatgtatagt | 360 |
| gagtttcctg ctataactat aggtagtact tttgtaaata catcctatag tgtggtagta | 420 |
| caaccacata ctaccaattt agataataaa ttacaaggtc tcttagagat ctctgtttgc | 480 |
| cagtatacta tgtgcgagta cccacatacg atttgtcatc ctaatttggg taatcggcgc | 540 |
| atagaactat ggcattggga tacaggtgtt gtttcctgtt tatataagcg taatttcaca | 600 |
| tatgatgtga atgctgatta tttgtatttc cattttatc aagaaggtgg tactttttat | 660 |
| gcatatttta cagacactgg tgttgttact aagtttctgt ttaatgttta tttaggcacg | 720 |
| gtgctttcac attattatgt catgcctttg acttgtaata gtgctatgac tttagaatat | 780 |
| tgggttacac ctctcacttc taaacaatat ttactcgctt tcaatcaaga tggtgttatt | 840 |
| tttaatgctg ttgattgtaa gagtgatttt atgagtgaga ttaagtgtaa aacactatct | 900 |
| atagcaccat ctactggtgt ttatgaatta acggttaca ctgttcagcc aattgcagat | 960 |
| gtttaccgac gtatacctaa tcttcccgat tgtaatatag aggcttggct taatgataag | 1020 |
| tctgtgccct ctccattaaa ttgggaacgt aagaccttt caattgtaa ttttaatatg | 1080 |
| agcagcctga tgtcttttat tcaggcagac tcatttactt gtaataatat tgatgcagct | 1140 |
| aagatatatg gtatgtgttt ttccagcata actatagata gtttgctat acccaatggt | 1200 |
| aggaaggttg acctacaatt gggcaatttg gctatttgc agtcttttaa ctatagaatt | 1260 |
| gatactactg ctacaagttg tcagttgtat tataatttac ctgctgctaa tgtttctgtt | 1320 |
| agcaggttta atccttctac ttggaatagg agatttggtt ttacagaaca atctgttttt | 1380 |
| aagcctcaac ctgtaggtgt ttttactgat catgatgttg tttatgcaca acattgtttt | 1440 |
| aaagctccca caaatttctg tccgtgtaaa ttggatgggt ctttgtgtgt aggtagtggt | 1500 |
| tctggtatag atgctggtta taaaaatagt ggtataggca cttgtcctgc aggtactaat | 1560 |
| tatttaactt gtcataatgc tgcccaatgt aattgtttgt gcactccaga ccccattaca | 1620 |
| tctaaatcta cagggcctta taagtgcccc caaactaaat atttagttgg cataggtgag | 1680 |
| cactgttcgg gtcttgctat taaagtgat tattgtggag gtaatccttg tacttgccaa | 1740 |
| ccacaagcat ttttgggttg gtctgttgat tcttgtttac aagggatag gtgtaatatc | 1800 |
| tttgctaatt ttatttgca tgatgttaat agtggtacta cttgttctac tgatttacaa | 1860 |
| aaatcaaaca cagacataat tcttggtgtt tgtgttaatt atgatcttta tggtattaca | 1920 |
| ggccaaggta ttttgttga ggttaatgcg acttattata atagttggca gaacctttta | 1980 |
| tatgattcta atggtaatct ctatggttt agagactact taacaaacag aactttatg | 2040 |

-continued

```
attcgtagtt gctatagcgg tcgtgtttca gcggcctttc atgctaattc ttccgaacca    2100
gcattgctat ttcggaatat taaatgcaat tacgttttta ataatactct ttcacgacag    2160
ctgcaaccta ttaactattt tgatagttat cttggttgtg ttgtcaatgc tgataatagt    2220
acttctagtg ctgttcaaac atgtgatctc acagtaggta gtggttactg tgtggattac    2280
tctacaaaaa gacgaagtcg tagagcgatt accactggtt atcggtttac taattttgag    2340
ccatttactg ttaattcagt aaatgatagt ttagaacctg taggtggttt gtatgaaatt    2400
caaatacctt cagagtttac tataggtaat atggaggagt ttattcaaat aagctctcct    2460
aaagttacta ttgattgttc tgcttttgtc tgtggtgatt atgcagcatg taaatcacag    2520
ttggttgaat atggtagttt ctgtgacaat attaatgcta tactcacaga agtaaatgaa    2580
ctacttgaca ctacacagtt gcaagtagct aatagtttaa tgaatggtgt cactcttagc    2640
actaagctta agatggcgt taatttcaat gtagacgaca tcaattttc cctgtatta     2700 ggttgtttag gaagcgattg taataaagtt tccagtagat ctgctataga ggatttactt    2760 tttctaaag taaagttatc tgatgtcggt tttgttgagg cttataataa ttgtactgga    2820
ggtgccgaaa ttagggacct catttgtgtg caaagttata atggtatcaa agtgttgcct    2880
ccactactct cagaaaatca gatcagtgga tacactttgg ctgctacctc tgctagtctg    2940
tttcctcctt ggtcagcagc agcaggcgta ccatttatt taaatgttca gtatcgtatt    3000
aatgggattg gtgttaccat ggatgttcta agtcaaaatc aaaagcttat tgctaatgca    3060
tttaacaatg cccttgatgc tattcaggaa gggtttgatg ctaccaattc tgctttagtt    3120
aaaattcaag ctgttgttaa tgcaaatgct gaagctctta ataacttatt gcaacaactc    3180
tctaatagat ttggtgctat aagttcttct ttacaagaaa ttctatctag acttgatgct    3240
cttgaagcgc aagctcagat agacagactt attaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420 aatcatatta tatcattagt gcagaatgct ccatatggtt tgtattttat ccactttagc    3480
tatgtcccta ctaagtatgt cactgcgaag gttagtccg gtctgtgcat tgctggtgat    3540
agaggtatag cccctaagag tggttatttt gttaatgtaa ataacacttg gatgttcact    3600
ggtagtggtt attactaccc tgaacctata actggaaata tgttgttgt tatgagtacc    3660 tgtgctgtta attacactaa agcaccggat gtaatgctga acatttcaac acccaacctc    3720
cctgatttta aggaagagtt ggatcaatgg tttaaaaacc aaacatcagt ggcaccagat    3780
ttgtcacttg attatataaa tgttacattc ttggacctac aagatgaaat gaataggtta    3840
caggaggcaa taaagttttt aaatcagagc tacatcaatc tcaaggacat tggtacatat    3900
gagtattatg taaaatggcc ttggtatgta tggcttttaa ttggccttgc tggtgtagct    3960
atgcttgttt tactattctt catatgctgt tgtacaggat gtgggactag ttgttttaag    4020
aaatgtggtg gttgttgtga tgattatac                                     4049
```

<210> SEQ ID NO 15
<211> LENGTH: 4060
<212> TYPE: DNA
<213> ORGANISM: human coronavirus strain OC43

<400> SEQUENCE: 15

```
atgtttttga tacttttaat ttccttacca acggcttttg ctgttatagg agatttaaag    60
tgtactacgg tttccattaa tgatattgac accggtgctc cttctattag cactgatatt    120
```

```
gtcgatgtta ctaatggttt aggtacttat tatgttttag atcgtgtgta tttaaatact    180
acgttgttgc ttaatggtta ctaccctact tcaggttcta catatcgtaa tatggcactg    240
aagggaactt tactattgag cagactatgg tttaaaccac cttttctttc tgattttatt    300
aatggtattt ttgctaaggt caaaaatacc aaggttatta aaaagggtgt aatgtatagt    360
gagtttcctg ctataactat aggtagtact tttgtaaata catcctatag tgtggtagta    420
caaccacata ctaccaattt ggataataaa ttacaaggtc tcttagagat ctctgtttgc    480
cagtatacta tgtgcgagta cccacatacg atttgtcatc ctaatctggg taatcgacgc    540
gtagaactat ggcattggga tacaggtgtt gtttcctgtt tatataagcg taatttcaca    600
tatgatgtga atgctgatta cttgtatttc catttttatc aagaaggtgg tacttttat    660 gcatatttta cagacactgg tgttgttact aagtttctgt ttaatgttta tttaggcacg    720
gtgctttcac attattatgt cctgcctttg acttgtaata gtgctatgac tttagaatat    780
tgggttacac ctctcacttc taaacaatat ttactagctt tcaatcaaga tggtgttatt    840
tttaatgctg ttgattgtaa gagtgatttt atgagtgaga ttaagtgtaa aacactatct    900
atagcaccat ctactggtgt ttatgaatta acggttaca ctgttcagcc aattgcagat    960
gtttaccgac gtatacctaa tcttcccgat tgtaatatag aggcttggct taatgataag   1020
tcggtgccct ctccattaaa ttgggaacgt aagacctttt caaattgtaa ttttaatatg   1080
agcagcctga tgtcttttat tcaggcagac tcatttactt gtaataatat tgatgctgct   1140
aagatatatg gtatgtgttt ttccagcata actatagata gtttgctat acccaatggt   1200 aggaaggttg acctacaatt gggcaatttg gctatttgc agtcttttaa ctatagaatt   1260
gatactactg ctacaagttg tcagttgtat tataatttac ctgctgctaa tgtttctgtt   1320
agcaggttta atccttctac ttggaatagg agatttggtt ttacagaaca atctgttttt   1380
aagcctcaac ctgtaggtgt ttttactcat catgatgttg tttatgcaca acattgtttt   1440
aaagctccca caaatttctg tccgtgtaaa ttggatgggt ctttgtgtgt aggtaatggt   1500
cctggtatag atgctggtta taaaaatagt ggtataggca cttgtcctgc aggtactaat   1560
tatttaactt gccataatgc tgcccaatgt gattgtttgt gcactcccga ccccattaca   1620
tctaaatcta cagggcctta caagtgcccc caaactaaat acttagttgg cataggtgag   1680
cactgttcgg gtcttgctat taaaagtgat tattgtggag gtaatccttg tacttgccaa   1740
ccacaagcat tttgggttg gtctgttgac tcttgtttac aagggatag gtgtaatatt   1800 tttgctaatt ttatttgca tgatgttaat agtggtacta cttgttctac tgatttacaa   1860
aaatcaaaca cagacataat tcttggtgtt tgtgttaatt atgatcttta tggtattaca   1920
ggccaaggta ttttgttga ggttaatgcg ccttattata tagttggca gaacctttta   1980 tatgattcta atggtaatct ctatggtttt agagactact taacaaacag aactttatg   2040 attcgtagtt gctatagcgg tcgtgtttca gcggcctttc atgctaactc ttccgaacca   2100
gcattgctat ttcggaatat taaatgcagt tacgttttta ataatactct ttcacgacag   2160
ctgcaaccta ttaactattt tgatagttat cttggttgtg ttgtcaatgc tgataatagt   2220
acttctagtg ttgttcaaac atgtgatctc acagtaggta gtggttactg tgtggattac   2280
tctacaaaaa gacgaagtcg tagagcgatt accactggtt atcggtttac taattttgag   2340
ccatttactg ttaattcagt aaatgatagt ttagaacctg taggtggttt gtatgaaatt   2400
caaatacctt cagagtttac tataggtaat atggaggagt ttattcaaac aagctctcct   2460
aaagttacta ttgattgttc tgcttttgtc tgtggtgatt atgcagcatg taaatcacag   2520
```

```
ttggttgaat atggtagctt ctgtgacaat attaatgcta tactcacaga agtaaatgaa    2580
ctacttgaca ctacacagtt gcaagtagct aatagtttaa tgaatggtgt cactcttagc    2640
actaagctta aagatggcgt taatttcaat gtagacgaca tcaattttc cctgtatta      2700
ggttgtttag gaagcgcttg taataaagtt tccagcagat ctgctataga ggatttactt    2760
tttttctaaag taaagttatc tgatgtcggt ttcgttgagg cttataataa ttgtactgga   2820
ggtgccgaaa ttagggacct catttgtgtg caaagttata atggtatcaa agtgttgcct    2880
ccactgctct cagtaaatca gatcagtgga tacactttgg ctgccacctc tgctagtctg    2940
tttcctcctt ggtcagcagc agcaggtgta ccatttttatt taaatgttca gtatcgtatt   3000
aatgggattg gtgttaccat ggatgtgtta agtcaaaatc aaaagcttat tgctaatgca    3060
tttagcaatg ctcttgatgc tattcaggaa gggtttgatg ctaccaattc tgctttagtt    3120
aaaattcaag ctgttgttaa tgcaaatgct gaagctctta ataacttatt gcaacaactc    3180
tctaatagat ttggtgctat aggttcttct ttacaagaaa ttctatctag actggatgct    3240
cttgaagcgc aagctcagat agacagactt attaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420
aatcatatta tatcattagt gcagaatgct ccatatggtt tgtattttat ccactttagc    3480
tatgtcccta ctaagtatgt cactgcgaag gttagtcccg gtctgtgcat gctggtgat    3540
agaggtatag cccctaagag tggttatttt gttaatgtaa ataatacttg gatgttcact    3600
ggtagtggtt attactaccc tgaaccata actggaaata atgttgttgt tatgagtacc    3660
tgtgctgtta actatactaa agcgccggat gtaatgctga acatttcaac acccaacctc    3720
catgatttta aggaagagtt ggatcaatgg tttaaaaacc aaacatcagt ggcaccagat    3780
ttgtcacttg attatataaa tgttacattc ttggacctac aagatgaaat gaataggtta    3840
caggaggcaa taaaagtttt aaatcagagc tacatcaatc tcaaggacat tggtacatat    3900
gagtattatg taaaatggcc ttggtatgta tggcttttaa ttggctttgc tggtgtagct    3960
atgcttgttt tactattctt catatgctgt tgtacaggat gtgggactag ttgttttaag    4020
atatgtggtg gttgttgtga tgattatact ggacaccagg                         4060
```

<210> SEQ ID NO 16  
<211> LENGTH: 4056  
<212> TYPE: DNA  
<213> ORGANISM: hemagglutinating encephalomyelitis virus

<400> SEQUENCE: 16

```
atgttttta tactttttaat caccctgcct tctgttttg cagttatagg ggatttaaag     60
tgtaatactt catcaattaa tgacgttgac actggtgtgc catctattag ctctgaagtt    120
gttgatgtca ctaatggttt ggggactttc tatgtttag atcgtgtcta tttaaatacc    180
acattgttgc tcaatggtta ttacccaatt tcaggtgcta catttcgtaa tgtggctctg    240
aaaggaactc gattattgag caccttgtgg tttaagccgc ctttttatc acctttaat    300
gatggtattt ttgccaaggt taaaaacagc agattttcta acatggtgt tatttatagt    360
gagtttcctg ctattactat aggtagtact tttgtaaata cttcctatag catagtagta    420
aagcctcata cctcatttat taatggtaat ttacaaggtt ttttgcaaat ttctgtttgt    480
caatatacta tgtgtgaata cccacagact atttgtcatc ctaatttggg taatcaacgc    540
atagaattat ggcatcatga cacagatgtt gtttcttgtt tatacaggcg taatttcaca    600
```

```
tatgatgtga atgctgatta tttatatttt cacttttatc aggaaggtgg cacttttat     660 gcatacttta cagatactgg ttttgtgacc aagtttctgt ttaagttgta tttaggcact    720
gtgctgtcac actattatgt tatgccattg acttgtgata gcgctttatc tttagaatat    780
tgggttacac ctctcactac tagacaattt cttctagcct tgaccagga tggtgtttta    840 taccatgctg ttgattgtgc tagtgatttt atgagtgaga ttatgtgtaa aacttcttca    900
attacaccac ctactggtgt ttatgaacta aacggttaca cagttcaacc tgttgccact    960
gtgtatcgta gaatacctga cttacccaat tgcgatatcg aagcttggct taattctaag   1020
accgtttctt cgcctcttaa ttgggaacgt aaaattttt ctaattgtaa ttttaacatg   1080
ggcaggctga tgtcttttat tcaggctgac tcttttggtt gtaacaatat tgatgcttct   1140
cgcttatatg gtatgtgttt tggtagcatt actattgaca agtttgctat acccaatagt   1200
agaaaggttg atctgcaagt gggtaaatct ggttatttac aatcttttaa ttataagatt   1260
gacactgctg ttagcagttg tcaactctat tatagtttgc ctgcagcaaa cgtatctgtc   1320
actcattata atccttcatc ttggaacaga aggtatgggt ttattaatca gagttttggt   1380
tccagaggcc ttcatgatgc tgtatattca cagcaatgtt ttaatacacc taatacatat   1440
tgtccttgta gaacaagtca atgcataggt ggtgctggca caggaacttg tcctgtaggc   1500
accactgtgc gcaagtgttt tgctgcagtt acaaacgcta ctaagtgtac ttgctggtgt   1560
caaccagatc cttccacata taaggtgta aatgcctgga cttgtccgca atctaaagtt   1620
tctatacaac caggtcagca ttgccctggc ttgggtcttg tggaggatga ttgctctggt   1680
aatccttgca cttgtaaacc acaggctttc ataggctgga gttcagaaac ttgtttgcaa   1740
aatggtaggt gtaatatttt tgctaatttt atttttgaatg atgttaatag cggtactacc   1800
tgttctactg atttacaaca gggtaatact aatattacta ctgatgtttg tgttaattat   1860
gacctatatg gcattacagg ccagggcata cttatagaag ttaatgccac gtattataat   1920
agttggcaga atcttcttta tgattctagt ggtaatctct atggctttag agattattta   1980
tcaaatagaa ccttcttat tcgtagctgc tatagtggaa gagtttcagc agtctttcat   2040
gctaactctt ctgaaccagc tttgatgttt cgtaatctta aatgcagcca cgttttaat   2100 tataccattt aagacaaat acagcttgtt aattattttg atagttacct tggttgtgtt   2160
gttaatgctt ataataatac agctagtgct gtaagtactt gtgatttaac cgttggtagc   2220
ggctattgtg ttgattatgt tacagcactt agatcacgta gatcttttac tacaggttat   2280
cgctttacta attttgaacc atttgccgct aatttggtaa atgatagtat agaacctgtt   2340 ggtggttttgt atgaaataca gatacctca gagtttacca ttggtaattt agaagaattc   2400
attcaaacga gttccctaa ggttactata gattgtgcta catttgtttg tggtgactat   2460
gctgcatgta gacaacagtt agctgagtat ggtagttttt gtgagaacat taatgctata   2520
ctcatagaag taaatgaact acttgacact acacagttgc aagtagctaa tagtttaatg   2580
aatggagtca cccttagtac taagattaag gatgggatta atttcaatgt tgacgatatc   2640
aacttctcct ctgtattagg ttgtttagga agcgaatgta acagagcttc cactagatct   2700
gctatagagg atttacttt tgataaagta aaattgtctg atgtcggttt tgtacaggcc   2760
tataataact gcactggagg agccgaaatt agggatctca tttgtgtgca agttataat   2820 ggtatcaaag tgttgcctcc attgttatct gaaaatcaga ttagtggtta cacttcggca   2880
gccaccgctg ctagcctatt tcctccctgg acagctgcag caggtgtacc attttattta   2940
aatgttcagt atcgtataaa tgggcttggc gtcaccatgg atgtgctaag ccaaaaccaa   3000
```

```
aagcttattg ctagtgcatt taacaacgct cttgattcta tccaggaagg gttcgacgca    3060
accaattctg ctttagttaa aattcaggct gttgttaatg caaatgctga agcacttaat    3120
aacttattgc agcaactctc taacagattt ggtgccataa gtgcctcttt acaagaaatt    3180
ttatccaggc tcgatgctct tgaagctaaa gctcagatag acagacttat taatgggcgt    3240
ctcaccgctc ttaatgctta tgtttctcag cagcttagtg attctacact agtaaaattt    3300
agtgcagcac aagctattga aaagttaatg aatgtgttaa aagccaatca atctaggata    3360
aatttctgtg gtaatggtaa tcatattata tcattagtac agaatgctcc atatggtttg    3420
tattttatcc attttagcta tgtccccacc aagtatgtta cagcaaaggt tagtcctggt    3480
ttgtgcattg ctggcgatat aggaatatcg cctaagagtg ttatttttat taatgtaaat    3540
aactcttgga tgttcactgg tagtggctat tactaccctg aacctataac ccaaaataat    3600
gttgttgtga tgagtacgtg tgctgttaat tatactaaag caccggatct aatgctgaac    3660
acatcgacac ccaaccttcc tgatttcaag gaagaattgt atcaatggtt taaaaaccaa    3720
tcttcattgg caccagattt gtcatttgat tatattaatg ttacgttctt ggacctacaa    3780
gatgaaatga ataggttaca agaagctata aaagttctaa atcatagcta catcaatctc    3840
aaggacattg gtacatatga gtattatgtg aaatggcctt ggtatgtatg cttttaatt    3900 tgccttgctg gtgtagttat gcttgtttta ctattcttca tatgctgctg tacaggatgt    3960
gggactagtt gttttaagaa atgtggcggt tgttttgatg attatactgg acaccaggag    4020
tttgtaatca aaacttcaca tgacgattaa tttcgt                             4056
```

<210> SEQ ID NO 17
<211> LENGTH: 1363
<212> TYPE: PRT
<213> ORGANISM: bovine coronavirus strain LY138

<400> SEQUENCE: 17

```
Met Phe Leu Ile Leu Leu Ile Ser Leu Pro Met Ala Leu Ala Val Ile
1               5                   10                  15

Gly Asp Leu Lys Cys Thr Thr Val Ser Ile Asn Asp Val Asp Thr Gly
            20                  25                  30

Val Pro Ser Val Ser Thr Asp Thr Val Asp Val Thr Asn Gly Leu Gly
        35                  40                  45

Thr Tyr Tyr Val Leu Asp Arg Val Tyr Leu Asn Thr Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Thr Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys Asn Gly Val Met Tyr Ser Glu Phe Pro Ala Ile Thr Ile Gly
        115                 120                 125

Ser Thr Phe Val Asn Thr Ser Tyr Ser Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Ile Glu Leu Trp His Trp Asp Thr Gly Val Val Ser
            180                 185                 190
```

```
Cys Leu Tyr Lys Arg Asn Phe Thr Tyr Asp Val Asn Ala Asp Tyr Leu
            195                 200                 205

Tyr Phe His Phe Tyr Gln Glu Gly Thr Phe Tyr Ala Tyr Phe Thr
        210                 215                 220

Asp Thr Gly Val Val Thr Lys Phe Leu Phe Asn Val Tyr Leu Gly Thr
225                 230                 235                 240

Val Leu Ser His Tyr Tyr Val Met Pro Leu Thr Cys Asn Ser Ala Met
            245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
            275                 280                 285

Asp Phe Met Ser Glu Ile Lys Cys Lys Thr Leu Ser Ile Ala Pro Ser
            290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
            355                 360                 365

Ala Asp Ser Phe Thr Cys Asn Asn Ile Asp Ala Ala Lys Ile Tyr Gly
            370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
                420                 425                 430

Leu Pro Ala Ala Asn Val Ser Val Ser Arg Phe Asn Pro Ser Thr Trp
            435                 440                 445

Asn Arg Arg Phe Gly Phe Thr Glu Gln Ser Val Phe Lys Pro Gln Pro
            450                 455                 460

Val Gly Val Phe Thr Asp His Asp Val Val Tyr Ala Gln His Cys Phe
465                 470                 475                 480

Lys Ala Pro Thr Asn Phe Cys Pro Cys Lys Leu Asp Gly Ser Leu Cys
                485                 490                 495

Val Gly Ser Gly Ser Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
            515                 520                 525

Gln Cys Asn Cys Leu Cys Thr Pro Asp Pro Ile Thr Ser Lys Ser Thr
            530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Val Asp Ser Cys
            580                 585                 590

Leu Gln Gly Asp Arg Cys Asn Ile Phe Ala Asn Phe Ile Leu His Asp
            595                 600                 605
```

-continued

```
Val Asn Ser Gly Thr Thr Cys Ser Thr Asp Leu Gln Lys Ser Asn Thr
    610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
        675                 680                 685

Val Ser Ala Ala Phe His Ala Asn Ser Ser Glu Pro Ala Leu Leu Phe
    690                 695                 700

Arg Asn Ile Lys Cys Asn Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Ala Val Gln Thr Cys Asp Leu Thr Val
            740                 745                 750

Gly Ser Gly Tyr Cys Val Asp Tyr Ser Thr Lys Arg Arg Ser Arg Arg
        755                 760                 765

Ala Ile Thr Thr Gly Tyr Arg Phe Thr Asn Phe Glu Pro Phe Thr Val
    770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Ile Ser Ser Pro Lys Val Thr Ile Asp Cys Ser Ala Phe Val Cys Gly
            820                 825                 830

Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
    850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Asp Cys Asn Lys Val Ser Ser
            900                 905                 910

Arg Ser Ala Ile Glu Asp Leu Leu Phe Ser Lys Val Lys Leu Ser Asp
        915                 920                 925

Val Gly Phe Val Glu Ala Tyr Asn Asn Cys Thr Gly Gly Ala Glu Ile
    930                 935                 940

Arg Asp Leu Ile Cys Val Gln Ser Tyr Asn Gly Ile Lys Val Leu Pro
945                 950                 955                 960

Pro Leu Leu Ser Glu Asn Gln Ile Ser Gly Tyr Thr Leu Ala Ala Thr
                965                 970                 975

Ser Ala Ser Leu Phe Pro Pro Trp Ser Ala Ala Gly Val Pro Phe
            980                 985                 990

Tyr Leu Asn Val Gln Tyr Arg Ile Asn Gly Ile Gly Val Thr Met Asp
        995                 1000                1005

Val Leu Ser Gln Asn Gln Lys Leu Ile Ala Asn Ala Phe Asn Asn
    1010                1015                1020
```

```
Ala Leu Asp Ala Ile Gln Glu Gly Phe Asp Ala Thr Asn Ser Ala
1025                1030                1035

Leu Val Lys Ile Gln Ala Val Val Asn Ala Asn Ala Glu Ala Leu
1040                1045                1050

Asn Asn Leu Leu Gln Gln Leu Ser Asn Arg Phe Gly Ala Ile Ser
1055                1060                1065

Ser Ser Leu Gln Glu Ile Leu Ser Arg Leu Asp Ala Leu Glu Ala
1070                1075                1080

Gln Ala Gln Ile Asp Arg Leu Ile Asn Gly Arg Leu Thr Ala Leu
1085                1090                1095

Asn Ala Tyr Val Ser Gln Gln Leu Ser Asp Ser Thr Leu Val Lys
1100                1105                1110

Phe Ser Ala Ala Gln Ala Met Glu Lys Val Asn Glu Cys Val Lys
1115                1120                1125

Ser Gln Ser Ser Arg Ile Asn Phe Cys Gly Asn Gly Asn His Ile
1130                1135                1140

Ile Ser Leu Val Gln Asn Ala Pro Tyr Gly Leu Tyr Phe Ile His
1145                1150                1155

Phe Ser Tyr Val Pro Thr Lys Tyr Val Thr Ala Lys Val Ser Pro
1160                1165                1170

Gly Leu Cys Ile Ala Gly Asp Arg Gly Ile Ala Pro Lys Ser Gly
1175                1180                1185

Tyr Phe Val Asn Val Asn Asn Thr Trp Met Phe Thr Gly Ser Gly
1190                1195                1200

Tyr Tyr Tyr Pro Glu Pro Ile Thr Gly Asn Asn Val Val Val Met
1205                1210                1215

Ser Thr Cys Ala Val Asn Tyr Thr Lys Ala Pro Asp Val Met Leu
1220                1225                1230

Asn Ile Ser Thr Pro Asn Leu Pro Asp Phe Lys Glu Glu Leu Asp
1235                1240                1245

Gln Trp Phe Lys Asn Gln Thr Ser Val Ala Pro Asp Leu Ser Leu
1250                1255                1260

Asp Tyr Ile Asn Val Thr Phe Leu Asp Leu Gln Asp Glu Met Asn
1265                1270                1275

Arg Leu Gln Glu Ala Ile Lys Val Leu Asn Gln Ser Tyr Ile Asn
1280                1285                1290

Leu Lys Asp Ile Gly Thr Tyr Glu Tyr Tyr Val Lys Trp Pro Trp
1295                1300                1305

Tyr Val Trp Leu Leu Ile Gly Leu Ala Gly Val Ala Met Leu Val
1310                1315                1320

Leu Leu Phe Phe Ile Cys Cys Cys Thr Gly Cys Gly Thr Ser Cys
1325                1330                1335

Phe Lys Lys Cys Gly Gly Cys Cys Asp Asp Tyr Thr Gly His Gln
1340                1345                1350

Glu Leu Val Ile Lys Thr Ser His Asp Asp
1355                1360

<210> SEQ ID NO 18
<211> LENGTH: 1363
<212> TYPE: PRT
<213> ORGANISM: human

-continued

<400> SEQUENCE: 18

```
Met Phe Leu Ile Leu Leu Ile Ser Leu Pro Thr Ala Phe Ala Val Ile
1               5                   10                  15

Gly Asp Leu Lys Cys Thr Thr Val Ser Ile Asn Asp Ile Asp Thr Gly
            20                  25                  30

Ala Pro Ser Ile Ser Thr Asp Ile Val Asp Val Thr Asn Gly Leu Gly
        35                  40                  45

Thr Tyr Tyr Val Leu Asp Arg Val Tyr Leu Asn Thr Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys Lys Gly Val Met Tyr Ser Glu Phe Pro Ala Ile Thr Ile Gly
        115                 120                 125

Ser Thr Phe Val Asn Thr Ser Tyr Ser Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Val Glu Leu Trp His Trp Asp Thr Gly Val Val Ser
            180                 185                 190

Cys Leu Tyr Lys Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
    210                 215                 220

Asp Thr Gly Val Val Thr Lys Phe Leu Phe Asn Val Tyr Leu Gly Thr
225                 230                 235                 240

Val Leu Ser His Tyr Tyr Val Leu Pro Leu Thr Cys Asn Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
    290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
    370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415
```

```
Asn Tyr Arg Ile Asp Thr Thr Ala Thr Ser Cys Gln Leu Tyr Tyr Asn
            420                 425                 430

Leu Pro Ala Ala Asn Val Ser Val Ser Arg Phe Asn Pro Ser Thr Trp
        435                 440                 445

Asn Arg Arg Phe Gly Phe Thr Glu Gln Ser Val Phe Lys Pro Gln Pro
        450                 455                 460

Val Gly Val Phe Thr His His Asp Val Val Tyr Ala Gln His Cys Phe
465                 470                 475                 480

Lys Ala Pro Thr Asn Phe Cys Pro Cys Lys Leu Asp Gly Ser Leu Cys
                485                 490                 495

Val Gly Asn Gly Pro Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
            515                 520                 525

Gln Cys Asp Cys Leu Cys Thr Pro Asp Pro Ile Thr Ser Lys Ser Thr
        530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Val Asp Ser Cys
            580                 585                 590

Leu Gln Gly Asp Arg Cys Asn Ile Phe Ala Asn Phe Ile Leu His Asp
        595                 600                 605

Val Asn Ser Gly Thr Thr Cys Ser Thr Asp Leu Gln Lys Ser Asn Thr
        610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Pro Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
            675                 680                 685

Val Ser Ala Ala Phe His Ala Asn Ser Ser Glu Pro Ala Leu Leu Phe
690                 695                 700

Arg Asn Ile Lys Cys Ser Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
            725                 730                 735

Ala Asp Asn Ser Thr Ser Ser Val Val Gln Thr Cys Asp Leu Thr Val
            740                 745                 750

Gly Ser Gly Tyr Cys Val Asp Tyr Ser Thr Lys Arg Arg Ser Arg Arg
        755                 760                 765

Ala Ile Thr Thr Gly Tyr Arg Phe Thr Asn Phe Glu Pro Phe Thr Val
        770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
            805                 810                 815

Thr Ser Ser Pro Lys Val Thr Ile Asp Cys Ser Ala Phe Val Cys Gly
            820                 825                 830
```

```
Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
        850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
            885                 890                 895

Ser Pro Val Leu Gly Cys Leu Gly Ser Ala Cys Asn Lys Val Ser Ser
                900                 905                 910

Arg Ser Ala Ile Glu Asp Leu Leu Phe Ser Lys Val Lys Leu Ser Asp
            915                 920                 925

Val Gly Phe Val Glu Ala Tyr Asn Asn Cys Thr Gly Gly Ala Glu Ile
        930                 935                 940

Arg Asp Leu Ile Cys Val Gln Ser Tyr Asn Gly Ile Lys Val Leu Pro
945                 950                 955                 960

Pro Leu Leu Ser Val Asn Gln Ile Ser Gly Tyr Thr Leu Ala Ala Thr
                965                 970                 975

Ser Ala Ser Leu Phe Pro Pro Trp Ser Ala Ala Ala Gly Val Pro Phe
            980                 985                 990

Tyr Leu Asn Val Gln Tyr Arg Ile Asn Gly Ile Gly Val Thr Met Asp
        995                 1000                1005

Val Leu Ser Gln Asn Gln Lys Leu Ile Ala Asn Ala Phe Ser Asn
        1010                1015                1020

Ala Leu Asp Ala Ile Gln Glu Gly Phe Asp Ala Thr Asn Ser Ala
        1025                1030                1035

Leu Val Lys Ile Gln Ala Val Val Asn Ala Asn Ala Glu Ala Leu
        1040                1045                1050

Asn Asn Leu Leu Gln Gln Leu Ser Asn Arg Phe Gly Ala Ile Gly
        1055                1060                1065

Ser Ser Leu Gln Glu Ile Leu Ser Arg Leu Asp Ala Leu Glu Ala
        1070                1075                1080

Gln Ala Gln Ile Asp Arg Leu Ile Asn Gly Arg Leu Thr Ala Leu
        1085                1090                1095

Asn Ala Tyr Val Ser Gln Gln Leu Ser Asp Ser Thr Leu Val Lys
        1100                1105                1110

Phe Ser Ala Ala Gln Ala Met Glu Lys Val Asn Glu Cys Val Lys
        1115                1120                1125

Ser Gln Ser Ser Arg Ile Asn Phe Cys Gly Asn Gly Asn His Ile
        1130                1135                1140

Ile Ser Leu Val Gln Asn Ala Pro Tyr Gly Leu Tyr Phe Ile His
        1145                1150                1155

Phe Ser Tyr Val Pro Thr Lys Tyr Val Thr Ala Lys Val Ser Pro
        1160                1165                1170

Gly Leu Cys Ile Ala Gly Asp Arg Gly Ile Ala Pro Lys Ser Gly
        1175                1180                1185

Tyr Phe Val Asn Val Asn Asn Thr Trp Met Phe Thr Gly Ser Gly
        1190                1195                1200

Tyr Tyr Tyr Pro Glu Pro Ile Thr Gly Asn Asn Val Val Val Met
        1205                1210                1215

Ser Thr Cys Ala Val Asn Tyr Thr Lys Ala Pro Asp Val Met Leu
        1220                1225                1230
```

```
Asn Ile Ser Thr Pro Asn Leu His Asp Phe Lys Glu Glu Leu Asp
    1235                1240                1245

Gln Trp Phe Lys Asn Gln Thr Ser Val Ala Pro Asp Leu Ser Leu
    1250                1255                1260

Asp Tyr Ile Asn Val Thr Phe Leu Asp Leu Gln Asp Glu Met Asn
    1265                1270                1275

Arg Leu Gln Glu Ala Ile Lys Val Leu Asn Gln Ser Tyr Ile Asn
    1280                1285                1290

Leu Lys Asp Ile Gly Thr Tyr Glu Tyr Tyr Val Lys Trp Pro Trp
    1295                1300                1305

Tyr Val Trp Leu Leu Ile Gly Phe Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Ile Cys Gly Gly Cys Cys Asp Asp Tyr Thr Gly His Gln
    1340                1345                1350

Glu Leu Val Ile Lys Thr Ser His Asp Asp
    1355                1360

<210> SEQ ID NO 19
<211> LENGTH: 1349
<212> TYPE: PRT
<213> ORGANISM: hemagglutinating encephalomyelitis virus

<400> SEQUENCE: 19

Met Phe Phe Ile Leu Leu Ile Thr Leu Pro Ser Val Phe Ala Val Ile
1               5                   10                  15

Gly Asp Leu Lys Cys Asn Thr Ser Ser Ile Asn Asp Val Asp Thr Gly
            20                  25                  30

Val Pro Ser Ile Ser Ser Glu Val Val Asp Val Thr Asn Gly Leu Gly
        35                  40                  45

Thr Phe Tyr Val Leu Asp Arg Val Tyr Leu Asn Thr Thr Leu Leu Leu
    50                  55                  60

Asn Gly Tyr Tyr Pro Ile Ser Gly Ala Thr Phe Arg Asn Val Ala Leu
65                  70                  75                  80

Lys Gly Thr Arg Leu Leu Ser Thr Leu Trp Phe Lys Pro Pro Phe Leu
                85                  90                  95

Ser Pro Phe Asn Asp Gly Ile Phe Ala Lys Val Lys Asn Ser Arg Phe
            100                 105                 110

Ser Lys His Gly Val Ile Tyr Ser Glu Phe Pro Ala Ile Thr Ile Gly
        115                 120                 125

Ser Thr Phe Val Asn Thr Ser Tyr Ser Ile Val Val Lys Pro His Thr
    130                 135                 140

Ser Phe Ile Asn Gly Asn Leu Gln Gly Phe Leu Gln Ile Ser Val Cys
145                 150                 155                 160

Gln Tyr Thr Met Cys Glu Tyr Pro Gln Thr Ile Cys His Pro Asn Leu
                165                 170                 175

Gly Asn Gln Arg Ile Glu Leu Trp His His Asp Thr Ala Val Val Ser
            180                 185                 190

Cys Leu Tyr Arg Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
    210                 215                 220

Asp Thr Gly Phe Val Thr Lys Phe Leu Phe Lys Leu Tyr Leu Gly Thr
225                 230                 235                 240
```

```
Val Leu Ser His Tyr Tyr Val Met Pro Leu Thr Cys Asp Ser Ala Leu
            245                 250                 255

Ser Leu Glu Tyr Trp Val Thr Pro Leu Thr Thr Arg Gln Phe Leu Leu
            260                 265                 270

Ala Phe Asp Gln Asp Gly Val Leu Tyr His Ala Val Asp Cys Ala Ser
            275                 280                 285

Asp Phe Met Ser Glu Ile Met Cys Lys Thr Ser Ser Ile Thr Pro Pro
            290                 295                 300

Thr Gly Val Tyr Glu Leu Asn Gly Tyr Thr Val Gln Pro Val Ala Thr
305                 310                 315                 320

Val Tyr Arg Arg Ile Pro Asp Leu Pro Asn Cys Asp Ile Glu Ala Trp
            325                 330                 335

Leu Asn Ser Lys Thr Val Ser Ser Pro Leu Asn Trp Glu Arg Lys Ile
            340                 345                 350

Phe Ser Asn Cys Asn Phe Asn Met Gly Arg Leu Met Ser Phe Ile Gln
            355                 360                 365

Ala Asp Ser Phe Gly Cys Asn Asn Ile Asp Ala Ser Arg Leu Tyr Gly
            370                 375                 380

Met Cys Phe Gly Ser Ile Thr Ile Asp Lys Phe Ala Ile Pro Asn Ser
385                 390                 395                 400

Arg Lys Val Asp Leu Gln Val Gly Lys Ser Gly Tyr Leu Gln Ser Phe
            405                 410                 415

Asn Tyr Lys Ile Asp Thr Ala Val Ser Ser Cys Gln Leu Tyr Tyr Ser
            420                 425                 430

Leu Pro Ala Ala Asn Val Ser Val Thr His Tyr Asn Pro Ser Ser Trp
            435                 440                 445

Asn Arg Arg Tyr Gly Phe Ile Asn Gln Ser Phe Gly Ser Arg Gly Leu
            450                 455                 460

His Asp Ala Val Tyr Ser Gln Gln Cys Phe Asn Thr Pro Asn Thr Tyr
465                 470                 475                 480

Cys Pro Cys Arg Thr Ser Gln Cys Ile Gly Gly Ala Gly Thr Gly Thr
            485                 490                 495

Cys Pro Val Gly Thr Thr Val Arg Lys Cys Phe Ala Ala Val Thr Asn
            500                 505                 510

Ala Thr Lys Cys Thr Cys Trp Cys Gln Pro Asp Pro Ser Thr Tyr Lys
            515                 520                 525

Gly Val Asn Ala Trp Thr Cys Pro Gln Ser Lys Val Ser Ile Gln Pro
            530                 535                 540

Gly Gln His Cys Pro Gly Leu Gly Leu Val Glu Asp Asp Cys Ser Gly
545                 550                 555                 560

Asn Pro Cys Thr Cys Lys Pro Gln Ala Phe Ile Gly Trp Ser Ser Glu
            565                 570                 575

Thr Cys Leu Gln Asn Gly Arg Cys Asn Ile Phe Ala Asn Phe Ile Leu
            580                 585                 590

Asn Asp Val Asn Ser Gly Thr Thr Cys Ser Thr Asp Leu Gln Gln Gly
            595                 600                 605

Asn Thr Asn Ile Thr Thr Asp Val Cys Val Asn Tyr Asp Leu Tyr Gly
            610                 615                 620

Ile Thr Gly Gln Gly Ile Leu Ile Glu Val Asn Ala Thr Tyr Tyr Asn
625                 630                 635                 640

Ser Trp Gln Asn Leu Leu Tyr Asp Ser Ser Gly Asn Leu Tyr Gly Phe
            645                 650                 655
```

-continued

```
Arg Asp Tyr Leu Ser Asn Arg Thr Phe Leu Ile Arg Ser Cys Tyr Ser
            660                 665                 670

Gly Arg Val Ser Ala Val Phe His Ala Asn Ser Ser Glu Pro Ala Leu
        675                 680                 685

Met Phe Arg Asn Leu Lys Cys Ser His Val Phe Asn Tyr Thr Ile Leu
    690                 695                 700

Arg Gln Ile Gln Leu Val Asn Tyr Phe Asp Ser Tyr Leu Gly Cys Val
705                 710                 715                 720

Val Asn Ala Tyr Asn Asn Thr Ala Ser Ala Val Ser Thr Cys Asp Leu
                725                 730                 735

Thr Val Gly Ser Gly Tyr Cys Val Asp Tyr Val Thr Ala Leu Arg Ser
            740                 745                 750

Arg Arg Ser Phe Thr Thr Gly Tyr Arg Phe Thr Asn Phe Glu Pro Phe
        755                 760                 765

Ala Ala Asn Leu Val Asn Asp Ser Ile Glu Pro Val Gly Gly Leu Tyr
    770                 775                 780

Glu Ile Gln Ile Pro Ser Glu Phe Thr Ile Gly Asn Leu Glu Glu Phe
785                 790                 795                 800

Ile Gln Thr Ser Ser Pro Lys Val Thr Ile Asp Cys Ala Thr Phe Val
                805                 810                 815

Cys Gly Asp Tyr Ala Ala Cys Arg Gln Gln Leu Ala Glu Tyr Gly Ser
            820                 825                 830

Phe Cys Glu Asn Ile Asn Ala Ile Leu Ile Glu Val Asn Glu Leu Leu
        835                 840                 845

Asp Thr Thr Gln Leu Gln Val Ala Asn Ser Leu Met Asn Gly Val Thr
    850                 855                 860

Leu Ser Thr Lys Ile Lys Asp Gly Ile Asn Phe Asn Val Asp Asp Ile
865                 870                 875                 880

Asn Phe Ser Ser Val Leu Gly Cys Leu Gly Ser Glu Cys Asn Arg Ala
                885                 890                 895

Ser Thr Arg Ser Ala Ile Glu Asp Leu Leu Phe Asp Lys Val Lys Leu
            900                 905                 910

Ser Asp Val Gly Phe Val Gln Ala Tyr Asn Asn Cys Thr Gly Gly Ala
        915                 920                 925

Glu Ile Arg Asp Leu Ile Cys Val Gln Ser Tyr Asn Gly Ile Lys Val
    930                 935                 940

Leu Pro Pro Leu Leu Ser Glu Asn Gln Ile Ser Gly Tyr Thr Ser Ala
945                 950                 955                 960

Ala Thr Ala Ala Ser Leu Phe Pro Pro Trp Thr Ala Ala Ala Gly Val
                965                 970                 975

Pro Phe Tyr Leu Asn Val Gln Tyr Arg Ile Asn Gly Leu Gly Val Thr
            980                 985                 990

Met Asp Val Leu Ser Gln Asn Gln  Lys Leu Ile Ala Ser  Ala Phe Asn
        995                 1000                 1005

Asn Ala  Leu Asp Ser Ile Gln  Glu Gly Phe Asp Ala  Thr Asn Ser
    1010                 1015                 1020

Ala Leu  Val Lys Ile Gln Ala  Val Val Asn Ala Asn  Ala Glu Ala
    1025                 1030                 1035

Leu Asn  Asn Leu Leu Gln Gln  Leu Ser Asn Arg Phe  Gly Ala Ile
    1040                 1045                 1050

Ser Ala  Ser Leu Gln Glu Ile  Leu Ser Arg Leu Asp  Ala Leu Glu
    1055                 1060                 1065
```

```
Ala Lys Ala Gln Ile Asp Arg Leu Ile Asn Gly Arg Leu Thr Ala
    1070            1075            1080

Leu Asn Ala Tyr Val Ser Gln Gln Leu Ser Asp Ser Thr Leu Val
    1085            1090            1095

Lys Phe Ser Ala Ala Gln Ala Ile Glu Lys Val Asn Glu Cys Val
    1100            1105            1110

Lys Ser Gln Ser Ser Arg Ile Asn Phe Cys Gly Asn Gly Asn His
    1115            1120            1125

Ile Ile Ser Leu Val Gln Asn Ala Pro Tyr Gly Leu Tyr Phe Ile
    1130            1135            1140

His Phe Ser Tyr Val Pro Thr Lys Tyr Val Thr Ala Lys Val Ser
    1145            1150            1155

Pro Gly Leu Cys Ile Ala Gly Asp Ile Gly Ile Ser Pro Lys Ser
    1160            1165            1170

Gly Tyr Phe Ile Asn Val Asn Asn Ser Trp Met Phe Thr Gly Ser
    1175            1180            1185

Gly Tyr Tyr Tyr Pro Glu Pro Ile Thr Gln Asn Asn Val Val Val
    1190            1195            1200

Met Ser Thr Cys Ala Val Asn Tyr Thr Lys Ala Pro Asp Leu Met
    1205            1210            1215

Leu Asn Thr Ser Thr Pro Asn Leu Pro Asp Phe Lys Glu Glu Leu
    1220            1225            1230

Tyr Gln Trp Phe Lys Asn Gln Ser Ser Leu Ala Pro Asp Leu Ser
    1235            1240            1245

Phe Asp Tyr Ile Asn Val Thr Phe Leu Asp Leu Gln Asp Glu Met
    1250            1255            1260

Asn Arg Leu Gln Glu Ala Ile Lys Val Leu Asn His Ser Tyr Ile
    1265            1270            1275

Asn Leu Lys Asp Ile Gly Thr Tyr Glu Tyr Tyr Val Lys Trp Pro
    1280            1285            1290

Trp Tyr Val Trp Leu Leu Ile Cys Leu Ala Gly Val Val Met Leu
    1295            1300            1305

Val Leu Leu Phe Phe Ile Cys Cys Cys Thr Gly Cys Gly Thr Ser
    1310            1315            1320

Cys Phe Lys Lys Cys Gly Gly Cys Phe Asp Asp Tyr Thr Gly His
    1325            1330            1335

Gln Glu Phe Val Ile Lys Thr Ser His Asp Asp
    1340            1345

<210> SEQ ID NO 20
<211> LENGTH: 1453
<212> TYPE: PRT
<213> ORGANISM: canine enteric coronavirus

<400> SEQUENCE: 20

Met Ile Val Leu Val Thr Cys Ile Leu Leu Leu Cys Ser Tyr His Thr
1               5                   10                  15

Ala Ser Ser Thr Ser Asn Asn Asp Cys Arg Gln Val Asn Val Thr Gln
                20                  25                  30

Leu Asp Gly Asn Glu Asn Leu Ile Arg Asp Phe Leu Phe Gln Asn Phe
            35                  40                  45

Lys Glu Glu Gly Thr Val Val Val Gly Gly Tyr Tyr Pro Thr Glu Val
        50                  55                  60

Trp Tyr Asn Cys Ser Arg Thr Ala Thr Thr Thr Ala Tyr Glu Tyr Phe
65                  70                  75                  80
```

-continued

```
Ser Asn Ile His Ala Phe Tyr Phe Asp Met Glu Ala Met Glu Asn Ser
             85                  90                  95

Thr Gly Asn Ala Arg Gly Lys Pro Leu Leu Phe His Val His Gly Glu
            100                 105                 110

Pro Val Ser Val Ile Ile Tyr Ile Ser Tyr Arg Asp Asp Val Gln His
            115                 120                 125

Arg Pro Leu Leu Lys His Gly Leu Val Cys Ile Thr Glu Ser Arg Asn
130                 135                 140

Ile Asp Tyr Asn Ser Phe Thr Ser Ser Gln Trp Asn Ser Ile Cys Thr
145                 150                 155                 160

Gly Asn Asp Arg Lys Ile Pro Phe Ser Val Ile Pro Thr Asp Asn Gly
                165                 170                 175

Thr Lys Ile Tyr Gly Leu Glu Trp Asn Asp Glu Phe Val Thr Ala Tyr
                180                 185                 190

Ile Ser Gly Arg Ser Tyr Asn Trp Asn Ile Asn Asn Asn Trp Phe Asn
            195                 200                 205

Asn Val Thr Leu Leu Tyr Ser Arg Ser Ser Thr Ala Thr Trp Gln His
            210                 215                 220

Ser Ala Ala Tyr Val Tyr Gln Gly Val Ser Asn Phe Tyr Tyr Lys
225                 230                 235                 240

Leu Asn Asn Thr Asn Gly Leu Lys Thr Tyr Glu Leu Cys Glu Asp Tyr
                245                 250                 255

Glu Tyr Cys Thr Gly Tyr Ala Thr Asn Ile Phe Ala Pro Thr Val Gly
            260                 265                 270

Gly Tyr Ile Pro Asp Gly Phe Ser Phe Asn Asn Trp Phe Leu Leu Thr
            275                 280                 285

Asn Ser Ser Thr Phe Val Ser Gly Arg Phe Val Thr Asn Gln Pro Leu
290                 295                 300

Leu Val Asn Cys Leu Trp Pro Val Pro Ser Phe Gly Val Ala Ala Gln
305                 310                 315                 320

Glu Phe Cys Phe Glu Gly Ala Gln Phe Ser Gln Cys Asn Gly Val Phe
                325                 330                 335

Leu Asn Asn Thr Val Asp Val Ile Arg Phe Asn Leu Asn Phe Thr Ala
                340                 345                 350

Asp Val Gln Ser Gly Met Gly Ala Thr Val Phe Ser Leu Asn Thr Thr
            355                 360                 365

Gly Gly Cys Ile Leu Glu Ile Ser Cys Tyr Asn Asp Ile Val Ser Glu
            370                 375                 380

Ser Ser Phe Tyr Ser Tyr Gly Glu Ile Pro Phe Gly Val Thr Asp Gly
385                 390                 395                 400

Pro Arg Tyr Cys Tyr Val Leu Tyr Asn Gly Thr Ala Leu Lys Tyr Phe
                405                 410                 415

Gly Thr Leu Pro Pro Ser Val Lys Glu Ile Ala Ile Ser Lys Trp Gly
                420                 425                 430

Gln Phe Tyr Ile Asn Gly Tyr Asn Phe Phe Ser Thr Phe Pro Ile Asp
            435                 440                 445

Cys Ile Ser Phe Asn Leu Thr Thr Gly Asp Ser Gly Ala Phe Trp Thr
450                 455                 460

Ile Ala Tyr Thr Ser Tyr Thr Glu Ala Leu Val Gln Val Glu Asn Thr
465                 470                 475                 480

Ala Ile Lys Lys Val Thr Tyr Cys Asn Ser His Ile Asn Asn Ile Lys
                485                 490                 495
```

-continued

```
Cys Ser Gln Leu Thr Ala Asn Leu Gln Asn Gly Phe Tyr Pro Val Ala
            500                 505                 510
Ser Ser Glu Val Gly Leu Val Asn Lys Ser Val Val Leu Leu Pro Ser
            515                 520                 525
Phe Tyr Ser His Thr Ser Val Asn Ile Thr Ile Asp Leu Gly Met Lys
            530                 535                 540
Arg Ser Gly Tyr Gly Gln Pro Ile Ala Ser Thr Leu Ser Asn Ile Thr
545                 550                 555                 560
Leu Pro Met Gln Asp Asn Asn Thr Asp Val Tyr Cys Ile Arg Ser Asn
                565                 570                 575
Gln Phe Ser Val Tyr Val His Ser Thr Cys Lys Ser Ser Leu Trp Asp
                580                 585                 590
Asn Asn Phe Asn Gln Asp Cys Thr Asp Val Leu Tyr Ala Thr Ala Val
                595                 600                 605
Ile Lys Thr Gly Thr Cys Pro Phe Ser Phe Asp Lys Leu Asn Asn Tyr
            610                 615                 620
Leu Thr Phe Asn Lys Leu Cys Leu Ser Leu Asn Pro Thr Gly Ala Asn
625                 630                 635                 640
Cys Lys Phe Asp Val Ala Ala Arg Thr Arg Thr Asn Glu Gln Val Val
                645                 650                 655
Arg Ser Leu Tyr Val Ile Tyr Glu Glu Gly Asp Asn Ile Val Gly Val
            660                 665                 670
Pro Ser Asp Asn Ser Gly Leu His Asp Leu Ser Val Leu His Leu Asp
            675                 680                 685
Ser Cys Thr Asp Tyr Asn Ile Tyr Gly Arg Thr Gly Val Gly Ile Ile
            690                 695                 700
Arg Gln Thr Asn Ser Thr Ile Leu Ser Gly Leu His Tyr Thr Ser Leu
705                 710                 715                 720
Ser Gly Asp Leu Leu Gly Phe Lys Asn Val Ser Asp Gly Val Val Tyr
                725                 730                 735
Ser Val Thr Pro Cys Asp Val Ser Ala Gln Ala Ala Val Ile Asp Gly
            740                 745                 750
Ala Ile Val Gly Ala Met Thr Ser Ile Asn Ser Glu Leu Leu Gly Leu
            755                 760                 765
Thr His Trp Thr Thr Thr Pro Asn Phe Tyr Tyr Tyr Ser Ile Tyr Asn
            770                 775                 780
Thr Thr Asn Glu Arg Thr Arg Gly Thr Ala Ile Asp Ser Asn Asp Val
785                 790                 795                 800
Asp Cys Glu Pro Ile Ile Thr Tyr Ser Asn Ile Gly Val Cys Lys Asn
                805                 810                 815
Gly Ala Leu Val Phe Ile Asn Val Thr His Ser Asp Gly Asp Val Gln
                820                 825                 830
Pro Ile Ser Thr Gly Asn Val Thr Ile Pro Thr Asn Phe Thr Ile Ser
            835                 840                 845
Val Gln Val Glu Tyr Ile Gln Val Tyr Thr Thr Pro Val Ser Ile Asp
            850                 855                 860
Cys Ser Arg Tyr Val Cys Asn Gly Asn Pro Arg Cys Asn Lys Leu Leu
865                 870                 875                 880
Thr Gln Tyr Val Ser Ala Cys Gln Thr Ile Glu Gln Ala Leu Ala Met
                885                 890                 895
Ser Ala Ser Leu Glu Asn Met Glu Val Asp Ser Met Leu Phe Val Ser
                900                 905                 910
```

-continued

```
Glu Asn Ala Leu Lys Leu Ala Ser Val Glu Ala Phe Asn Ser Thr Glu
        915                 920                 925
His Leu Asp Pro Ile Tyr Lys Glu Trp Pro Asn Ile Gly Gly Ser Trp
    930                 935                 940
Leu Gly Gly Leu Lys Asp Ile Leu Pro Ser His Asn Ser Lys Arg Lys
945                 950                 955                 960
Tyr Arg Ser Ala Ile Glu Asp Leu Leu Phe Asp Lys Val Val Thr Ser
                965                 970                 975
Gly Leu Gly Thr Val Asp Glu Asp Tyr Lys Arg Cys Thr Gly Gly Tyr
            980                 985                 990
Asp Ile Ala Asp Leu Val Cys Ala Gln Tyr Tyr Asn Gly Ile Met Val
        995                 1000                1005
Leu Pro Gly Val Ala Asn Asp Asp Lys Met Thr Met Tyr Thr Ala
    1010                1015                1020
Ser Leu Ala Gly Gly Ile Ala Leu Gly Ala Leu Gly Gly Gly Ala
    1025                1030                1035
Val Ala Ile Pro Phe Ala Val Ala Val Gln Ala Arg Leu Asn Tyr
    1040                1045                1050
Val Ala Leu Gln Thr Asp Val Leu Asn Lys Asn Gln Gln Ile Leu
    1055                1060                1065
Ala Asn Ala Phe Asn Gln Ala Ile Gly Asn Ile Thr Gln Ala Phe
    1070                1075                1080
Gly Lys Val Asn Asp Ala Ile His Gln Thr Ser Gln Gly Leu Ala
    1085                1090                1095
Thr Val Ala Lys Ala Leu Ala Lys Val Gln Asp Val Val Asn Thr
    1100                1105                1110
Gln Gly Gln Ala Leu Ser His Leu Thr Val Gln Leu Gln Asn Ser
    1115                1120                1125
Phe Gln Ala Ile Ser Ser Ser Ile Ser Asp Ile Tyr Asn Arg Leu
    1130                1135                1140
Asp Glu Leu Ser Ala Asp Ala Gln Val Asp Arg Leu Ile Thr Gly
    1145                1150                1155
Arg Leu Thr Ala Leu Asn Ala Phe Val Ser Gln Thr Leu Thr Arg
    1160                1165                1170
Gln Ala Glu Val Arg Ala Ser Arg Gln Leu Ala Lys Asp Lys Val
    1175                1180                1185
Asn Glu Cys Val Arg Ser Gln Ser Gln Arg Phe Gly Phe Cys Gly
    1190                1195                1200
Asn Gly Thr His Leu Phe Ser Leu Ala Asn Ala Ala Pro Asn Gly
    1205                1210                1215
Met Val Phe Phe His Thr Val Leu Leu Pro Thr Ala Tyr Glu Thr
    1220                1225                1230
Val Thr Ala Trp Ser Gly Ile Cys Ala Ser Asp Gly Asp Arg Thr
    1235                1240                1245
Phe Gly Leu Val Val Lys Asp Val Gln Leu Thr Leu Phe Arg Asn
    1250                1255                1260
Leu Asp Asp Lys Phe Tyr Leu Thr Pro Arg Thr Met Tyr Gln Pro
    1265                1270                1275
Arg Ala Ala Thr Ser Ser Asp Phe Val Gln Ile Glu Gly Cys Asp
    1280                1285                1290
Val Leu Phe Val Asn Ala Thr Val Ile Asp Leu Pro Ser Ile Ile
    1295                1300                1305
```

```
Pro Asp Tyr Ile Asp Ile Asn Gln Thr Val Gln Asp Ile Leu Glu
    1310                1315                1320

Asn Tyr Arg Pro Asn Trp Thr Val Pro Glu Leu Thr Ile Asp Ile
    1325                1330                1335

Phe Asn Ala Thr Tyr Leu Asn Leu Thr Gly Glu Ile Asp Asp Leu
    1340                1345                1350

Glu Phe Arg Ser Glu Lys Leu His Asn Thr Thr Val Glu Leu Ala
    1355                1360                1365

Ile Leu Ile Asp Asn Ile Asn Asn Thr Leu Val Asn Leu Glu Trp
    1370                1375                1380

Leu Asn Arg Ile Glu Thr Tyr Val Lys Trp Pro Trp Tyr Val Trp
    1385                1390                1395

Leu Leu Ile Gly Leu Val Val Val Phe Cys Ile Pro Leu Leu Leu
    1400                1405                1410

Phe Cys Cys Cys Ser Thr Gly Cys Cys Gly Cys Ile Gly Cys Leu
    1415                1420                1425

Gly Ser Cys Cys His Ser Ile Cys Ser Arg Arg Gln Phe Glu Asn
    1430                1435                1440

Tyr Glu Pro Ile Glu Lys Val His Val His
    1445                1450

<210> SEQ ID NO 21
<211> LENGTH: 496
<212> TYPE: DNA
<213> ORGANISM: canine respiratory coronavirus

<400> SEQUENCE: 21
tatcgcagcc ttacttttgt taatgtacca tatgtttata atggctctgc acaatctaca    60
gctctttgta atctggtag tttagttctt aataaccctg catatatagc tcgtgaagct   120
aattttgggg attattatta taaggttgaa gctgatttct atttgtcagg ttgtgacgag   180
tatatcgtac cactttgtat ttttaacggc aagttttgt cgaatacaaa gtattatgat   240
gatagtcaat attattttaa taaagacact ggtgttattt atggtttcaa ttctactgaa   300
accattaaca ctggttttga ttttaattgt cattatttac ttttaccctc tggtaattat   360
ttagccattt caaatgagct attgttaact gttcctacga aagcaatctg tcttaataag   420
cgtaaggatt ttacgcctgt acaggttgtt gactcgcggt ggaacaatgc caggcagtct   480
gataacatga cggcgg                                                    496

<210> SEQ ID NO 22
<211> LENGTH: 165
<212> TYPE: PRT
<213> ORGANISM: canine respiratory coronavirus

<400> SEQUENCE: 22

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
            20                  25                  30

Pro Ala Tyr Ile Ala Arg Glu Ala Asn Phe Gly Asp Tyr Tyr Tyr Lys
        35                  40                  45

Val Glu Ala Asp Phe Tyr Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80
```

```
Asp Ser Gln Tyr Tyr Phe Asn Lys Asp Thr Gly Val Ile Tyr Gly Phe
                85                  90                  95

Asn Ser Thr Glu Thr Ile Asn Thr Gly Phe Asp Phe Asn Cys His Tyr
            100                 105                 110

Leu Leu Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Asp Phe
    130                 135                 140

Thr Pro Val Gln Val Val Asp Ser Arg Trp Asn Asn Ala Arg Gln Ser
145                 150                 155                 160

Asp Asn Met Thr Ala
            165

<210> SEQ ID NO 23
<211> LENGTH: 497
<212> TYPE: DNA
<213> ORGANISM: bovine coronavirus strain LY138

<400> SEQUENCE: 23
tatcgcagcc ttacttttgt taatgtacca tatgtttata atggctctgc acaatctaca    60
gctctttgta aatctggtag tttagttctt aataaccctg catatatagc tcgtgaagct   120
aattttgggg attattatta taaggttgaa gctgattttt atttgtcagg ttgtgacgag   180
tatatcgtac cactttgtat ttttaacggc aagtttttgt cgaatacaaa gtattatgat   240
gatagtcaat attattttaa taaagacact ggtgttattt atggtctcaa ttctactgaa   300
accattacca ctggttttga ttttaattgt cattatttag ttttaccctc tggtaattat   360
ttagccattt caaatgagct attgttaact gttcctacga aagcaatctg tcttaataag   420
cgtaaggatt ttacgcctgt acaggttgtt gactctcggt ggaacaatgc aggcagtct    480 gataacatga cggcggt                                                  497

<210> SEQ ID NO 24
<211> LENGTH: 497
<212> TYPE: DNA
<213> ORGANISM: human coronavirus strain OC43

<400> SEQUENCE: 24
tatcgcagcc ttacttttgt taatgtacca tatgtttata atggctctgc acaatctaca    60
gctctttgta aatctggtag tttagtcctt aataaccctg catatatagc tcctcaagct   120
aactctgggg attattatta taaggttgaa gctgattttt atttgtcagg ttgtgacgag   180
tatatcgtac cactttgtat ttttaacggc aagtttttgt cgaatacaaa gtattatgat   240
gatagtcaat attattttaa taaagacact ggtgttattt atggtctcaa ttctacagaa   300
accattacca ctggttttga tcttaattgt tattatttag ttttaccctc tggtaattat   360
ttagccattt caaatgagct attgttaact gttcctacga aagcaatctg tcttaataag   420
cgtaaggatt ttacgcctgt acaggttgtt gattcgcggt ggaacaatgc aggcagtct    480 gataacatga cggcggt                                                  497

<210> SEQ ID NO 25
<211> LENGTH: 497
<212> TYPE: DNA
<213> ORGANISM: human enteric coronavirus
```

```
<400> SEQUENCE: 25
tatcgcagcc ttactttttgt taatgtacca tatgtttaca atggctctgc acaatctaca     60
gctctttgta aatctggtag tttagttctt aataaccctg catatatagc tcgtgaagct    120
aattttgggg attattatta taaggttgaa gctgattttt atttgtcagg ttgtgacgag    180
tatatcgtac cactttgtat ttttaacggc aagttttttgt cgaatacaaa gtattatgat    240
gatagtcaat attattttaa taaagacact ggtgttattt atggtctcaa ttctactgaa    300
accattacca ctggttttga ttttaattgt cattatttag ttctaccctc tggcaattat    360
ttagccattt caaatgagct attgttaact gttcctacta aagcaatctg tcttaataag    420
cgtaaggatt ttacgcctgt acaggttgtt gactcgcggt ggaacaatgc caggcagtct    480
gataacatga cggcagt                                                    497

<210> SEQ ID NO 26
<211> LENGTH: 497
<212> TYPE: DNA
<213> ORGANISM: hemagglutinating encephalomyelitis virus

<400> SEQUENCE: 26
tatcgcagtc ttactttagt taatgtgcca tacgtttaca atgggtcagc tcaacccacc     60
gcactttgta agtctggcag tttaattctt aacaatcctg catatatagc ccgtgaggct    120
aatgtgggtg attattatta taagtctgaa gcagattttt ctctctcagg ttgtgacgag    180
tatatcgtac cactttgtat ttttaatggc aagttttttgt cgaatacaaa gtattatgat    240
gatagtcaat attatttaa taaagacact ggtgttattt atggtctcaa ttctactgaa    300
accattacca ctggttttga ttttaattgt cattatttag ttctaccctc tggtaattat    360
ctagccattt caaatgagct attgttaact gttcctacta aagcaatctg tcttaataag    420
cgtaaggttt ttacgcctgt acaggttgtt gattcgcggt ggaacaatgc caggcaatct    480
gataacatga cggcagt                                                    497

<210> SEQ ID NO 27
<211> LENGTH: 165
<212> TYPE: PRT
<213> ORGANISM: bovine coronavirus strain LY138

<400> SEQUENCE: 27

Tyr Arg Ser Leu Thr Phe Val Asn Val Pro Tyr Val Tyr Asn Gly Ser
 1               5                  10                  15

Ala Gln Ser Thr Ala Leu Cys Lys Ser Gly Ser Leu Val Leu Asn Asn
            20                  25                  30

Pro Ala Tyr Ile Ala Arg Glu Ala Asn Phe Gly Asp Tyr Tyr Tyr Lys
        35                  40                  45

Val Glu Ala Asp Phe Tyr Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
            100                 105                 110

Leu Val Leu Pro Ser Gly Asn Tyr Leu Ala Ile Ser Asn Glu Leu Leu
        115                 120                 125
```

```
Leu Thr Val Pro Thr Lys Ala Ile Cys Leu Asn Lys Arg Lys Asp Phe
    130                 135                 140

Thr Pro Val Gln Val Val Asp Ser Arg Trp Asn Asn Ala Arg Gln Ser
145                 150                 155                 160

Asp Asn Met Thr Ala
            165

<210> SEQ ID NO 28
<211> LENGTH: 165
<212> TYPE: PRT
<213> ORGANISM: human coronavirus strain OC43

<400> SEQUENCE: 28

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
            20                  25                  30

Pro Ala Tyr Ile Ala Pro Gln Ala Asn Ser Gly Asp Tyr Tyr Tyr Lys
        35                  40                  45

Val Glu Ala Asp Phe Tyr Leu Ser Gly Cys Asp Glu Tyr Ile Val Pro
50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Leu Asn Cys Tyr Tyr
            100                 105                 110

Leu Val Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Asp Phe
    130                 135                 140

Thr Pro Val Gln Val Val Asp Ser Arg Trp Asn Asn Ala Arg Gln Ser
145                 150                 155                 160

Asp Asn Met Thr Ala
            165

<210> SEQ ID NO 29
<211> LENGTH: 165
<212> TYPE: PRT
<213> ORGANISM: human enteric coronavirus

<400> SEQUENCE: 29

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
            20                  25                  30

Pro Ala Tyr Ile Ala Arg Glu Ala Asn Phe Gly Asp Tyr Tyr Tyr Lys
        35                  40                  45

Val Glu Ala Asp Phe Tyr Leu Ser Gly Cys Asp Glu Tyr Ile Val Pro
50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
            100                 105                 110
```

```
Leu Val Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Asp Phe
        130                 135                 140

Thr Pro Val Gln Val Val Asp Ser Arg Trp Asn Asn Ala Arg Gln Ser
145                 150                 155                 160

Asp Asn Met Thr Ala
                165

<210> SEQ ID NO 30
<211> LENGTH: 165
<212> TYPE: PRT
<213> ORGANISM: hemagglutinating encephalomyelitis virus

<400> SEQUENCE: 30

Tyr Arg Ser Leu Thr Leu Val Asn Val Pro Tyr Val Tyr Asn Gly Ser
1               5                   10                  15

Ala Gln Pro Thr Ala Leu Cys Lys Ser Gly Ser Leu Ile Leu Asn Asn
            20                  25                  30

Pro Ala Tyr Ile Ala Arg Glu Ala Asn Val Gly Asp Tyr Tyr Tyr Lys
        35                  40                  45

Ser Glu Ala Asp Phe Ser Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
            100                 105                 110

Leu Val Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Val Phe
        130                 135                 140

Thr Pro Val Gln Val Val Asp Ser Arg Trp Asn Asn Ala Arg Gln Ser
145                 150                 155                 160

Asp Asn Met Thr Ala
                165

<210> SEQ ID NO 31
<211> LENGTH: 23
<212> TYPE: DNA
<213> ORGANISM: artificial
<220> FEATURE:
<223> OTHER INFORMATION: Consensus oligonucleotide primer for
      coronavirus polymerase gene

<400> SEQUENCE: 31
actcaratga atttgaaata tgc                                        23

<210> SEQ ID NO 32
<211> LENGTH: 20
<212> TYPE: DNA
<213> ORGANISM: artificial
<220> FEATURE:
<223> OTHER INFORMATION: Consensus oligonucleotide primer for
      coronavirus polymerase gene

<400> SEQUENCE: 32
tcacacttag gatartccca                                            20
```

<210> SEQ ID NO 33
<211> LENGTH: 20
<212> TYPE: DNA
<213> ORGANISM: artificial
<220> FEATURE:
<223> OTHER INFORMATION: Consensus oligonucleotide probe for coronavirus
      polymerase gene

<400> SEQUENCE: 33
aagttttatg gyggytggga                                              20

<210> SEQ ID NO 34
<211> LENGTH: 24
<212> TYPE: DNA
<213> ORGANISM: bovine coronavirus strain LY138

<400> SEQUENCE: 34
cttataagtg cccccaaact aaat                                         24

<210> SEQ ID NO 35
<211> LENGTH: 23
<212> TYPE: DNA
<213> ORGANISM: bovine coronavirus strain LY138

<400> SEQUENCE: 35
cctactgtga gatcacatgt ttg                                          23

<210> SEQ ID NO 36
<211> LENGTH: 21
<212> TYPE: DNA
<213> ORGANISM: bovine coronavirus strain LY138

<400> SEQUENCE: 36
gttggcatag gtgagcacct g                                            21

<210> SEQ ID NO 37
<211> LENGTH: 20
<212> TYPE: DNA
<213> ORGANISM: bovine coronavirus strain LY138

<400> SEQUENCE: 37
gcaatgctgg ttcggaagag                                              20

<210> SEQ ID NO 38
<211> LENGTH: 20
<212> TYPE: DNA
<213> ORGANISM: bovine coronavirus strain LY138

<400> SEQUENCE: 38
tatcgcagcc ttactttgt                                               20

<210> SEQ ID NO 39
<211> LENGTH: 19
<212> TYPE: DNA
<213> ORGANISM: bovine coronavirus strain LY138

<400> SEQUENCE: 39
accgccgtca tgttatcag                                               19

<210> SEQ ID NO 40
<211> LENGTH: 24
<212> TYPE: DNA
<213> ORGANISM: bovine coronavirus strain LY138

```
<400> SEQUENCE: 40
cttataagtg cccccaaact aaat                                          24

<210> SEQ ID NO 41
<211> LENGTH: 23
<212> TYPE: DNA
<213> ORGANISM: bovine coronavirus strain LY138

<400> SEQUENCE: 41
cctactgtga gatcacatgt ttg                                           23

<210> SEQ ID NO 42
<211> LENGTH: 20
<212> TYPE: DNA
<213> ORGANISM: bovine coronavirus strain LY138

<400> SEQUENCE: 42
gttggcatag gtgagcactg                                               20

<210> SEQ ID NO 43
<211> LENGTH: 20
<212> TYPE: DNA
<213> ORGANISM: bovine coronavirus strain LY138

<400> SEQUENCE: 43
gcaatgctgg ttcggaagag                                               20

<210> SEQ ID NO 44
<211> LENGTH: 20
<212> TYPE: DNA
<213> ORGANISM: bovine coronavirus strain LY138

<400> SEQUENCE: 44
aacggttaca ctgttcagcc                                               20

<210> SEQ ID NO 45
<211> LENGTH: 20
<212> TYPE: DNA
<213> ORGANISM: bovine coronavirus strain LY138

<400> SEQUENCE: 45
caagtaaatg agtctgcctg                                               20

<210> SEQ ID NO 46
<211> LENGTH: 20
<212> TYPE: DNA
<213> ORGANISM: bovine coronavirus strain LY138

<400> SEQUENCE: 46
ggctgccacc tctgctagtc                                               20

<210> SEQ ID NO 47
<211> LENGTH: 25
<212> TYPE: DNA
<213> ORGANISM: bovine coronavirus strain LY138

<400> SEQUENCE: 47
attgttaaat gcattagcaa taagc                                         25

<210> SEQ ID NO 48
<211> LENGTH: 26
<212> TYPE: DNA
<213> ORGANISM: bovine coronavirus strain LY138
```

```
-continued

<400> SEQUENCE: 48
tttttgatac ttttaatttc cttacc                                         26

<210> SEQ ID NO 49
<211> LENGTH: 24
<212> TYPE: DNA
<213> ORGANISM: bovine coronavirus strain LY138

<400> SEQUENCE: 49
gtcgtcatgt gawgttttra ttac                                           24

<210> SEQ ID NO 50
<211> LENGTH: 35
<212> TYPE: DNA
<213> ORGANISM: artificial
<220> FEATURE:
<223> OTHER INFORMATION: Oligonucleotide primer for cloning canine
      respiratory coronavirus Spike gene

<400> SEQUENCE: 50
agctcgagct ttttgatact tttaatttcc ttacc                               35

<210> SEQ ID NO 51
<211> LENGTH: 53
<212> TYPE: DNA
<213> ORGANISM: artificial
<220> FEATURE:
<223> OTHER INFORMATION: Oligonucleotide primer for cloning canine
      respiratory coronavirus Spike gene

<400> SEQUENCE: 51
ttgaattctt aatgatgatg atgatgatgg tcgtcatgtg awgttttrat tac            53

<210> SEQ ID NO 52
<211> LENGTH: 11
<212> TYPE: PRT
<213> ORGANISM: Unknown
<220> FEATURE:
<223> OTHER INFORMATION: Presumed T cell epitope

<400> SEQUENCE: 52

Thr Ala Ser Gly Val Ala Glu Thr Thr Asn Cys
1               5                   10
```